(12) United States Patent
Kletschka et al.

(10) Patent No.: US 7,322,957 B2
(45) Date of Patent: *Jan. 29, 2008

(54) ANGIOPLASTY DEVICE AND METHOD OF MAKING SAME

(75) Inventors: Harold D. Kletschka, 1925 Noble Dr., Minneapolis, MN (US) 55422; Brian Packard, Monticello, MN (US)

(73) Assignee: Harold D. Kletschka, Minneapolis, MN (US)

( * ) Notice: Subject to any disclaimer, the term of this patent is extended or adjusted under 35 U.S.C. 154(b) by 449 days.

This patent is subject to a terminal disclaimer.

(21) Appl. No.: 10/163,077

(22) Filed: Jun. 4, 2002

(65) Prior Publication Data

US 2003/0009190 A1     Jan. 9, 2003

Related U.S. Application Data

(63) Continuation-in-part of application No. 09/718,732, filed on Nov. 22, 2000, now abandoned, which is a continuation-in-part of application No. 09/495,833, filed on Feb. 1, 2000, now Pat. No. 6,443,926.

(51) Int. Cl.
*A61M 29/00*      (2006.01)
(52) U.S. Cl. .................. 604/96; 606/198; 606/200
(58) Field of Classification Search ................. 606/113, 606/114, 159, 191, 194, 198, 200; 604/96.01, 604/104, 108, 109
See application file for complete search history.

(56) References Cited

U.S. PATENT DOCUMENTS 4,794,928 A     1/1989     Kletschka
4,909,258 A     3/1990     Kuntz et al.
4,966,596 A     10/1990    Kuntz et al.
5,055,109 A     10/1991    Gould et al.
5,100,423 A *   3/1992     Fearnot ..................... 606/159

(Continued)

FOREIGN PATENT DOCUMENTS

DE        197 22 429 A1    12/1998

(Continued)

OTHER PUBLICATIONS

*International Congress XII on Endovascular Interventions*, Henry et al.; A New Cerebral Protection Device for Cartoid Angioplasty and Stenting. First Clinical Experience with the PercuSurge Guardwire.

(Continued)

*Primary Examiner*—Michael J. Hayes
*Assistant Examiner*—Nguyen Victor
(74) *Attorney, Agent, or Firm*—David E. Bruhn

(57) ABSTRACT

An angioplasty device and particle trap for use in removal of a particle from a small diameter vessel or vessel-like structure is disclosed. One embodiment includes a catheter for insertion into a vessel-like structure, the catheter having a catheter wall and a movable member, a trap operably connected to the catheter wall and to the movable member, wherein relative motion between the catheter wall and the movable member actuates the trap. In one embodiment, the expanded trap is formed from struts in a spiral-shaped configuration. In one embodiment, the contracted trap forms a waist to creates a pinch-point to trap particles. In one embodiment, the contracted trap forms a cocoon-like structure to further trap particles. In one embodiment, the angioplasty device includes a handle to actuate the trap from a contracted position to an expanded position and return to a contracted position. The handle provides rotational or longitudinal or both types of movement to actuate the trap.

20 Claims, 41 Drawing Sheets

U.S. PATENT DOCUMENTS

| | | | |
|---|---|---|---|
| 5,120,323 A | | 6/1992 | Shockey et al. |
| 5,190,542 A | * | 3/1993 | Nakao et al. ................ 606/47 |
| 5,192,286 A | * | 3/1993 | Phan et al. ................ 606/127 |
| 5,242,460 A | | 9/1993 | Klein et al. |
| 5,441,516 A | | 8/1995 | Wang et al. |
| 5,658,296 A | | 8/1997 | Bates et al. |
| 5,662,671 A | | 9/1997 | Barbut et al. ................ 606/170 |
| 5,814,064 A | | 9/1998 | Daniel et al. ................ 606/200 |
| 5,833,644 A | | 11/1998 | Zadno-Azizi et al. |
| 5,833,650 A | | 11/1998 | Imran |
| 5,954,745 A | | 9/1999 | Gertler et al. ................ 606/159 |
| 6,001,118 A | * | 12/1999 | Daniel et al. ................ 606/200 |
| 6,022,336 A | | 2/2000 | Zadno-Azizi et al. |
| 6,027,863 A | | 2/2000 | Donadio, III |
| 6,050,972 A | | 4/2000 | Zadno-Azizi et al. |
| 6,066,158 A | | 5/2000 | Engelson et al. |
| 6,068,623 A | | 5/2000 | Zadno-Azizi et al. |
| 6,139,557 A | | 10/2000 | Passafaro et al. |
| 6,165,200 A | | 12/2000 | Tsugita et al. ................ 606/200 |
| 6,231,588 B1 | | 5/2001 | Zadno-Azizi ................ 606/200 |
| 6,277,138 B1 | * | 8/2001 | Levinson et al. ............ 606/200 |
| 6,277,139 B1 | | 8/2001 | Levinson et al. ............ 606/200 |
| 6,398,756 B2 | | 6/2002 | Peterson et al. ......... 604/96.01 |
| 6,443,926 B1 | * | 9/2002 | Kletschka ................ 604/96.01 |
| 6,485,456 B1 | * | 11/2002 | Kletschka ................ 604/96.01 |

FOREIGN PATENT DOCUMENTS

| | | |
|---|---|---|
| WO | 9744082 | 11/1997 |
| WO | 9744084 | 11/1997 |
| WO | 9744085 | 11/1997 |
| WO | 9838929 | 9/1998 |
| WO | 9838930 | 9/1998 |
| WO | 9839044 | 11/1998 |
| WO | 9856440 | 12/1998 |
| WO | 9926692 | 6/1999 |
| WO | 9942059 | 8/1999 |
| WO | 9942157 | 8/1999 |
| WO | 9942158 | 8/1999 |
| WO | 9942164 | 8/1999 |
| WO | WO 99/47053 | 9/1999 |
| WO | 0007657 | 2/2000 |
| WO | 0029060 | 5/2000 |
| WO | 0050113 | 8/2000 |
| WO | 0054673 | 9/2000 |
| WO | WO 01/56644 | 8/2001 |

OTHER PUBLICATIONS

Harold D. Kletschka, M.D., Projected Enhancement and Extension of Application of Transluminal Angioplasty Catheters Using Kletschka Angioplasty Trap-Barrier Device; p. 1-29.

Oesterle et al.: A Coaxial Catheter; System for the Prevention of Distal Embolization.

*Simon Nitinol Filter* .

*Clinical Neurosurgery, Proceedings of the Congress of Neurological Surgeons*, Smith et al.; Transluminal Angioplasty of the Cerebral Circulation; 1983, pp. 117-134.

*Radiligy*, Kensey et al.; Recanalization of Obstructed Arteries with A Flexible, Rotating Tip Catheter, Nov. 1987, pp. 387-389.

*Journal of Vascular Surgery*, Labs et al; Analysis of solid phase debris from laser angioplasty: Potential risks of atheroembolism; Feb. 1988, pp. 326-335.

*Interventional Radiology*, Coleman et al.: Atheroablation with the Kensey Catheter: A Pathologic Study; Feb. 1989, pp. 391-394.

Cardio, Barbara J. Dwyer: Atherectomy Devices: A Clinical Comparison: Apr. 1989, pp. 123-129.

*Mayo Clinic Proceedings*: Kaufmann et al.: Coronary Atherectomy: First 50 Patients at the Mayo Clinic; Jul. 1989, pp. 747-752.

*RoFo*, Schild et al.; Klinische Erfahrungen mit dem Kensey-Katheter-System Komplikationen und Ergbnisse, Feb. 1990, pp. 168-172.

*Catheterization and Cardiovascular Diagnosis*, Titus et al.: Distal Embolization during mechanical Thrombolysis: Rotational Thrombectomy vs. Balloon Angioplasty; 1990, pp. 279-285.

Mayo Clinic Proceedings, Holmes, Jr. et al.: Advances in Inteventional Cardiology; Apr. 1990, pp. 565-583.

AJNR, Robert Ferguson, Getting it Right the First Time, Sep./Oct. 1990, pp. 11:875-877.

Cardiovasc Intervent Radiokl, Matsumoto et al.: Percutaneous Management of Emboli Associated with Hot Tip Laser-Assisted Angioplasty, 1990, pp. 13:71-74.

AJNR, Theron et al.: New Triple Coaxial Catheter System for Carotid Angioplasty with Cerebral Protection, Sep./Oct. 1990, pp. 11:869-874.

J Endovasc. Surg. Henry et al., Angioplasty and stenting of the Extracranial Carotid Arteries; 1998, pp. 5:293-304.

Texas Heart Institute Journal, Diethrich, Carotid Angioplasty and Stenting; 1998, vol. 25, No. 1, pp. 1-9.

*J. Endovasc. Surg.*, Henry et al.; Carotid Stenting with Cerebral Protection: First Clinical Experience Using the PercuSurge GuardWire System, 1999, pp. 6:321-331.

Various Embolic Protective Devices, Summary on 2 sheets (4 pages).

Simon Nitinol Filter, 2 sheets (4 pages) of Bard Advertisement handout.

Advanced Talent System, 1 sheet, 1 page handout by World Medical Manufacturing Corporation.

Proximal Grab Method, Regarding Amplatz "Goose Neck"™ Snares & Microsnares, 2 sheets, 4 pages, Handout of Microvena Corporation.

Rotablator Reference Guide, 2 sheets, 1 page on each sheet copyright 1998.

*Interventional Cardiology*, Walter Alexander,: Promise Seen in Carotid Treatments, May 2000, p. 21.

*Can Med Assoc J*, D. Lynn Doyle: Update on laser angioplasty, 1990, p. 1391.

* cited by examiner

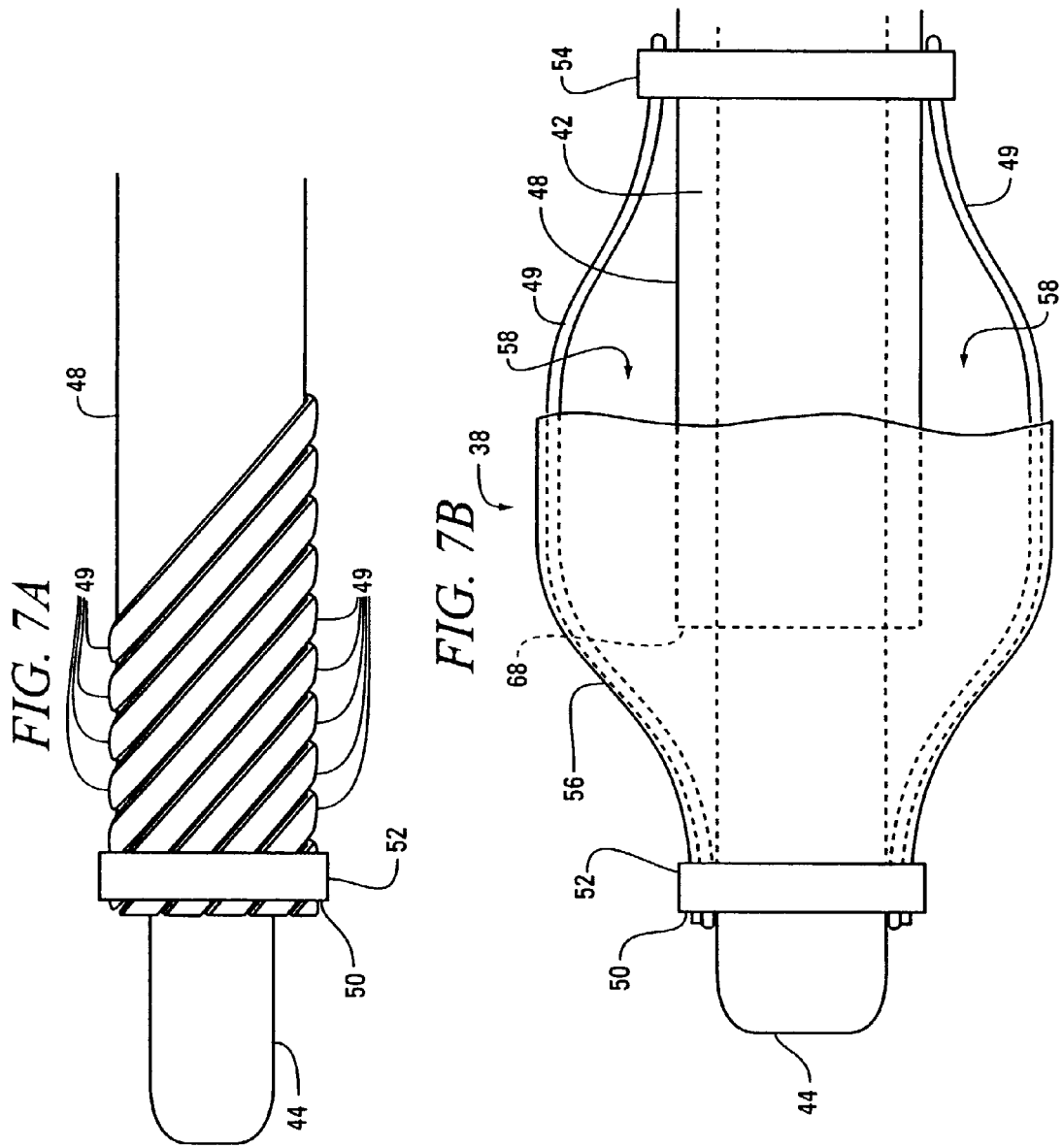

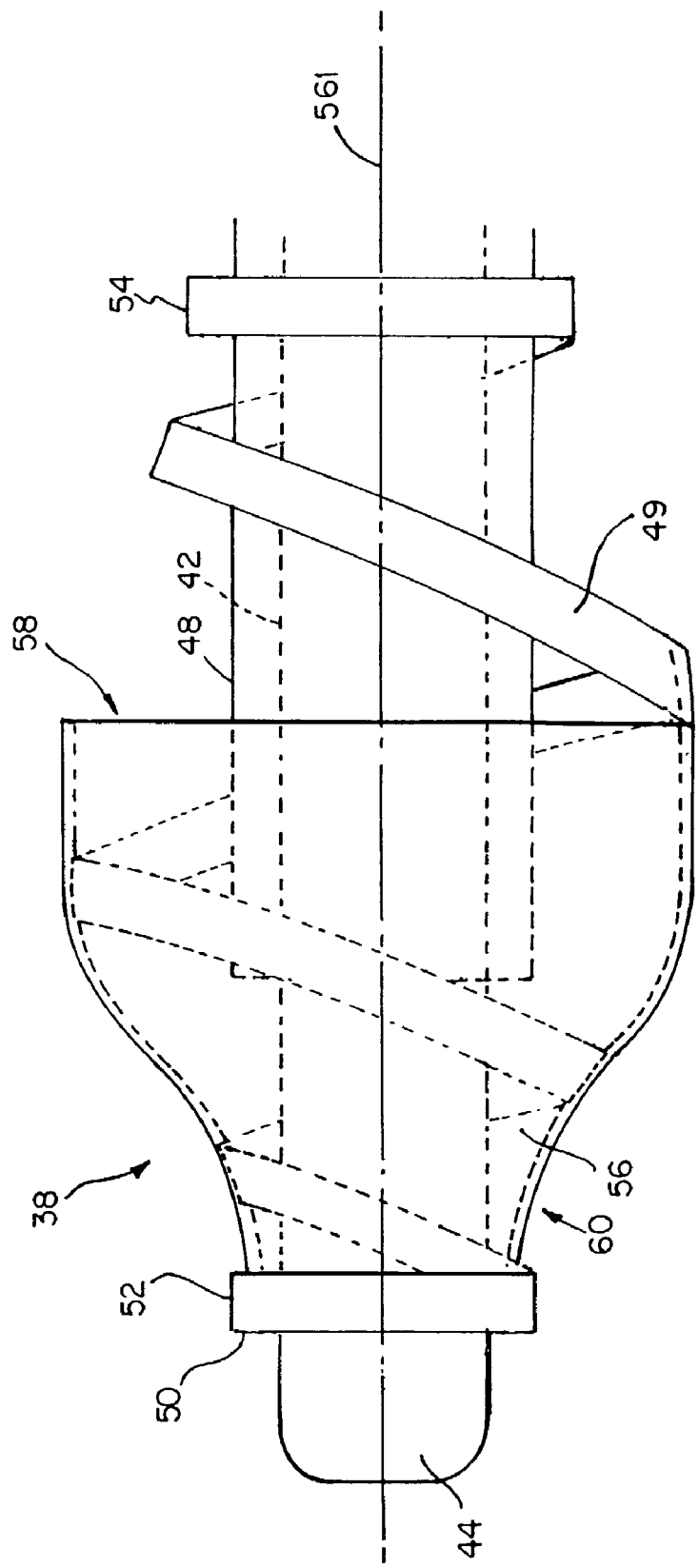

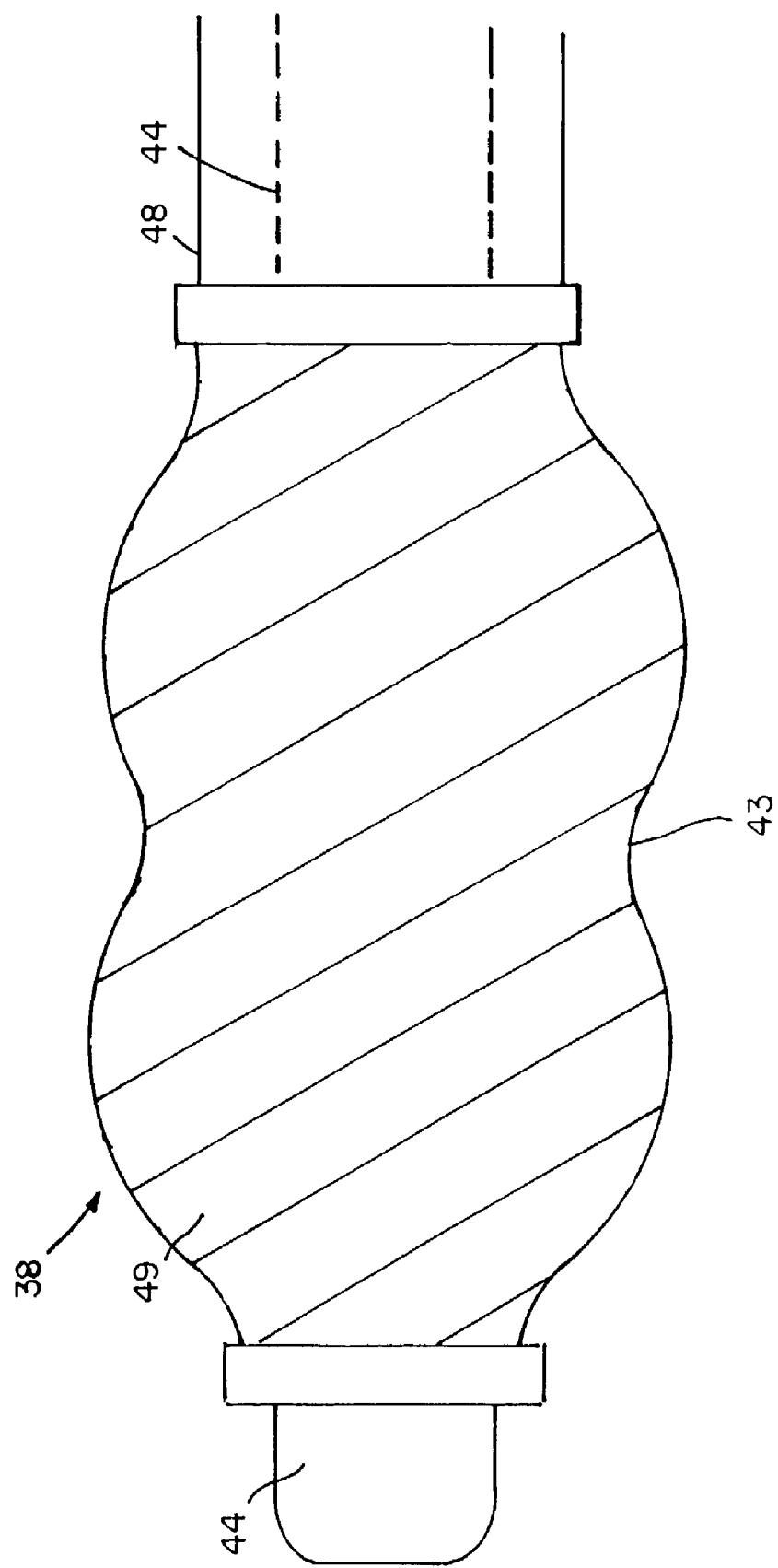

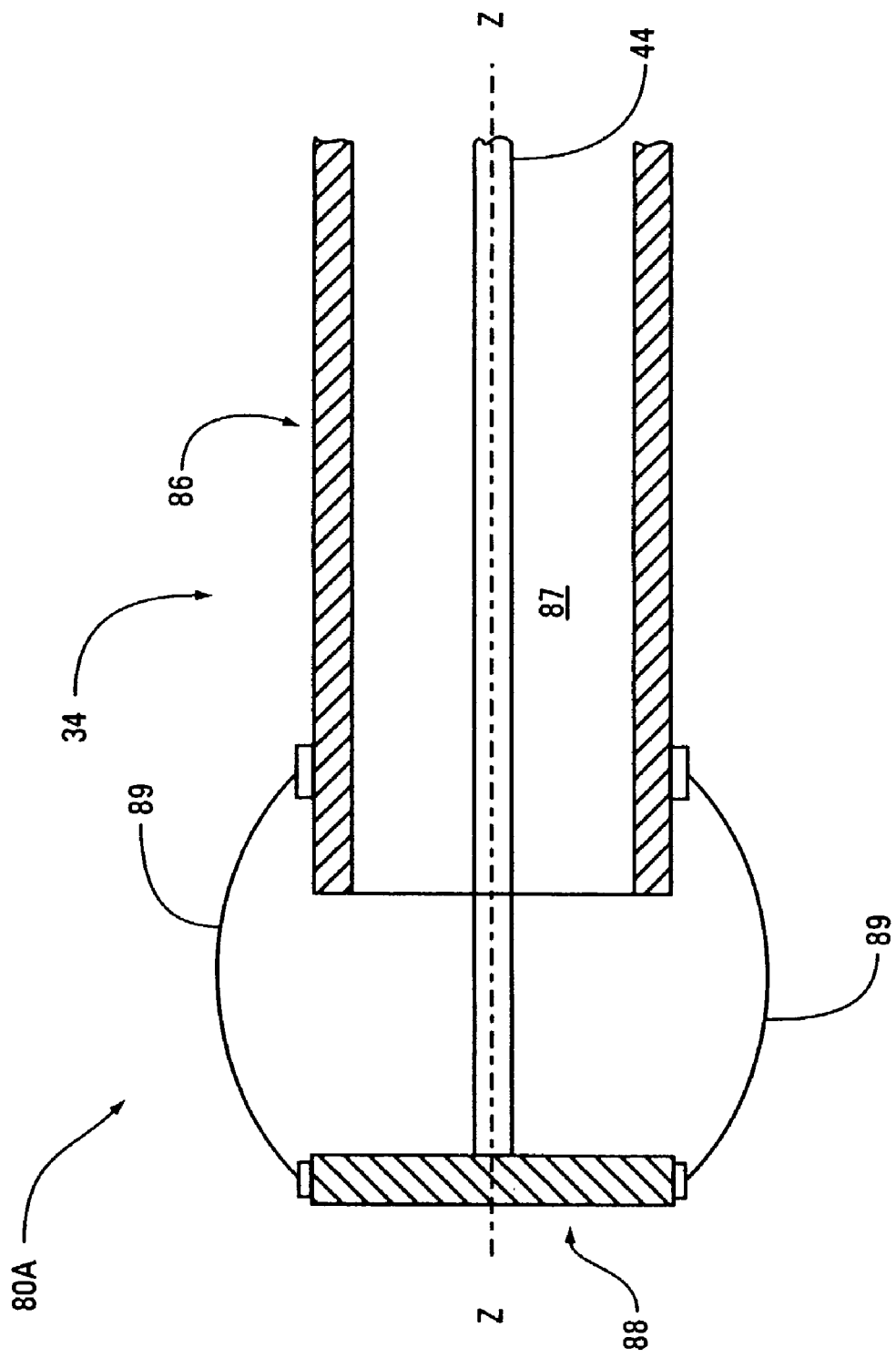

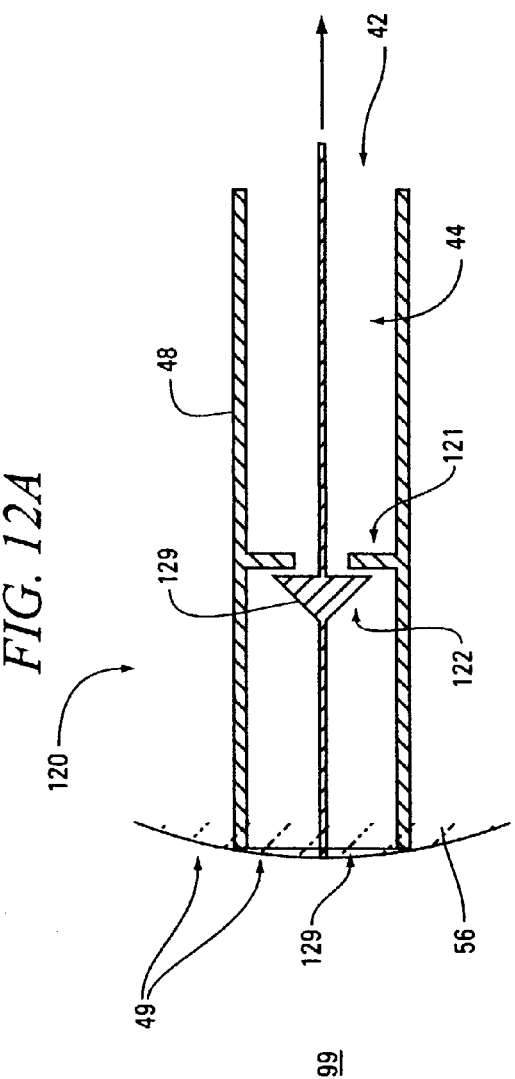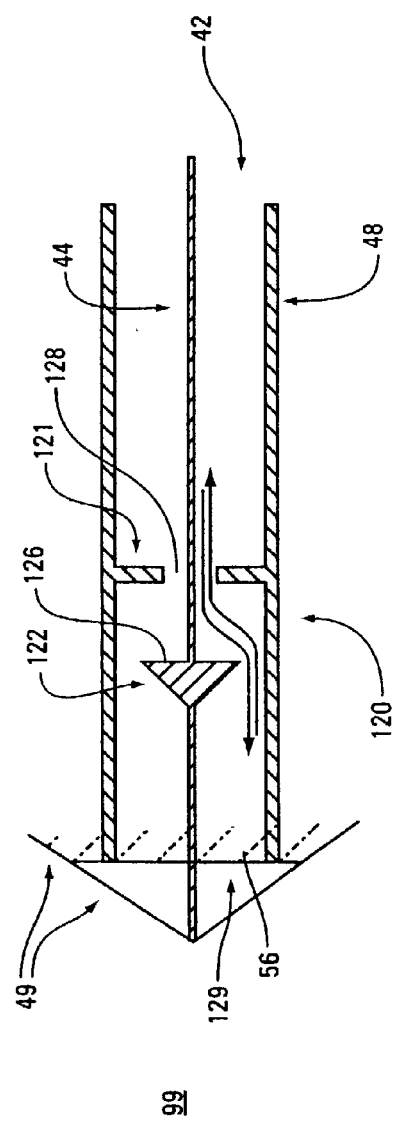

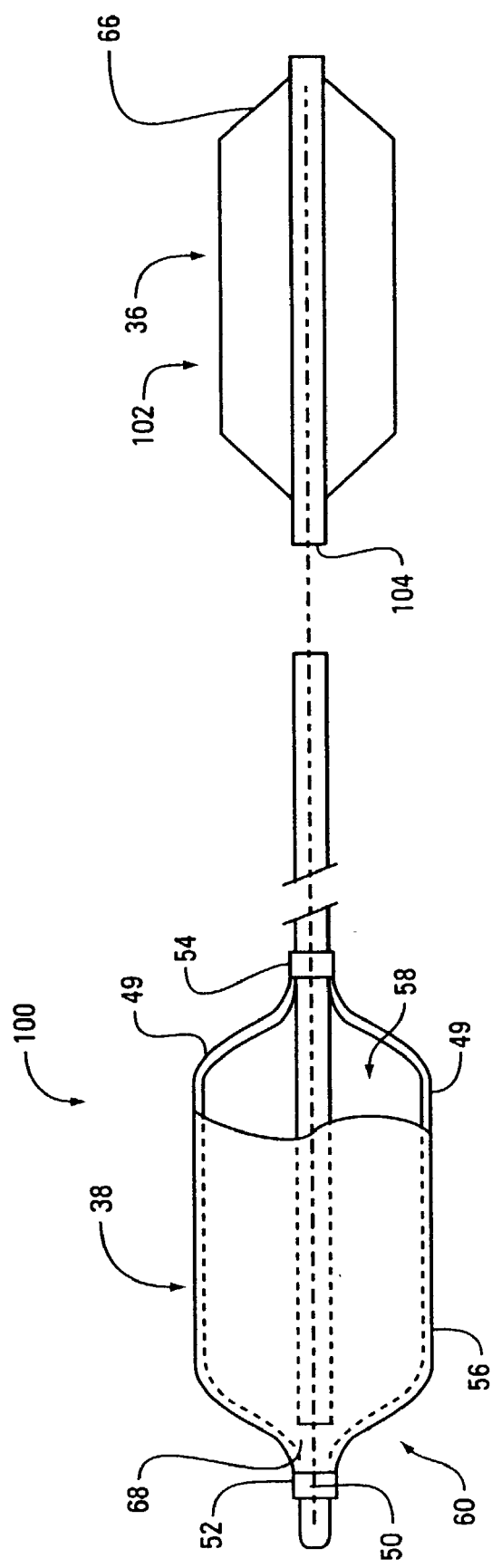

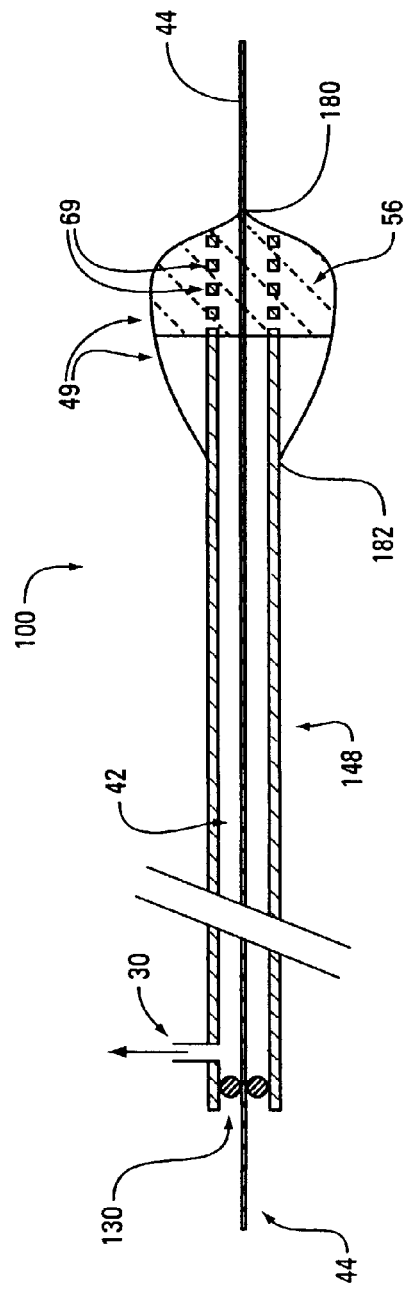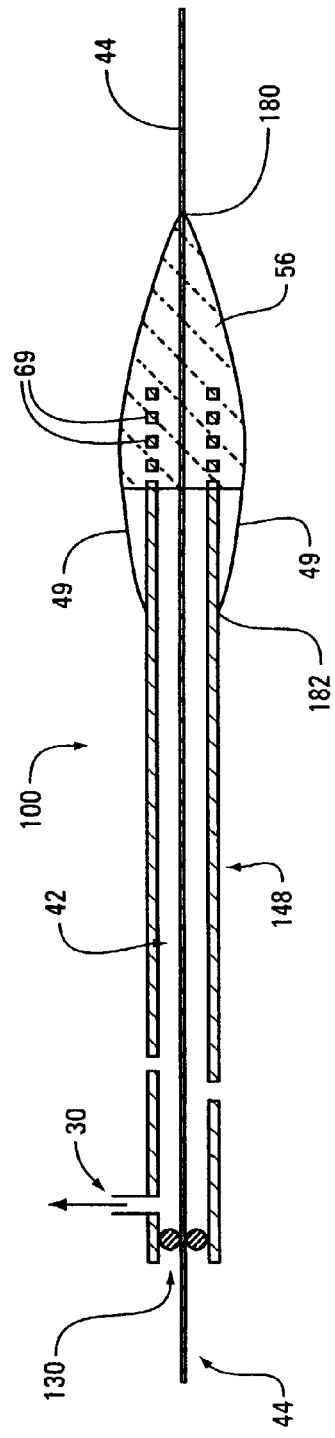

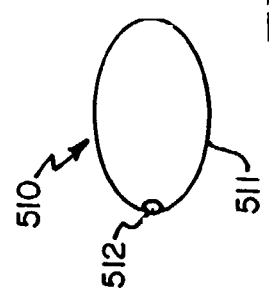
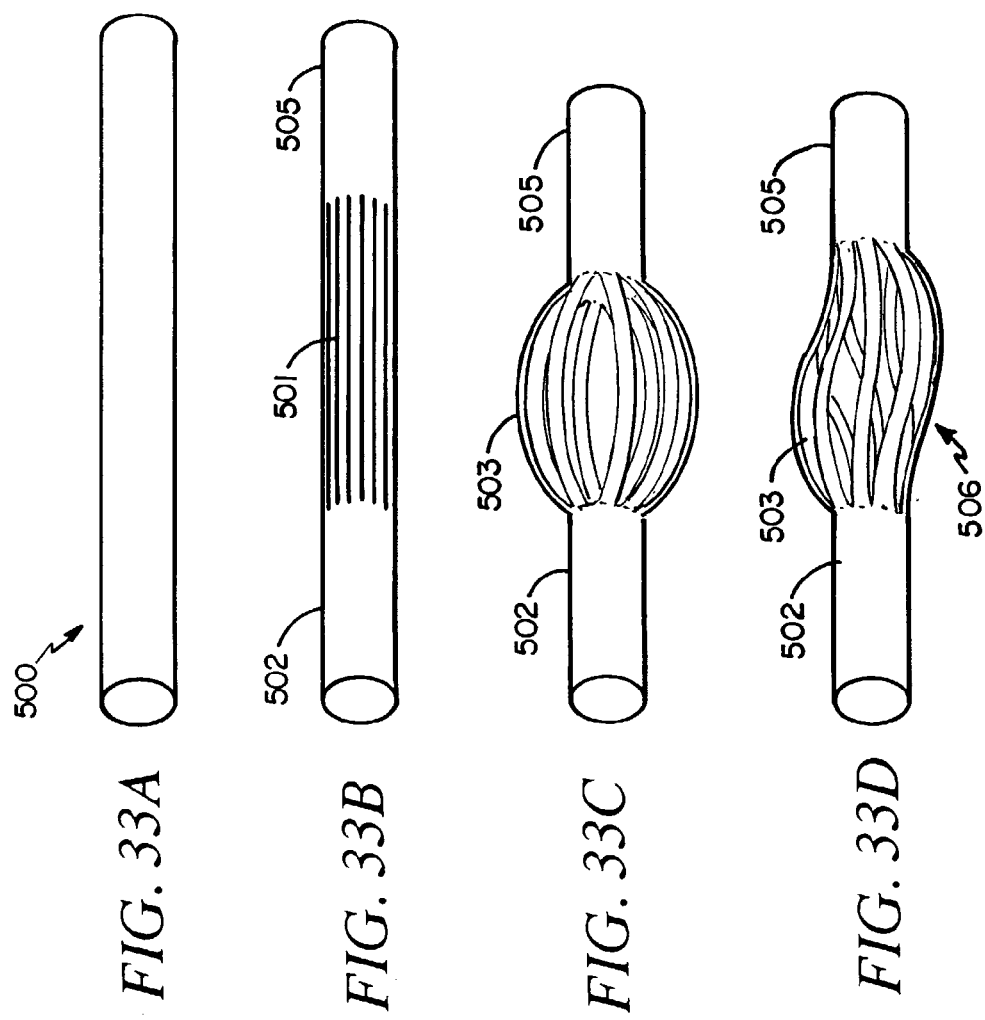
FIG. 33A
FIG. 33B
FIG. 33C
FIG. 33D
FIG. 33E

ANGIOPLASTY DEVICE AND METHOD OF MAKING SAME

CROSS-REFERENCE TO RELATED APPLICATION(S)

This application is a continuation-in-part of U.S. patent application Ser. No. 09/718,732, filed Nov. 22, 2000 now abandoned which is a continuation-in-part of U.S. patent application Ser. No. 09/495,833, filed Feb. 1, 2000 now U.S. Pat. No. 6,443,926, both of which are herein incorporated by reference.

TECHNICAL FIELD

This invention relates to an angioplasty device for compressing and/or removing atherosclerotic plaques, thromboses, stenoses, occlusions, clots, potential embolic material and so forth (hereinafter "obstructions") from veins, arteries, vessels, ducts and the like (hereinafter "vessels"). More particularly, the invention relates to a total capture angioplasty device and trap capable of use in small and large diameter vessels and vessel-like structures.

BACKGROUND OF THE INVENTION

Angioplasty devices are used to treat a wide variety of conditions and to perform a wide variety of procedures, including without limitation: congenital or acquired stenoses or obstructions; percutaneous aspiration thromboembolectomy; cerebral embolization; congenital or acquired obstruction or stenosis of the aorta, renal, coronary, pulmonary, iliac, femoral, popliteal, peroneal, dorsalis pedis, subclavian, axillary, brachial, radial, ulnar, vertebral, cerebral and/or cerebellar artery or any other accessible artery or their ramifications; congenital or acquired obstruction or stenosis of the superior vena cava, inferior vena cava, common iliac, internal iliac, external iliac, femoral, greater saphenous, lesser saphenous, posterior tibial, peroneal, popliteal, pulmonary, coronary, coronary sinus, innominate, brachial, cephalic, basilic, internal jugular, external jugular, cerebral, cerebellar, sinuses of the dura mater and/or vertebral vein or any other accessible vein or their ramifications; atheromatous lesions of any graft or its ramifications; obstructions or stenoses of connections between and among grafts, veins, arteries, organs and ducts; vena caval bleeding; congenital or acquired intracardiac obstructions, stenoses, shunts and/or aberrant communications; congenital or acquired cardiovascular obstructions, stenoses and/or diseases; infusion of thrombolytic agents; thromboembolic phenomena; diagnostic catheterization; removal of clots; intrahepatic and/or extrahepatic biliary ductal obstructions (e.g., stones, sediment or strictures); intravascular, intracardiac and/or intraductal foreign bodies; renal dialysis; congenital and acquired esophageal and/or gastrointestinal obstructions and/or stenoses; non-organized atheromata; dialysis fistula stenosis; ruptured cerebral aneurysm; arterio-arterial, arterio-venous and/or veno-venous fistulae; ureteral obstructions (e.g., stones, sediment or strictures); fibromuscular dysplasia of the renal artery, carotid artery and/or other blood vessels; and/or atherosclerosis of any accessible artery, vein or their ramifications. Such procedures may be performed in both humans and in other applications.

Conventional angioplasty devices generally consist of a catheter containing a balloon-like member that is inserted into an occluded vessel. Expansion of the balloon at the obstruction site crushes the obstruction against the interior lining of the vessel. When the balloon is retracted, the obstruction remains pressed against the vessel wall and the effective diameter of the vessel through which fluid may flow is increased at the site of the obstruction. Examples of angioplasty devices incorporating a balloon are shown in U.S. Pat. Nos. 4,646,742; 4,636,195; 4,587,975; and 4,273,128.

Other conventional angioplasty devices have been developed that incorporate expandable meshes or braids, drilling or cutting members, or lasers as a means for removing an obstruction. Examples of these angioplasty devices are illustrated by U.S. Pat. Nos. 4,445,509; 4,572,186; 4,576,177; 4,589,412; 4,631,052; 4,641,912; and 4,650,466.

Many problems have been associated with these angioplasty devices. Perhaps the most significant problem is the creation of particulate matter during the obstruction removal procedure. Recent ex vivo studies have demonstrated that huge numbers of emboli are produced on inflation and on deflation of the angioplasty balloon during dilation of a stenotic lesion. See Ohki T. Ex vivo carotid stenting, (Presentation) ISES International Congress XI, Feb. 11, 1998. These particles are released into the fluid flowing through the vessel and can lead to emboli, clots, stroke, heart failure, hypertension and decreased renal function, acute renal failure, livedo reticularis and gangrene of the lower extremities, abdominal pain and pancreatitis, cerebral infarction and retinal emboli, tissue injury, tissue death, emergency bypass surgery, death and other undesirable side effects and complications. Regardless of the type of angioplasty device used, a substantial number of particles will be generated.

Even very small particles can cause significant harm. The cross-sectional diameter of normal capillaries varies for different parts of the body and may be comprised of vessels as small as 2.0-3.5μ for very thin capillaries or 3.55-5.0μ for moderately thin capillaries. Accordingly, any particles that exceed these sizes can lodge inside the vessel. Furthermore, in the case of the heart, approximately 45% of the capillaries are closed at any given time, so that any particle, no matter how small, dislodged into this organ is liable to capture. Accordingly, it has become apparent that distal embolization presents a formidable threat.

One partial solution to the above-noted problems is disclosed in U.S. Pat. No. 4,794,928 to Kletschka. This angioplasty device incorporates a trap/barrier for trapping and removing particles that break away from the treatment sight. This device is desirable because it can prevent physiologically significant particles from escaping from the obstruction site, thus preventing the occurrence of unfavorable side effects from angioplasty treatment and procedures. One problem with this design, however, is that it is difficult to simultaneously provide an angioplasty device that is small enough to be used in very small and medium sized arteries, and/or in severely occluded vessels (i.e., vessels having a 90% or greater stenosis), and that has sufficient suction to remove the particulate matter.

Another partial solution to the above noted problems uses multiple catheters. These devices require that the doctor first deliver a "blocking" catheter to the target region such that its occlusion balloon is distal to the treatment site. The doctor then loads a second "balloon" catheter over the blocking catheter and performs the angioplasty procedure. The second catheter is then removed and a third catheter is loaded in its place over the blocking catheter. The third catheter can be used to aspirate blood from the treatment site. One problem with this design, however, is that it does not provide a means for capturing particles that are too large to fit within the suction lumen. Another problem is that this design requires a complex and relatively lengthy operational procedure, which can lead to neurological complications. In addition, particulate matter may also escape or be pulled from the treatment site when the catheters are switched and when the blocking balloon is deflated. Even when combined with suction, the risk exists that particles too large to be removed through the suction conduit will be delivered distally from the forward thrust of the blood flow as the blocking balloon is deflated.

Still another partial solution uses a porous hood that allows blood to pass. The hood, attached to the guidewire with struts, is held in a collapsed state within the angioplasty catheter. The hood deploys when pushed beyond the tip of the restraining catheter. Withdrawing the hood within the catheter closes the trap. These devices, however, do not provide suction and require multiple catheters. In addition, small particles may pass through the porous hood.

FIG. 1 illustrates the problems associated with obtaining the size of conduits necessary to do just the desired insertion, inflation, and suction tasks. FIG. 1 is a cross section of a five French catheter 10. A standard, 150 centimeter long, catheter may need a suction lumen 12 with a diameter of about 0.025 inches in order provide sufficient suction at its operational end to cope with debris released from a large atheromatous plaque. The catheter may also require an inflation/deflation lumen 14 with a diameter of about 0.015 inches to inflate an angioplasty balloon and a centered guidewire lumen 16 having a diameter of about 0.035 inches to position the device. As can be seen, these lumens significantly interfere with each other. An additional mechanism to open and close a blocking/capturing device will further encroach on allocatable space.

Clearly, there is a need for an improved angioplasty device for use in small diameter and/or severely occluded vessels that can prevent substantially all physiologically significant particles from escaping from the obstruction site, thus preventing the occurrence of unfavorable side effects from the angioplasty treatment and procedures. There is also a need for a small diameter angioplasty device that can provide aspiration, blocking, and capturing capabilities. In addition, there is a need for an improved particle trap that can prevent substantially all physiologically significant particles from escaping from the obstruction site and that can fit within, and be actuated by, a small diameter catheter bundle. There is also a need for an improved particle trap wherein the improved particle trap provides better maneuvering capabilities and more flexible navigation capabilities within vessels. There is a need for a method of making an improved particle trap with enhanced maneuvering capabilities. There is also a need for a trap with enhanced trapping capabilities for collecting and capturing particles while the trap is in the contracted position. There is a need for a handle device which operates to actuate the particle trap and which incorporates a locking mechanism for securing the particle trap in either the expanded or contracted position.

BRIEF SUMMARY OF THE INVENTION

The present invention provides an apparatus for use in angioplasty procedures or other medical, veterinary, non-medical or industrial applications where removal of an obstruction from a vessel or vessel-like structure could produce particles, which, if allowed to remain in the vessel, could cause undesirable complications and results. The present invention is particularly suited for use in small diameter vessels and/or in severely occluded vessels because it maximizes suction for a given catheter diameter. The present invention can also prevent substantially all physiologically significant particles from escaping from the obstruction site. Particles smaller than the width of the suction lumen are removed by aspiration in some embodiments, while the larger particles are captured beneath a contractible hood and removed when the catheter is withdrawn. Some embodiments also have a provision for aspirating debris generated as the angioplasty device is insinuated through a stenosis.

One aspect of the present invention is an angioplasty device for removing an obstruction from a vessel or vessel-like structure. One embodiment of this angioplasty device comprises a catheter for insertion into a vessel-like structure and a trap operably connected to the catheter and to a rotatable member, such as a fixed guidewire or a catheter forming a longitudinal axis, wherein a rotation of the rotatable member relative to the catheter actuates the trap. Some embodiments of this angioplasty device may also comprise a flexible strut fixedly connected to the catheter and to the trap. This flexible strut may expand and contract the trap by moving between a helically twisted position and an arcuately expanded position.

In one embodiment of the angioplasty device, the arcuately expanded position of the struts may form arcs that extend parallel to the longitudinal axis of the catheter or guidewire. In another embodiment, the expanded position of the struts forms arcs in a spiral configuration that circle the longitudinal axis of the catheter or guidewire. Other arcuately expanded positions of the struts are within the scope of this invention so long as the function of the trap is performed.

In one embodiment, the mid-section begins to close first to create a waist in the contracted trap. In this embodiment, the waist creates a pinch-point to enhance the trapping capabilities of the trap.

In another embodiment, one end of the trap is less resistant to closure than the other end of the trap, so that in contracting the trapping device, the less resistant section will close first. In this embodiment, the less resistant section will close tightly down while the other section will retain a small pocket. The overall profile of the contracted trap forms a cocoon-like structure in the shape of a teardrop.

Another aspect of this invention is a trap for selectively blocking a vessel or vessel-like structure. One embodiment comprises a rotatable member, such as a fixed guidewire or a catheter, that actuates a flexible strut between an arcuately expanded position and a helically twisted position, and a membrane operably connected to the flexible strut. These embodiments may further comprise a first ring that fixedly connects the rotational member to the flexible strut and a second ring that fixedly connects the flexible strut to a catheter. In addition, the proximal portion of the flexible struts can be inserted into the wall of the catheter in place of or in addition to the second ring.

Another aspect of the present invention are methods of making a particle trap adapted for removing an obstruction from a vessel-like structure. One embodiment comprises the acts of operably connecting a plurality of flexible struts to an outer surface of a catheter, the catheter containing a rotatable member; operably connecting the plurality of flexible struts to the rotatable member; and operably connecting a membrane to the plurality of flexible struts.

Another aspect of the present invention is a method of forming flexible struts for use in making the particle trap. In one embodiment a shape-memory alloy is used to form the struts in the steady-state expanded position. In another embodiment a polymer or plastic material is used to form the struts into the steady-state expanded position. The struts may be formed by fixedly attaching each end of the strut to a stationary device and shaping the struts over a molded device in the profile desired for the steady-state expanded position. The shape-memory alloy would then be treated so that it forms the profile of the molded device for its steady-state expanded position. In one embodiment, heat treatment is used to treat the metal to form the expanded profile. In one embodiment, the expanded spiral configuration is formed using a molded device in the desired profile wherein a portion of the molded device rotates to form a spirally twisted position of the expanded strut. The struts are then treated to form the spirally twisted position.

Another aspect of the present invention is a device for removing an obstruction from a vessel-like structure. One embodiment comprises a catheter for insertion into a vessel-like structure, the catheter having a catheter wall and a movable member, and a trap operably connected to the catheter wall and to the movable member. Relative motion between the catheter wall and the movable member actuates the trap. This relative motion may be a relative rotation or a relative translation.

In one embodiment, the angioplasty device comprises a handle fixed to the angioplasty device which the user manipulates to actuate the trap. The handle comprises a thumbwheel and a screw configuration enabling the user to actuate the trap from the contracted position to the expanded position. In one embodiment the handle comprises a lock for locking the trap in the desired position depending on the particular steps of the procedure. In these embodiments, the handle provides the necessary relative rotational or longitudinal or both movements to actuate the trap.

Another aspect is a catheter bundle for insertion into a vessel-like structure. The catheter bundle in this embodiment defines a balloon adapted to compress an obstruction against the vessel-like structure; a trap adapted to selectively block the vessel-like structure; an inflation lumen in operable communication with the balloon; and a suction lumen in operable communication with the trap. This catheter bundle has a diameter of less than about twenty French, with some embodiments having a diameter of less than about five French.

Another aspect of the present invention is a type of angioplasty procedure. One embodiment of this procedure comprises the acts of inserting a catheter into the vessel-like structure, the catheter including a trap and an actuator; positioning the trap in a downstream direction from an obstruction; moving the actuator in a first direction, thereby opening the trap; and moving the actuator in a second direction, thereby closing the trap. This procedure may further comprise the act of removing the obstruction from the vessel-like structure, thereby producing at least one particle. The at least one particle may be removed from the vessel-like structure using a suction lumen, the trap, or a combination thereof.

Three additional aspects of the present invention are a modular trap for an angioplasty device, a guidewire for use in a medical device, and an angioplasty device having a valve. One modular trap embodiment comprises a trap adapted to selectively block a vessel-like structure; and a coupling device that couples the trap to the angioplasty device. One guidewire embodiment comprises a guidewire wall defining a proximal opening, a distal opening, and an annular passageway, wherein the annular passageway fluidly connects the proximal opening to the distal opening. One angioplasty device embodiment with a valve comprises a first lumen, and a valve adapted to selectively block the first lumen.

Another aspect of the present invention is an apparatus for insertion into a vessel-like structure over a guidewire. One embodiment comprises a catheter for insertion into a vessel-like structure, the catheter having a catheter wall and a movable member, and a trap operably connected to the catheter wall and to the movable member, wherein relative motion between the catheter wall and the movable member actuates the trap. The catheter in this embodiment includes a guidewire lumen adapted to slideably receive the guidewire.

The present invention also includes a method of making an angioplasty device suitable for over the wire procedures. One embodiment comprises forming a catheter having a first wall and a second wall, operably connecting a plurality of flexible struts to the first wall, operably connecting the plurality of flexible struts to the second wall, and operably connecting a membrane to the plurality of flexible struts. The first wall in this embodiment defines a guidewire lumen and cooperates with the second wall to define a fluid communication lumen.

One or more of these embodiments may be used to remove an obstruction from a vessel-like structure by inserting the guidewire into a vessel-like structure; inserting a catheter into the vessel-like structure over the guidewire, the catheter including a trap and an actuator; positioning the trap in a downstream direction from an obstruction; moving the actuator in a first direction, thereby opening the trap; and moving the actuator in a second direction, thereby closing the trap.

One feature and advantage of the present invention is that it can provide a small diameter angioplasty device that can trap and remove substantially all physiologically significant particles. Another feature and advantage of the present invention is that it can provide aspiration, blocking, and capturing capabilities in a single catheter. Yet another feature and advantage is that the present invention maximizes the amount of suction per unit size, thus providing the doctor with more suction in larger vessels than presently available. These and other features, aspects, and advantages of the present invention will become better understood with reference to the following description, appended claims, and accompanying drawings.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 7A is a perspective view of an embodiment having a plurality of struts in a helically twisted position, with portions of the struts removed to show the inner catheter wall.

FIG. 7B is a side plan view of an embodiment having a plurality of struts in an arcuately expanded position.

FIG. 7C is a side plan view of an embodiment having a plurality of struts in an arcuately expanded position with the arcs forming a spiral configuration.

FIG. 7E is a side plan view of an embodiment having a plurality of struts in a contracted position wherein the contracted trap has formed a waist.

FIG. 10 is a detailed side plan view of an embodiment having a flexible membrane extension system.

FIGS. 12A and 12B are sectional views of an alternate valve embodiment.

FIG. 13 is a side plan view of an embodiment having separate catheters for the trap and the operative member.

FIG. 21 is a sectional view of a trap actuated by a relative translation, showing the trap in an arcuately expanded position.

FIG. 22 is a sectional view of the trap in FIG. 21, showing the trap in a contracted position.

FIGS. 33A-E are a sectional views of a trap and a profile device for forming expanded struts from a tube.

DETAILED DESCRIPTION

Figure 2:
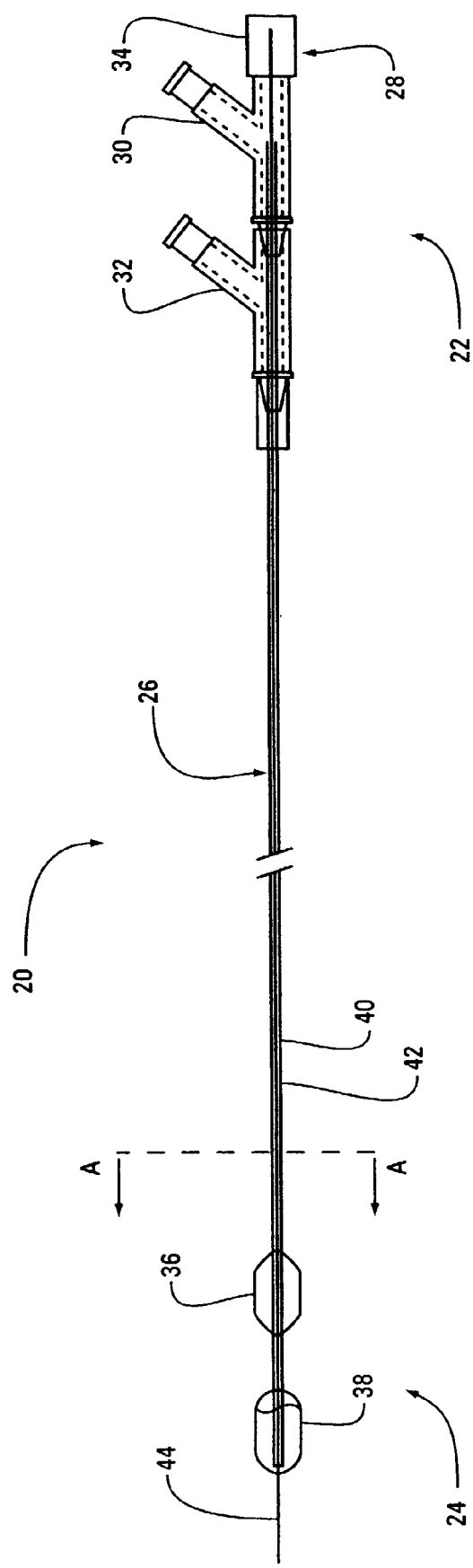
FIG. 2 is a side view of one embodiment of the angioplasty device of the present invention.

FIG. 2 is a side plan view of one embodiment of the angioplasty device 20 of the present invention. This angioplasty device 20 comprises a flexible catheter 26 having a proximal end 22, a distal end 24, and a generally circular cross section. The proximal end 22 of the catheter 26 is connected to a branched housing 28 that contains a suction port 30, an inflation port 32, and a guidewire port 34. The distal end 24 of the catheter 26 is connected to an angioplasty balloon 36, and a trap/barrier 38. As will be described in more detail with reference to FIG. 4, the flexible catheter 26 contains an inflation/deflation lumen 40, a suction/vacuum lumen 42, and a flexible guidewire 44.

In operation, distal end 24 of the angioplasty device 20 may be inserted into a vessel at any point in relation to the treatment site that is consistent with the desired treatment protocol. The balloon 36 is then aligned with the obstruction using methods known in the art, such as a radiopaque contrast solution, so that the trap 38 is situated in a position downstream from the obstruction site with the opening of the trap 38 positioned so that the fluid will flow into it and beneath the hood/membrane.

After positioning, the trap 38 may be expanded so that it forms a seal against the inner lining of the vessel. This seal will prevent physiologically significant particles from leaving the treatment site. A fluid, air, or other expansion medium may be then injected into the device 20 through the inflation port 32 and may be delivered through the lumen 40 to the balloon 36. The balloon 36 may then be expanded to perform its function. Alternatively, the balloon 36 and the trap 38 may be expanded simultaneously or the balloon could be expanded before the trap 38. As the balloon 36 is expanded, the obstruction is crushed against the inner diameter of the vessel, which increases the area through which fluid can flow. Crushing of the obstruction, however, creates particles that may break free on either side of the balloon 36.

When the vessel is living tissue (e.g., a human or animal vein, artery or duct) the balloon 36 may be inflated to a pressure ranging from approximately three to fifteen atmospheres, or more, depending on the application. The proper pressure will be dependant on the treatment protocol, the type of organism being treated, the type of vessel being treated and the material from which the balloon is constructed. Appropriate expansion pressures for a given situation will be known to those skilled in the art.

The balloon 36 may then be partially retracted so that a pressure differential between the vessel and the suction lumen 42 can draw any resulting particles toward the trap 38. Particles are either drawn into and through the catheter 26 or lodged in the trap 38 such that, when the trap 38 is retracted, the particles are trapped inside.

Figure 3A:
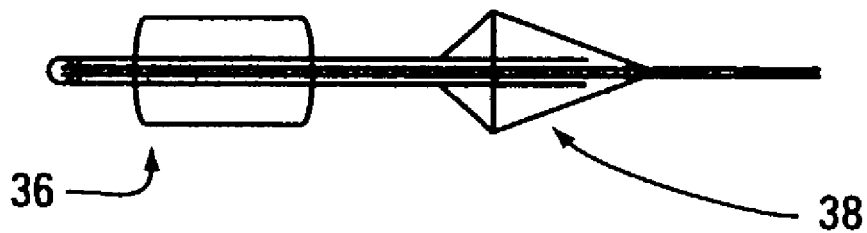
FIGS. 3A-3C are side plan views of different trap embodiments.
Figure 3B:
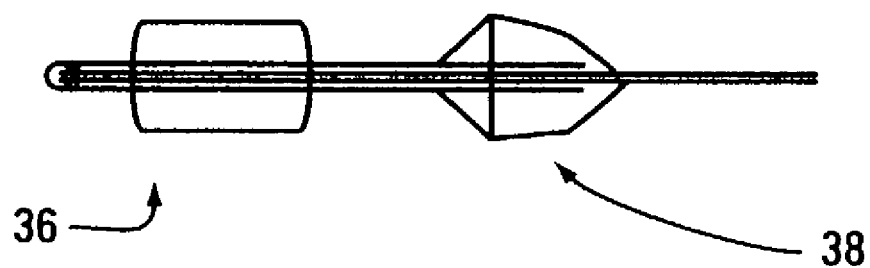
Figure 3C:
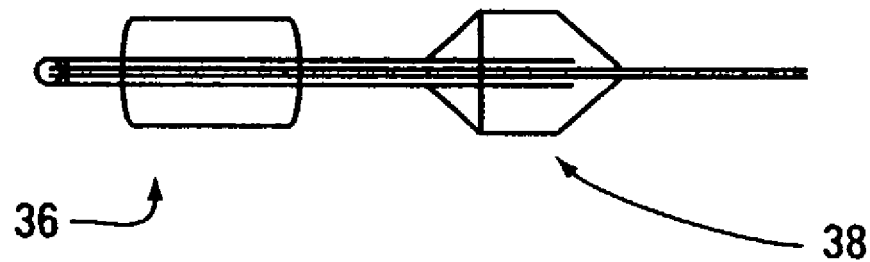

The trap 38 in this embodiment may assume any final shape as long as a substantial seal is achieved with the inner lining of the vessel to be treated and so long as the shape facilitates entrapment of the particles. FIGS. 3A-3C show three possible trap 38 embodiments. In particular, FIG. 3A shows a generally conically shaped trap 38, FIG. 3B shows a more or less "egg" shaped trap 38, and FIG. 3C shows a more or less oval shaped trap 38. Other trap 38 shapes and configurations are also within the scope of the present invention. In addition, the trap 38 and the balloon 36 may be situated with respect to each other in any configuration that allows the trap 38 to achieve a seal with the inner vessel lining and to trap particles when expanded. This includes, without being limited to, configurations in which the relative locations of the balloon 36 and the trap 38 are reversed. In contrast with the "antegrade" embodiments depicted in FIGS. 2 and 3A-3C, these "retrograde" embodiments would allow insertion of the angioplasty device from a point "downstream" from the treatment site.

Those skilled in the art will recognize that the balloon 36 in this embodiment serves as an operative member and may be replaced by any means known in the art, or later developed in the art, for removing or compressing an obstruction. Thus, as used throughout this specification and the claims, the terms "balloon" and "operative member" encompass any means for removing or compressing an obstruction, including but not limited to balloons, meshes, cutting rotors, lasers, treatment agents, and the means represented by U.S. Pat. Nos. 4,646,742, 4,636,195, 4,587,975, 4,273,128, 4,650,466, 4,572,186, 4,631,052, 4,589,412, 4,445,509, 4,641,912 and 4,576,177, the disclosures of which are incorporated herein by reference. Each type of operative member will have its unique control mechanism that, in the case of a balloon, fills it or, in the case of a laser or cutting rotor, turns it on. Furthermore, although the balloon and its associated filling or expansion system will be used throughout the specification as an example of an operative member and its associated control means, it is to be understood that any available operative member and its control means could be substituted in many of the embodiments discussed herein. Thus, references to "expansion" and "retraction" of the balloon should be understood, by inference, to refer to activating and deactivating whatever operative member is incorporated into a given angioplasty device 20.

Figure 4:
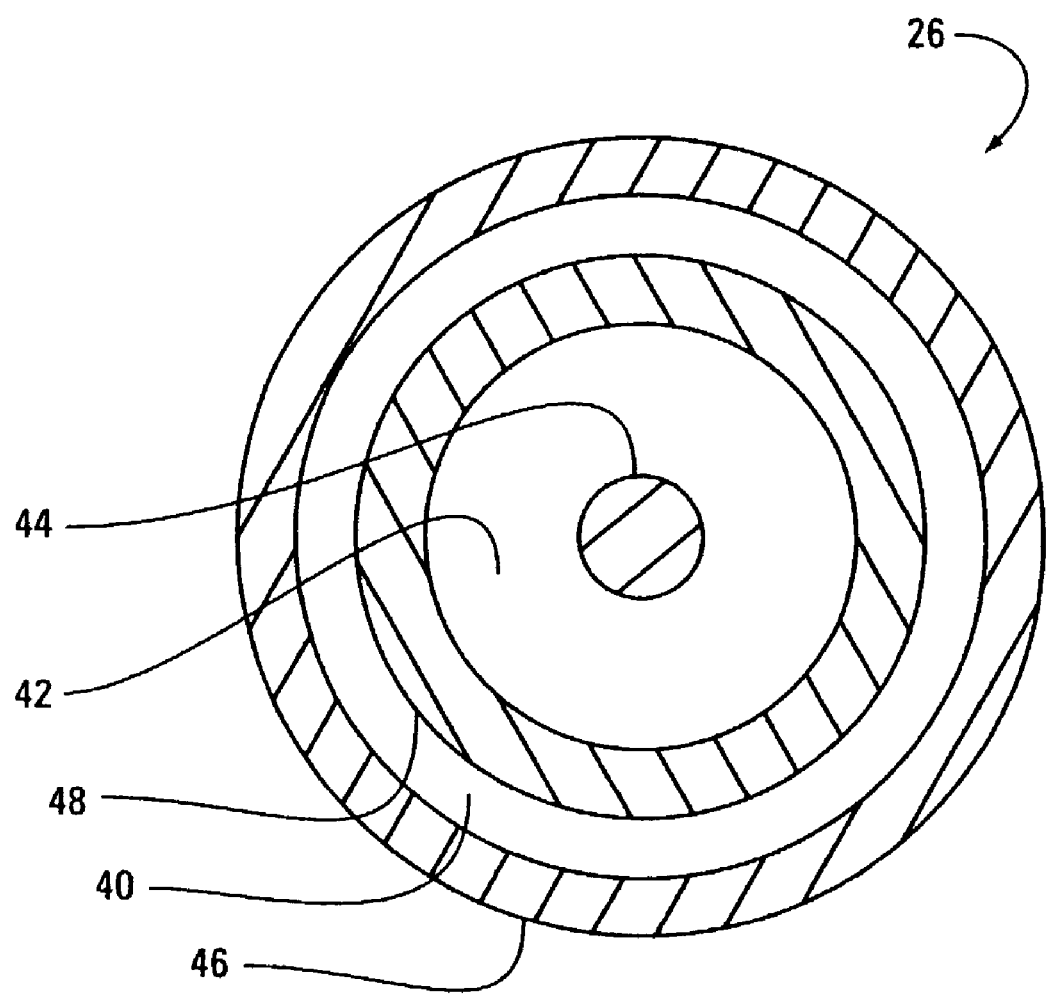
FIG. 4 is a sectional view of the embodiment depicted in FIG. 2 taken along the line AA.

FIG. 4 is a sectional view of the catheter 26 in FIG. 2 taken along line AA. The catheter 26 includes an outer wall 46, the inflation/deflation lumen 40, an inner wall 48, the suction lumen 42, and the guidewire 44.

The inner wall 48 and the outer wall 46 may be made from any relatively flexible material. When used in medical applications it is desirable, however, that the chosen material be approved for use in medical devices, be compatible with standard sterilization procedures, and be able to withstand the balloon's 36 inflation pressure without undue expansion in the radial direction. One suitable material is nylon. However, other wall materials are within the scope of this invention. In some embodiments, the inner wall 48 and the outer wall 46 comprise the same material. These embodiments may be desirable because they are generally easier to manufacture. However, embodiments where the inner wall 48 is made from a different material than the outer wall 46 are within the scope of this invention. In addition, the inner wall 48 may be reinforced in some embodiments with a metallic or plastic stent, strut, coil, or similar member, either in sections or for the full extent. These reinforcement members may also be embedded into the catheter wall.

The relative sizes and positions of the outer wall 46, the inflation/deflation lumen 40, the inner wall 48, the suction lumen 42, and the guidewire 44 are arbitrary. However, it is desirable to make the inflation/deflation lumen 40 and the suction lumen 42 as large as possible so that they can provide greater suction to the distal end 24, and ease of inflation and deflation of the angioplasty balloon (when that is the operative member). That is, the maximum vacuum that may be applied through the suction port 30 is limited by the wall materials. This maximum available vacuum is reduced by frictional losses between the proximal end 22 and the distal end 24. Because frictional loses in a closed channel are inversely proportional to the channel's cross sectional area, increasing the cross sectional area will increase the vacuum available at the distal end 24.

One method of increasing the cross sectional areas of the inflation/deflation lumen 40 and the suction lumen 42 is to make the outer wall 46, the inflation/deflation lumen 40, the inner wall 48, the suction lumen 42, and the guidewire 44 substantially coaxial. Coaxial arrangements can increase the available cross sectional area because, for a circle $dA/dr=2\pi r$. Thus, a lumen located near the outside of the catheter 26 will have a larger flow area than will a lumen that is located near the interior of the catheter 26, even if both lumens consume the same amount of distance between the walls. It was discovered that the increased flow area resulting from the coaxial arrangement can overcome its increased surface area.

Embodiments with coaxial lumens may be particularly desirable if the inner wall 48 helps to form both the inflation/deflation lumen 40 and the suction lumen 42. These embodiments are desirable because the catheter 26 only needs one internal structure to define two lumens. Despite these advantages, however, catheters having two or more inner walls are also within the scope of the present invention. These embodiments may be desirable because they can define additional lumens and can allow one suction lumen 42 to physically move relative to the other inflation/deflation lumen 40.

Accordingly, in one five French catheter 26 embodiment having the coaxial configuration shown in FIG. 4, the outer wall 46 has an outer diameter of 0.066 inches and an inner diameter of 0.056 inches; the inner wall 48 has an outer diameter of 0.0455 inches and an inner diameter of 0.0355 inches; and the guidewire 44 has an outer diameter of 0.012 inches. This provides a suction lumen 42 with a cross sectional area of about 0.0008 square inches. This embodiment is particularly desirable for use in carotid arteries procedures because it provides sufficient suction to remove the obstruction before complications occur and because it is small enough to fit within the artery. Smaller diameter catheters 26 (for example, between two and five French) having smaller suction lumens 42 may be suitable for use in less vital organs, where occlusion time limits are less critical, and in shorter catheters, where frictional losses are less significant. Larger diameter catheters 26 (for example, between five and forty French) having larger suction lumens 42 may be desirable for use in larger arteries, such as the aorta or iliacs, to accommodate the larger blood flow rate, and in longer catheters.

Figure 5:
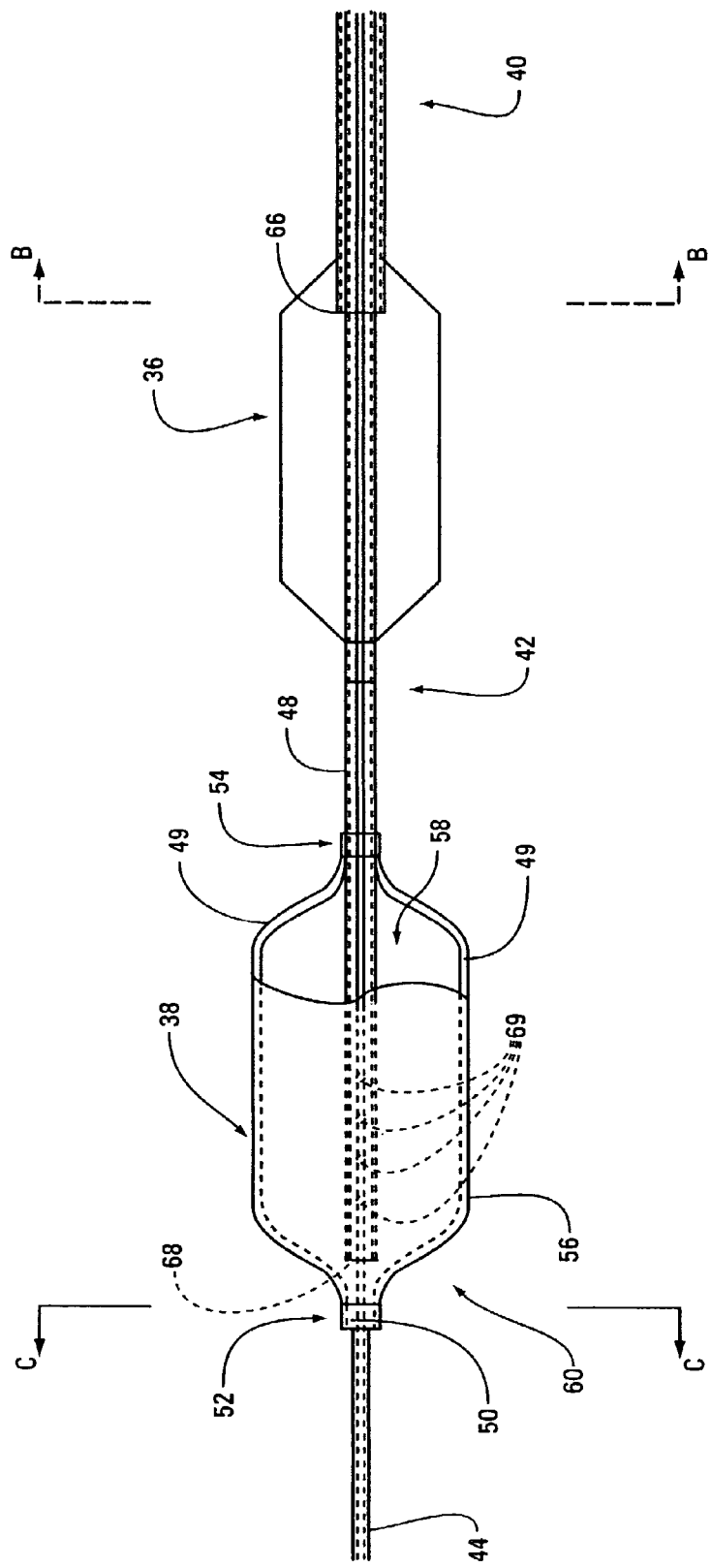
FIG. 5 is a side view of the distal end of the embodiment depicted in FIG. 2.
Figure 28:
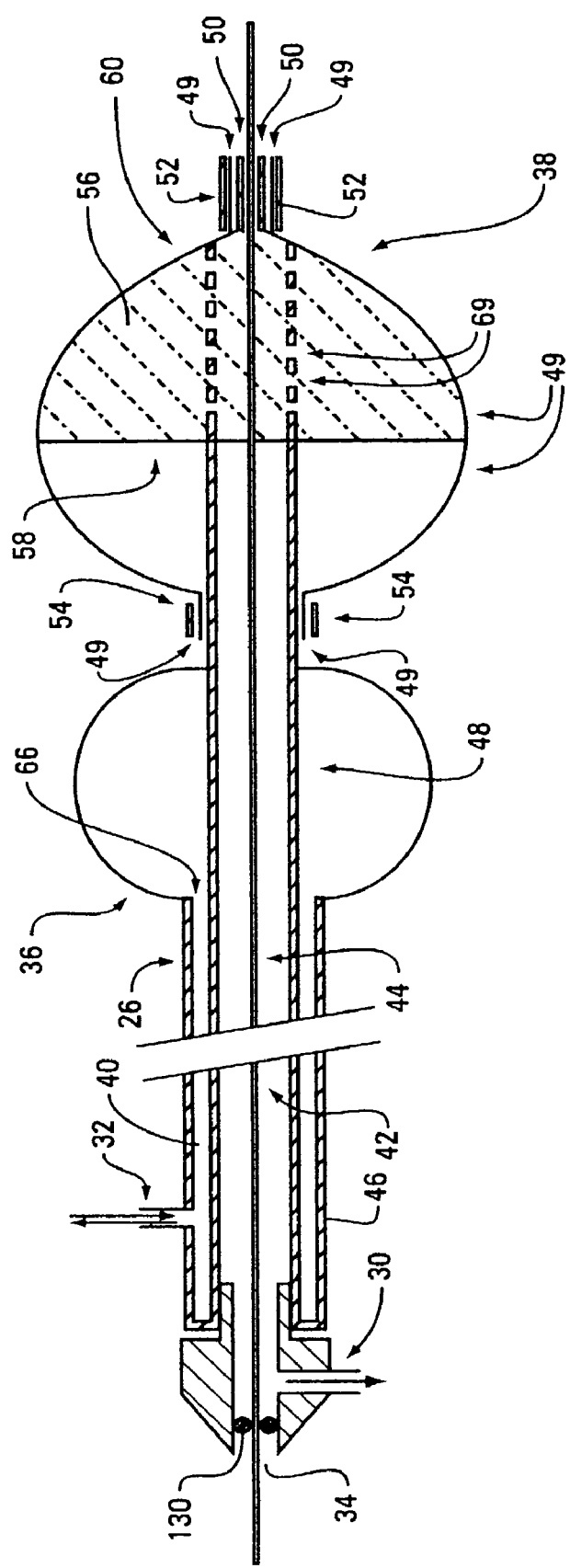
FIG. 28 is a sectional view of the angioplasty device in FIG. 5.

FIGS. 5 and 28 are more detailed views of the distal end 24 of the embodiment in FIG. 2. FIGS. 5 and 28 show that the inflation/deflation lumen 40 (see also FIG. 4) terminates in an opening 66 located inside the balloon 36. This opening 66 allows air, saline solution, or some other inflation medium, to fill the balloon 36 and to bias it radially outward against the obstruction. Similarly, the suction lumen 42 (see also FIG. 4) terminates at a single opening 68 and/or a plurality of pores 69 that are spaced along its length and around its perimeter. These openings 68 and/or pores 69 are used to remove smaller particles from the treatment site and to suck larger particles into the trap 38. Embodiments in which the inflation/deflation lumen 40 terminates immediately at the proximal end of the balloon 36 may be particularly desirable because this minimizes the profile of the balloon 36 in its contracted configuration.

Figure 29:
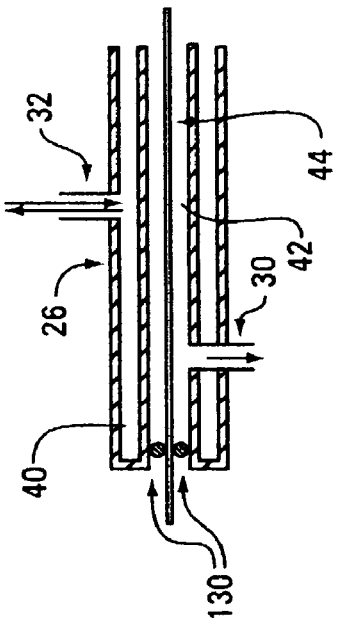
FIG. 29 is a detailed sectional view of an alternate proximal end embodiment.

FIGS. 5 and 28 also show that the trap 38 in this embodiment comprises a plurality of flexible struts 49 in an arcuately expanded position. In one embodiment, these struts 49 are fixedly attached to the guidewire 44 by an inner stainless steel ring 50 and outer stainless steel ring 52, and to the exterior surface of the interior wall 48 by a stainless steel ring 54. A flexible membrane 56 having an open end 58 and a closed end 60 is attached to a distal portion of the struts 49. FIG. 29 shows an alternate embodiment in which the branched housing 28 in FIGS. 5 and 28 has been eliminated, with the guidewire going through an O-ring seal 130 in the catheter's proximal end and an integral suction port in direct fluid communication with the suction lumen.

The plurality of flexible struts 49 and the flexible membrane 56 combine to form the trap 38. In some embodiments, flexible struts 49 are longer than the distance between the rings 50, 52 and the ring 54. This causes the flexible struts 49 to function like a single-leaf semi-elliptic beam spring when in their arcuately expanded position.

The open end 58 of the flexible membrane 56 is attached to the flexible strut 49 near the area of maximum axial extension. However, the membrane 56 could also be attached proximally or distally to the maximum extension point. The closed end 60 of the flexible membrane 56 is attached to one of the rings 50 and 52. The flexible struts 49 are preferably radially spaced around the catheter 26 so that they can evenly bias the membrane 56 radially outward into contact with an interior wall of a vessel or vessel-like structure.

In other embodiments, the struts 49 circle the guidewire or catheter and form a spiral configuration when in the expanded position, as shown in FIG. 7C. Flexible spiral struts 49 may be formed so that the steady-state position is the spiral-shaped position of the trap. In these embodiments, the steady-state expanded position of the struts 49 forms a side profile that may be either symmetrically shaped or asymmetrically shaped. In one embodiment, the profile 560, shown in FIG. 7C is asymmetrical with a first end 561 having a larger radius of curvature 564 than a second end 562 with a smaller radius of curvature 565. In one embodiment, the larger radius of curvature is 0.625 inches while the smaller radius of curvature is 0.250 inches. In this embodiment, the ratio of larger radius of curvature to smaller radius of curvature is 2.5:1. Other embodiments may have different radii of curvature and different ratios. In a symmetrical profile the radii of curvature are equal.

In the embodiment depicted in FIG. 7C, the flexible membrane 56 is attached to the distal end of the trap 38 and to the guidewire 44 by a distal connection, which in this embodiment is rings 50, 52. The flexible membrane 56 has an opening 58 at the area of maximum radial extension of the spiral-shaped strut 49. The opening allows the membrane to collect particles.

In the embodiment shown in FIG. 7C, rings 50 and 52 fixedly attach the distal end of the flexible struts 49 to the guidewire 44. In another embodiment, only one ring is used to fixedly attach the distal end of the flexible struts 49 to the guidewire 44. Similarly, ring 54 fixedly attaches the proximal end of the flexible struts 49 to the exterior surface of the catheter's inner wall 48.

Rotating the guidewire 44 relative to the catheter 48 will cause the struts 49 to move between the helically twisted (or "braided") position shown in FIG. 7A and the arcuately expanded position shown in FIG. 7B. Rotating the guidewire 44 causes the distal end of the struts 49 to rotate relative to the proximal end. This, in turn, forces the struts 49 to wrap around the inner wall 48 of the catheter 26. Continued rotation of the guidewire 44 will continue to draw the struts radially inward until they lie adjacent to the inner wall 48 of the catheter 26.

In embodiments with spiral shaped struts, shown in FIG. 7C, the expanded position comprises struts 49 that circle around a central longitudinal axis 561 of the device to form a spiral shaped configuration. Rotating the guidewire 44 relative to the inner wall 48 of the catheter 26 will cause the struts 49 to move between a helically twisted (or "braided") position shown in FIG. 7A and a helically expanded position shown in FIG. 7C wherein the expanded struts form a spiral configuration. To contract the trap 38 following deployment, the guidewire 44 is moved relative to the inner wall 48 of the catheter 26 to actuate the trap 38.

In some embodiments, the struts 49 have generally uniform physical characteristics, such that when a torsional force is applied to the struts, the mid-section of the trap 38 tends to close down around the catheter 26, forming a waist 43 in the contracted trap 38. The waist 43 creates a pinch-point to further trap particles. When the trap is closed by applying both a rotational motion and a longitudinal motion, the formation of the waist 43 will not occur so long as sufficient longitudinal extension of the trap 38 is effected. In one embodiment, the further facilitate formation of the waist 43, the mid-section of the struts 49 is formed to have less resistance to closure, using one of the techniques outlined herein.

Figure 7D:
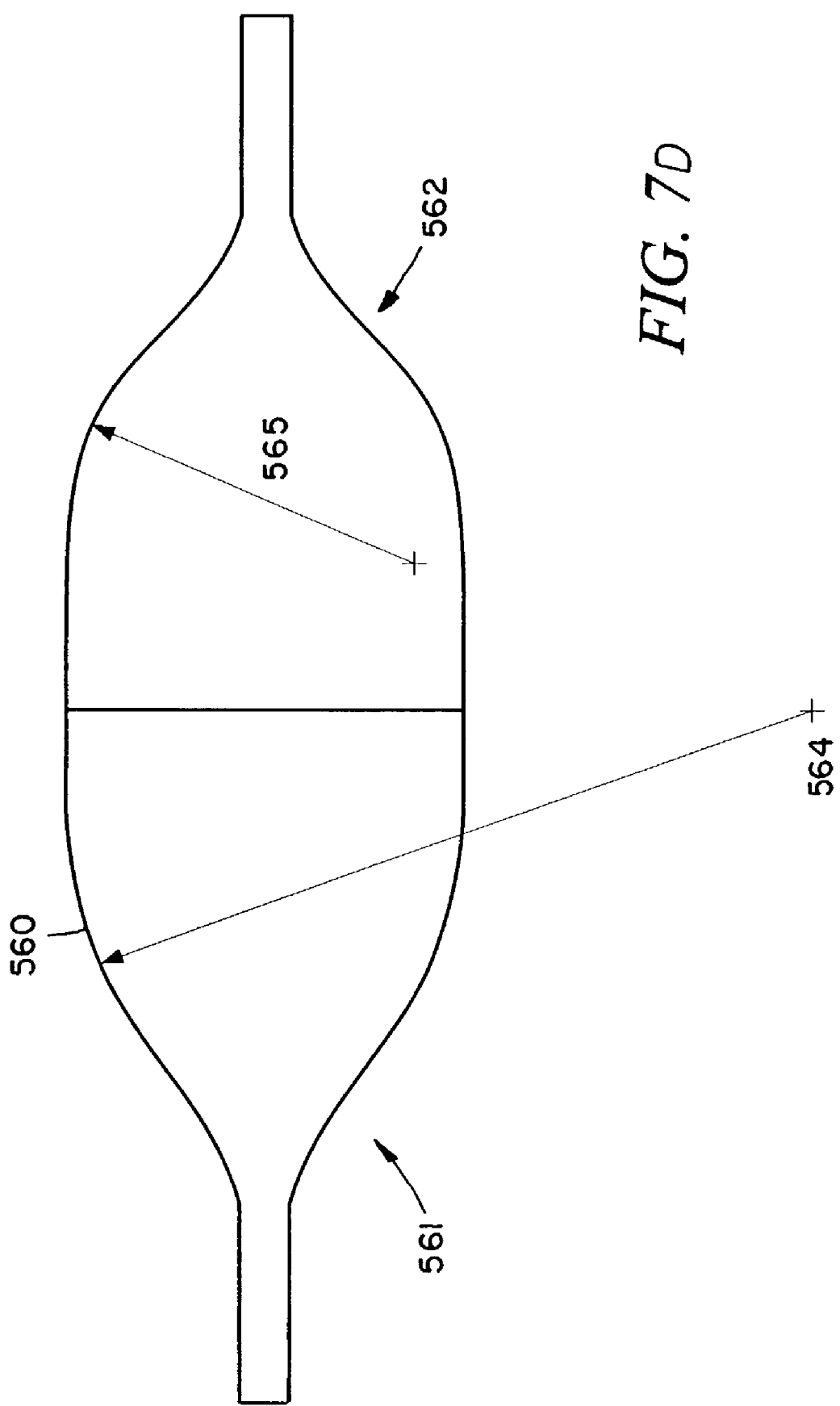
FIG. 7D is a side plan view of an embodiment of a profile devices.
Figure 7F:
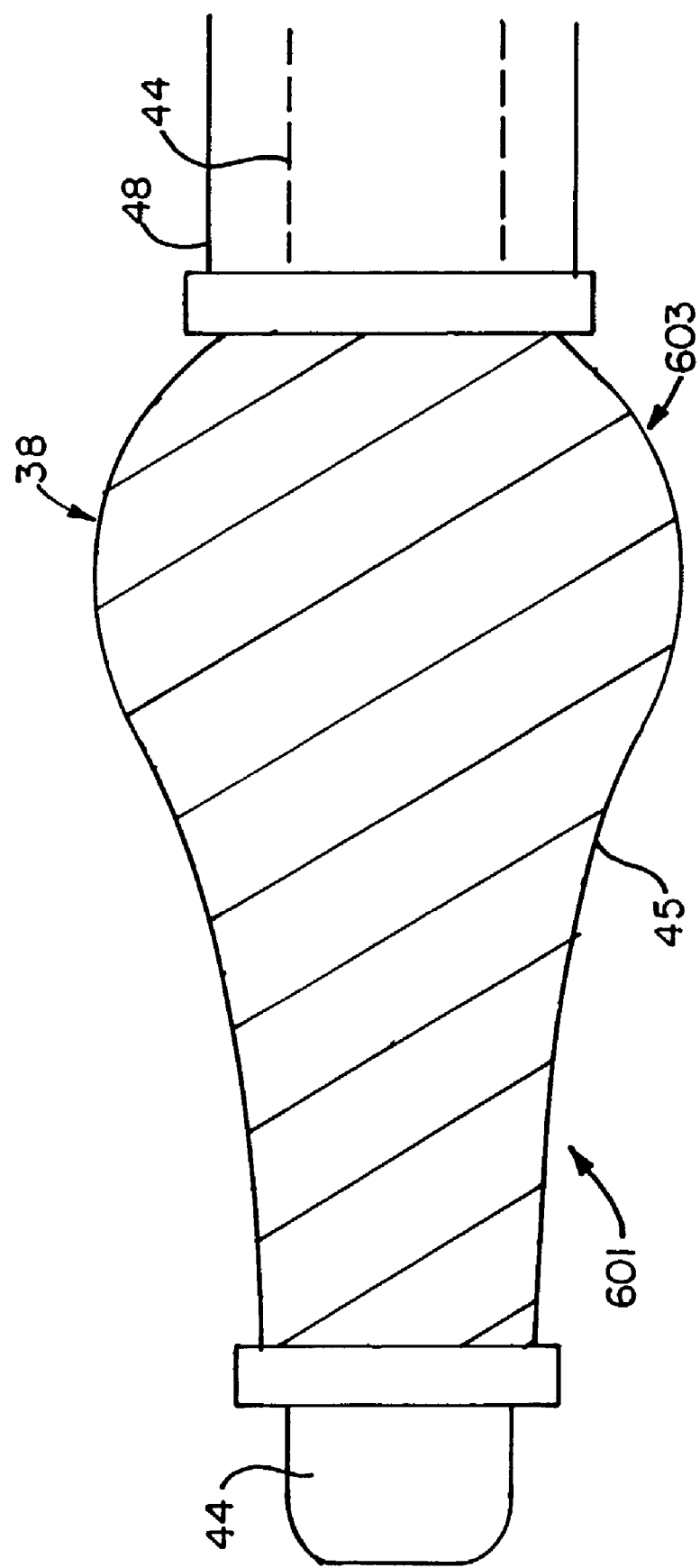
FIG. 7F is a side plan view of an embodiment having a plurality of struts in a contracted position wherein the contracted trap has formed a cocoon.

In some embodiment, FIG. 7F a first end of the trap 38 is constructed to be less resistant to closure than the second end of the trap 38, so that when the trap 38 is contracted, the first end will close first. When the first section closes first, that portion 601 of the struts tightly contracts towards the guidewire 44 while for the second section, that portion 603 has a tendency to not completely contract. The profile of the contracted trap 38 forms a cocoon 45 structure with one end having a bulge 603 that gradually tapers to be tight against the guidewire 44. This embodiment enhances trapping capabilities because the bulge 603 creates a pocket to hold particles that were not removed by suction. Having the bulge 603 is desirable because this section is not squeezed, and squeezing may cause particles to be pushed out of the membrane. Also this embodiment enhances trapping capabilities because the section 601 tight against the guidewire creates a pinch so that particles remain within the trap until the device 20 is removed from the lumen.

Figure 7G:
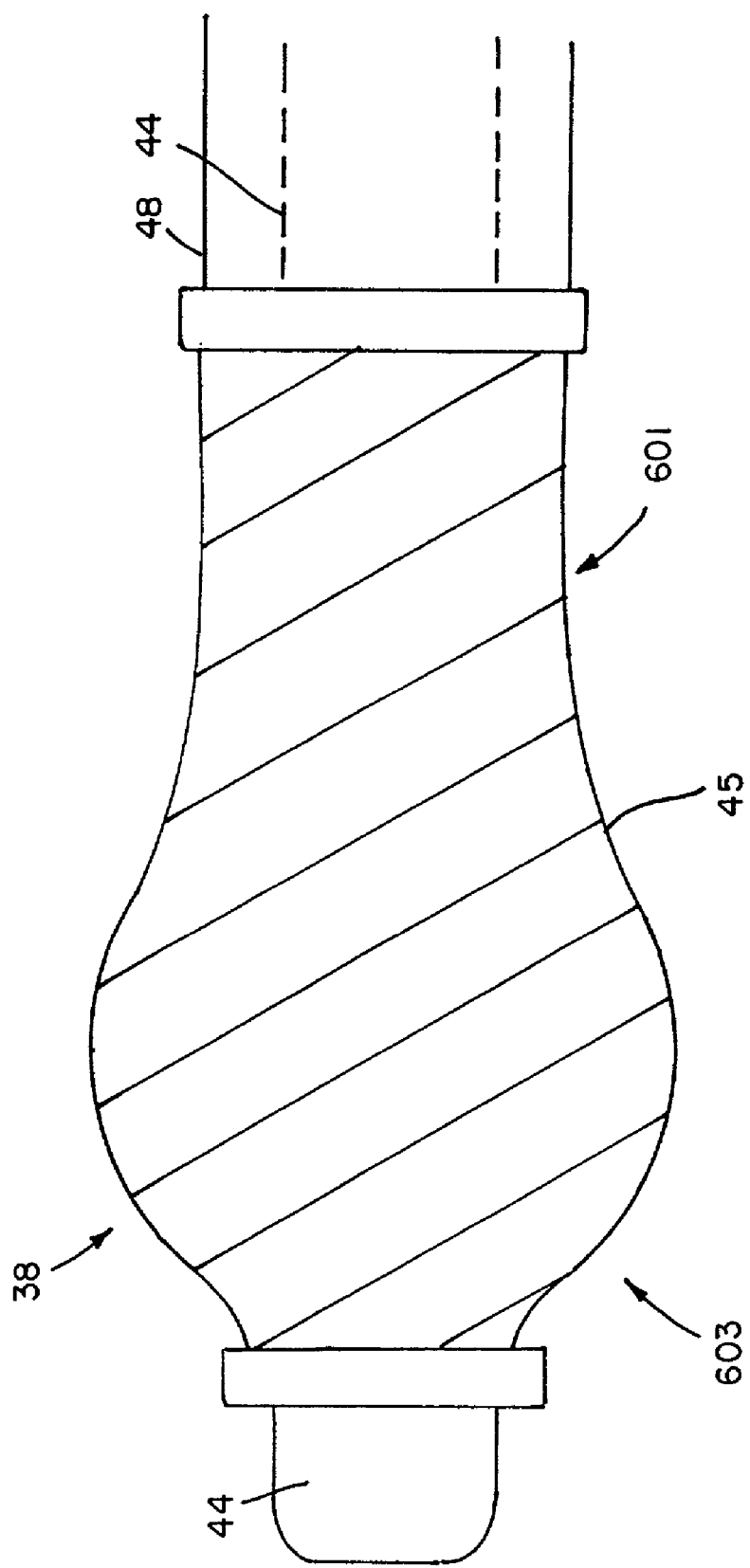
FIG. 7G is a side plan view of an embodiment having a plurality of struts in a contracted position wherein the contracted trap has formed a cocoon.

FIG. 7G also depicts a cocoon structure 45 with a bulge 603 that gradually tapers to be tight against the guidewire 44. This embodiment corresponds to FIG. 7C with the flexible membrane 56 located at the distal portion of the trap 38. The bulge 603 comprises the flexible membrane 56 in the contracted position. The tapered portion 601 of the contracted trap comprises the opening 58 of the flexible membrane 56. The tapered portion 601 lies tightly against the guidewire 44 to trap particles within the flexible membrane 56. The bulge 603 prevents particles from being squeezed from the flexible membrane 56 during contraction of the trap 38.

To construct one end of the trap 38 as less resistant than another end, in one embodiment where the profile 560 of the trap 38 is asymmetrical, the end of the trap 38 with the largest radius of curvature will close first when rotated to the contracted position because it requires more force to close the end with the smaller radius of curvature. Therefore, as depicted in FIG. 7D, the larger radius of curvature 564 for the first end 561 will cause the first end 561 to close first when the trap is contracted. The second end 562 with the smaller radius of curvature 565 will close after the first end 561 begins to close.

In one embodiment, the cocoon 45 is formed during contraction of the trap 38 because a portion of the struts 49 between the membrane 56 and the proximally-located ring 54 is thinner than a portion of the struts 49 beneath the membrane 56. The thinner struts require less force to contract and therefore close first. In another embodiment, the cocoon 43 is formed because the portion of the struts 49 between the membrane 56 and the proximally-located ring 54 is more resilient than the portion of struts 49 beneath the membrane 56. In this embodiment, a more resilient strut 49 may be made from a different material having a different elasticity. The end of the trap 38 having the larger radius of curvature, the thinner struts, or the more resilient material will close first. In another embodiment, a first portion of the struts 49 is constructed with a cross-section having a first moment of inertia and a second portion of the struts 49 is constructed with a cross section having a second moment of inertia. In this embodiment, the section with the smaller moment of inertia will close first. In one embodiment according to the present invention, the membrane 56 covers the portion of the struts 49 having the greater resistance to closing. In one embodiment, the membrane 56 covers the portion of the struts 49 having the greater resistance to closing and partially covers the portion of the struts 49 having less resistance to closing to enhance the ability of the membrane 56 to trap embolic particles.

A membrane 56 may also be attached to the struts 49. The struts 49 may be evenly spaced from one another to create maximum support for the membrane 56 forming the trap 38. The spiral configuration may enhance maneuverability within the vessel, because the gaps between the struts 49 allow for partial side-to-side and up-and-down movement without buckling the strut 49. Accordingly, the spiral struts 49 are adapted to be expanded in a curved portion of a lumen.

In one embodiment, the guidewire 44 is rotated and longitudinally extended to cause rotation and translation of the distal section of the trap 38 to prevent the membrane 56 from collapsing on itself in the contracted position.

Rotating the guidewire 44 in the opposite direction will cause the struts 49 to untwist, which allows the struts 49 to move back to the arcuately expanded position shown in FIG. 7B. This, in turn, expands the trap 38. In other embodiments, rotating the guidewire 44 in the opposite direction will cause the struts 49 to return to its expanded position which allows the struts 49 to form the spiral configuration shown in FIG. 7C, expanding the trap 38.

Figure 32:
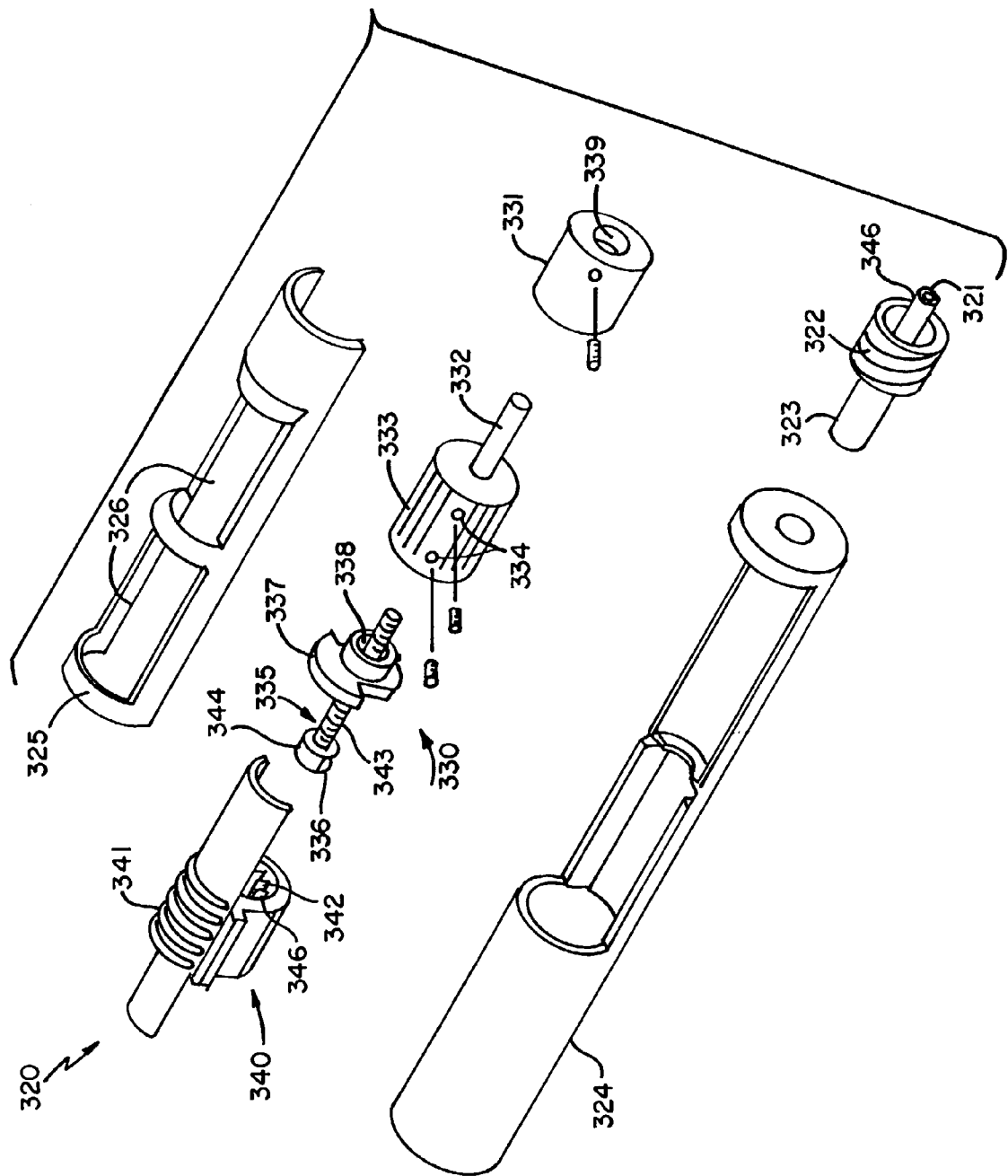
FIG. 32 is an assembly view of the handle.

To actuate the trap 38 using rotational or longitudinal or both movements, some embodiments of the present invention are equipped with a handle 320 as depicted in FIG. 32. The handle 320 comprises a main body 324 and cover 325, a screw configuration 330, and in some embodiment a locking device 340.

In one embodiment, the main body 324 and cover 325 comprise a generally cylindrical shape to comfortably fit the user's hand during the procedure and are hollow to house the screw configuration 330 and locking device 340. In addition, the cover 325 comprises openings 326 where a thumbwheel 333 and a slide lock 341 are accessible to the user to operate the device.

The screw configuration 330 provides the rotational or longitudinal or both types of movement to actuate the trap 38. The screw configuration 330 comprises a luer 322, a ferrule 331, a thumbwheel 333, a drive screw 335, and a stationary insert 337. The luer 322 is located at the distal end of the main body 324. The luer 322 is located external to the main body 324 with a cylindrical portion 323 entering into the main body 324. The luer 322 is a generally cylindrical device which provides a connection device 346 to connect the inner catheter 48 to the handle 320 and hold it stationary. The connection device 346 may be a threaded section to mate with a threaded section of the inner catheter. The luer 322 comprises an inner opening 321 for the guide wire 44 to enter through to connect to the thumbwheel 333.

The ferrule 331 provides a stop for the screw configuration. The ferrule 331 is a generally cylindrical device with an inner opening 339 for an extension 332 of the thumbwheel 333 to enter through to connect to the guidewire 44. The ferrule 331 is slidable along the thumbwheel extension 332. The ferrule 331 is provided so the screw configuration 330 will not deploy the trap 38 beyond a predetermined maximum extension point.

The thumbwheel 333 is a generally cylindrically shaped device and is rotatable and controlled by the user. The thumbwheel extension 332 is a rigid extension of the thumbwheel 333 and protrudes from the distal end of the thumbwheel 333. The guidewire 44 is rigidly connected to the thumbwheel extension 332 so that rotation of the thumbwheel 333 causes the guidewire 44 to rotate relative to the stationary outer catheter 148, 46. Rotation of the guidewire 44 relative to the stationary inner catheter 48 actuates the trap 38. The thumbwheel 333 comprises openings 334 in which a connection device is used to rigidly connect the thumbwheel 333 to the drive screw 335.

The drive screw 335 is used to provide longitudinal movement to actuate the trap 38. The drive screw 335 comprises a threaded surface 343 and a head portion 344 with notches 336 for locking with a slidelock 341. The notches 336 may be in the form of a linear protrusion on the surface of the head portion 344 which would match with an indented portion on the slidelock 341.

The stationary insert 337 is rigidly connected to the main body 324 of the handle 320. The stationary insert 337 contains an opening 338 through which a drive screw 335 enters. The opening 338 comprises a threaded surface to mate with the threaded surface 343 of the drive screw 335. Because the stationary insert 337 is rigidly connected to the main body 324, but the drive screw 335 is freely movable, rotation of the thumbwheel 333, which is rigidly connected to the drive screw 335, causes longitudinal, rotational or both types of movement of the drive screw 335, thumbwheel 333 and therefore the guidewire 44.

In embodiments with the handle and screw configuration, the longitudinal movement generated by the drive screw 335 is transferred to the guidewire 44. When the trap 38 is expanded, the guidewire 44 rotates and also longitudinally decreases the distance between the connection rings 50,52 and 54. When the trap 38 is contracted, the guidewire 44 rotates and also longitudinally increases the distance between the connection rings 50, 52 and 54. The ratio of longitudinal motion to rotational motion is controlled by altering the pitch of the drive screw 335.

The locking mechanism 340 comprises a slidelock 341 which slidably engages with the screw head 344 to lock the screw 335 from further movement. The locking mechanism 340 comprises an internal locking wheel 342 with indented portions 346 to engage with the protrusions 336 on the drive screw head 344. The slidelock 341 is slidably connected to the main body 324 so that only linear movement of the slidelock 341 is allowed. Therefore, when the slidelock 341 is shifted in the distal direction to engage with the screw head protrusions 336, the drive screw 335 is also prevented from rotational movement. Because the drive screw 335 is rigidly connected to the thumbwheel, which is in turn is rigidly connected to the guidewire 44 or inner catheter 48, 302, none of these components are allowed to move either, thus locking the trap 38.

The threaded sections 343 of the drive screw 335 comprises a pitch so that with each rotation, the drive screw moves in a longitudinal direction. The longitudinal movement along with the rotational movement is transferred to the distal end of the trap 60. The rotational movement actuates the trap to the expanded or contracted position. The longitudinal movement causes the guidewire 44 to move in a longitudinal direction. The distance between the strut attachment points 50, 52 and 54 is increased when the trap is contracted. This increased distance helps prevent the trap 38 from collapsing and bunching over itself in the contracted position.

In one embodiment, the guidewire 44 is a catheter or any other movable member. In this embodiment, the distal end of the struts 49 would be attached to the inner catheter and form the movable member while the proximal end of the struts would attach to the outer catheter and form the stationary member. A slideable guidewire may then pass through the inner catheter. It is understood that in one embodiment to actuate the trap one end of the trap is connected to the movable member while the other end of the trap is connected to the stationary member. The handle may be used to actuate the trap with any combination of guidewires and catheters, so long as the function of actuating the trap is accomplished.

Figure 8:
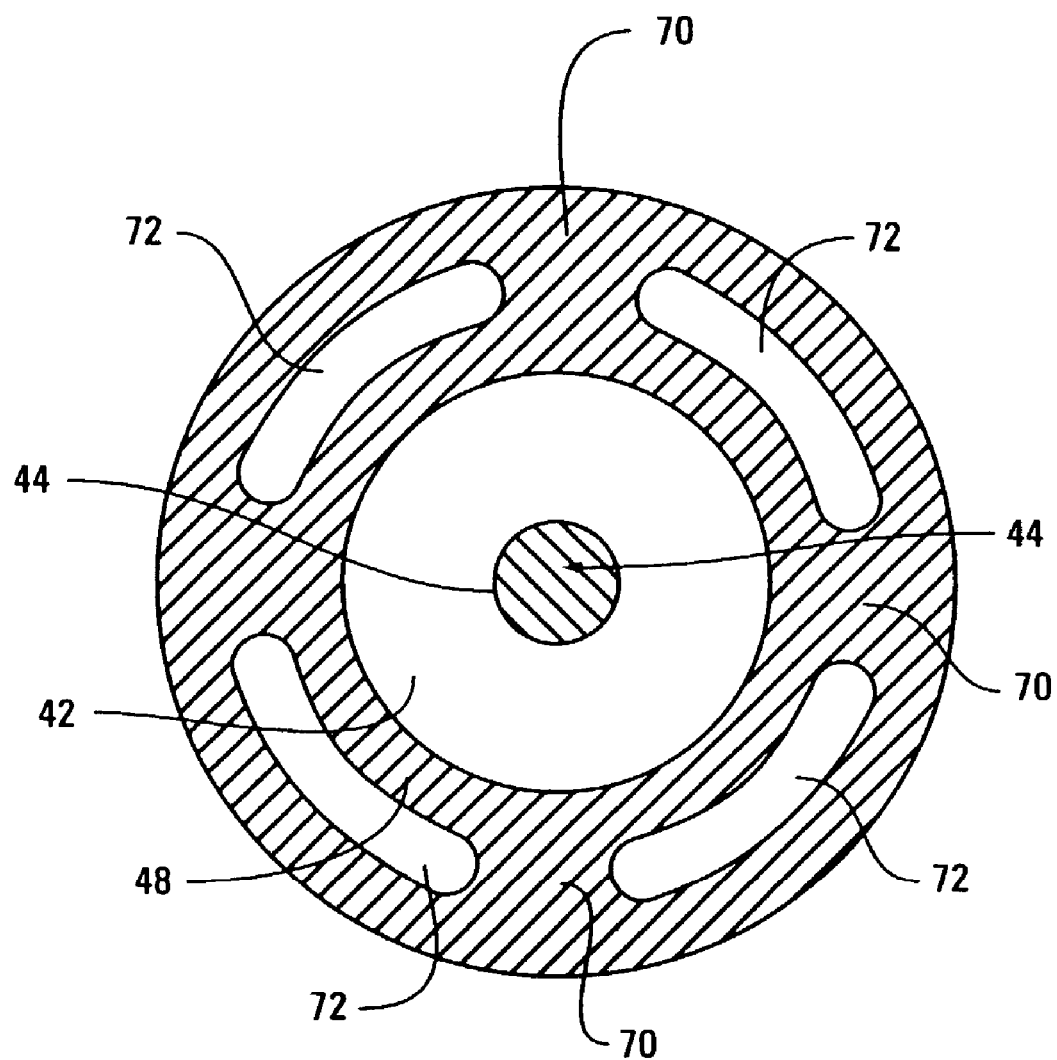
FIG. 8 is a sectional view of a stiffener, taken along the line BB.

FIG. 8 is a sectional view of the angioplasty device 20 in FIG. 5 taken along the line BB. This figure shows four optional stiffening members 70 that connect the inner wall 48 to the outer wall 46. These stiffening members 70 define a plurality of openings 72 that keep the inflation/deflation lumen 40 (see FIG. 4) fluidly connected to the balloon 36 (see FIGS. 5 and 28). These stiffening members 70 are desirable because they give the user something to "push against" when actuating the trap 38. That is, a user expands and contracts the trap 38 (see FIGS. 5 and 28) by rotating the guidewire 44 around its longitudinal axis. The torque used to rotate the guidewire 44 is transferred to the inner wall 48 through the struts 49, which causes the inner wall 48 to twist. The stiffening members 70 couple the inner wall 48 and the outer wall 46. The combined torsional stiffness (or perhaps more accurately, the combined polar moment of inertia) of the inner wall 48 and the outer wall 46 is greater than that of the inner wall 48 alone. In this embodiment, the stiffening members 70 may extend throughout the length of the catheter 26 or may only extend a short distance from the opening 66.

Figure 9B:
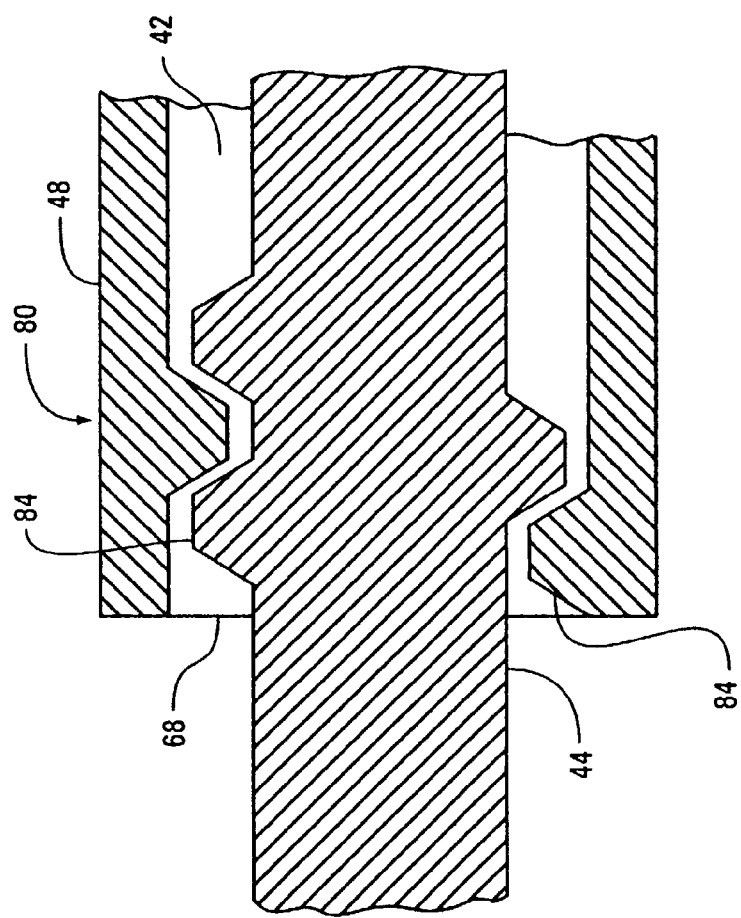
FIGS. 9A and 9B are a sectional view and a side plan view of an embodiment having a screw extension system.
Figure 9A:
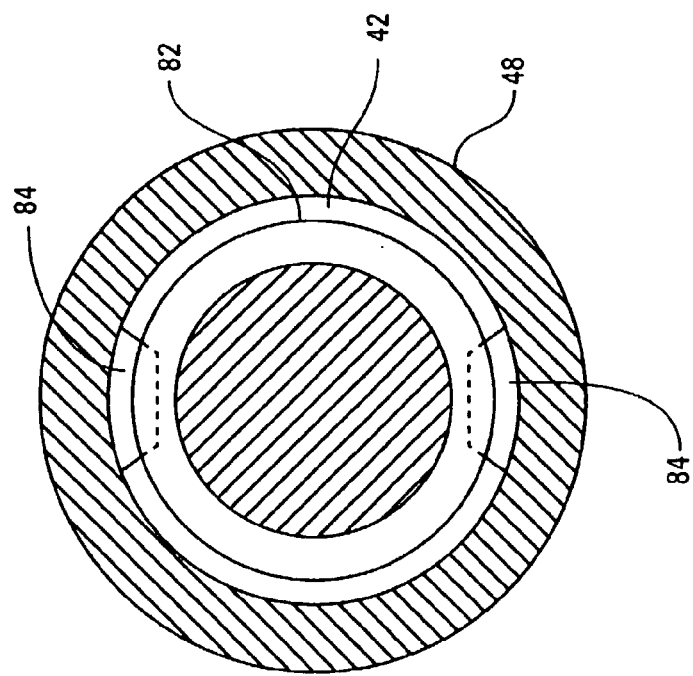

FIGS. 9A and 9B are side plan and sectional views of an angioplasty device 20 having a screw extension system 80 located near the distal end of the suction lumen 42. However, screw extension systems 80 located in other locations, such as within the housing 28, are also within the scope of the present invention. The screw extension system 80 in this embodiment comprises a helical screw thread 82 attached to the guidewire 44 and a pair of offset studs 84 attached to the inner wall 48. The offset studs 84 engage the helical screw thread 82 without blocking the suction lumen 42, which causes the guidewire 44 to move axially inside the suction lumen 42 when rotated. Embodiments having this screw extension system 80 are desirable because it increases the distance between the distal rings 50 and 52 and the proximal ring 54 (see FIGS. 5 and 28), which helps the struts 49 to contract into an orientation that is smooth and tight against the guidewire 44.

FIG. 10 shows a flexible membrane extension system 80a that may be used in place of or in conjunction with the screw extension system 80 of FIGS. 9A and 9B. FIG. 10 depicts the proximal end of the guidewire port 34, which comprises a generally cylindrical housing 86 and a generally cylindrical lumen 87 that is fluidly connected to the suction lumen 42 (see FIG. 4). The guidewire 44 runs through the lumen 87 and is connected to a disk shaped handle 88. FIG. 10 also depicts a flexible membrane 89 that is attached to the housing 86 and to the handle 88.

As described with reference to FIGS. 7A, 7B, 7C, 7E and 7F, the user expands and contracts the trap 38 by rotating the guidewire 44 around axis ZZ (see FIG. 10). The guidewire 44, in turn, may be rotated by manually turning the handle 88. Because the membrane 89 is fixed to both the housing 86 and the handle 88, however, this rotation causes the membrane 89 to twist. This twisting motion causes the membrane 89 to bunch together, which pulls the handle 88 in a distal direction towards the housing 86. The handle 88, in turn, pushes the guidewire 44 through the catheter 26.

Embodiments using the flexible membrane extension system 80a in FIG. 10 are desirable because the membrane 89 longitudinally biases the proximal ring 54 relative to the distal rings 50 and 52, thereby helping to actuate the trap 38, and because the membrane 89 helps to seal the suction lumen 42. Preferably, the membrane 89 will comprise materials and dimensions such that 25 the amount of rotation necessary to actuate the trap will also produce the desired longitudinal motion. Other extension systems 80, such as a spring or other elastic member located between the handle 88 and the housing 86, and other sealing systems, such as a membrane 89 that completely surrounds the handle 88, an O-ring, or a wiper style seal, are also within the scope of the present invention.

Referring again to FIG. 5 and 28, the struts 49 may be made from any elastic material. It is desirable, however, that the material be approved for use in medical devices when used in medical applications, have a relatively high modulus of elasticity, and have a relatively good resilience. One particularly desirable class of materials are "shape memory alloys," such as Nitinol®. These materials are desirable because they can be easily "taught" a shape to which they will return after having been deformed. Manufacturers can use this feature to form struts 49 that will naturally return to their arcuately expanded position when a user releases the guidewire 44. Despite these advantages, however, other strut materials are within the scope of the present invention. This specifically includes, without being limited to, stainless steel and polymers.

Figure 31:
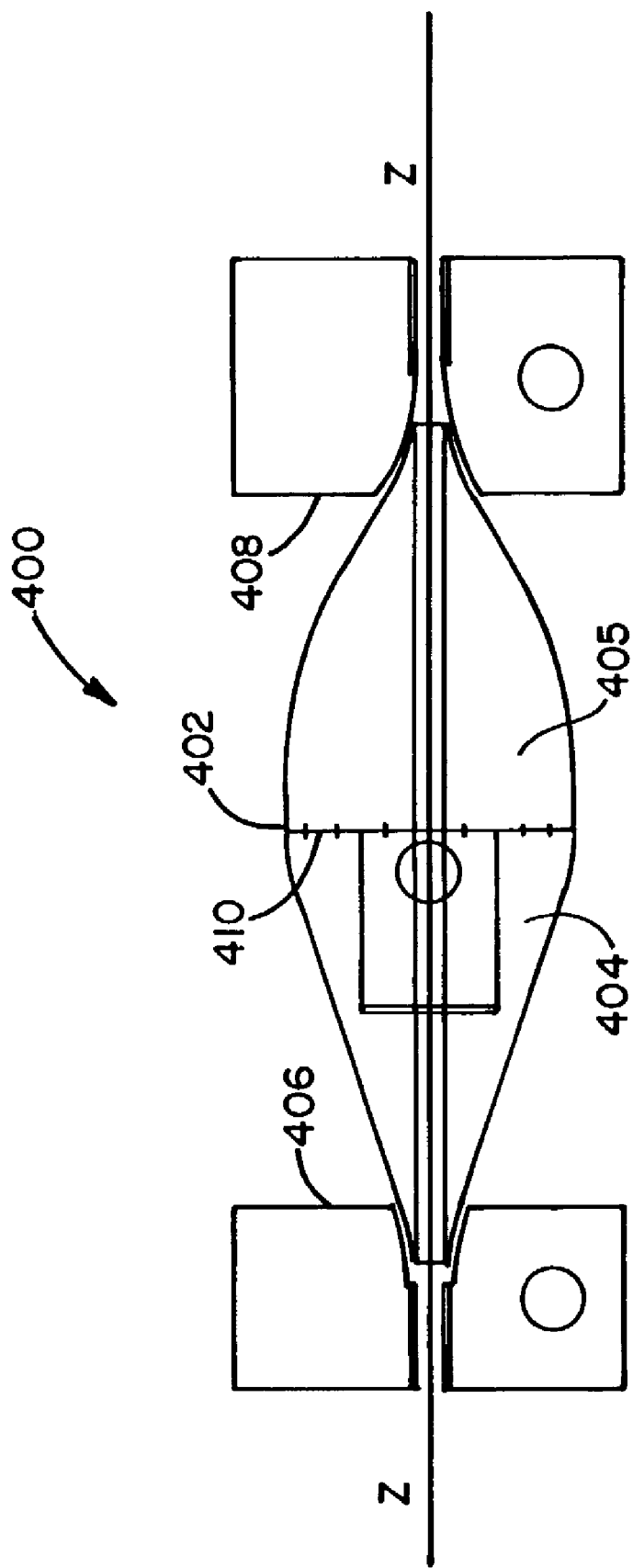
FIG. 31 is a sectional view of a profile device for forming expanded struts.

A method for making the trap and forming the struts 49 in the spiral configuration as shown in FIG. 7C may be used using a profile device. FIG. 31 depicts one embodiment of a profile device 400. The method for making the spiral shaped strut may comprise using a "shape memory alloy" to form the desired steady-state spiral struts 49 in the expanded position. This method involves positioning the struts 49 parallel to the longitudinal axis Z-Z of the device over a profile device 400 with a desired profile 402, i.e., egg shape, oval shape. The device 400 fixedly holds the struts 49 at a first 408 and second 406 end with a clamping device for fixing the strut. In addition, the device 400 across the center portion may have gaps 410 for the struts to be rigidly placed in. The gaps 410 keep the struts 49 evenly spaced from one another during the method of making the trap. The device 400 may include a rotatable section 404 and a stationary section 405. To form the spiral shaped struts 49, a rotatable portion 404, 406 of the device is rotated relative to a stationary portion 405, 408. The rotatable portion 404, 406 device is rotated in one embodiment 90° to achieve a spiral configuration. In another embodiment, both the stationary portion 405, 408 and the rotatable portion are rotated in opposite directions to achieve a spiral configuration. Other rotation degrees are within the scope of the present invention.

The strut are made of a material that may be set in the expanded position so that the steady-state position of the struts 49 is the expanded position of the profile device. In some embodiments the profile device is rotated and then the metal is set so that the expanded position of the struts forms a spiral configuration. In one embodiment the method used to set the strut material is heat treatment that would set the shape memory alloy of the struts 49 in the shape of the profile. In one embodiment the heat treatment is performed at a temperature of 500° F. for 10 minutes. In another embodiment, a sand bath with heated sand at 500° F. is applied for 5 minutes. Other times and temperatures are within the scope of the invention along with other methods of applying heat and in addition other methods of setting the material, like using electricity.

After the struts 49 are set, then the struts may be used in making the trapping device of the angioplasty device. Various numbers of struts may be used along with different profile shapes and different rotations of the rotatable portion 404.

Figure 34A:
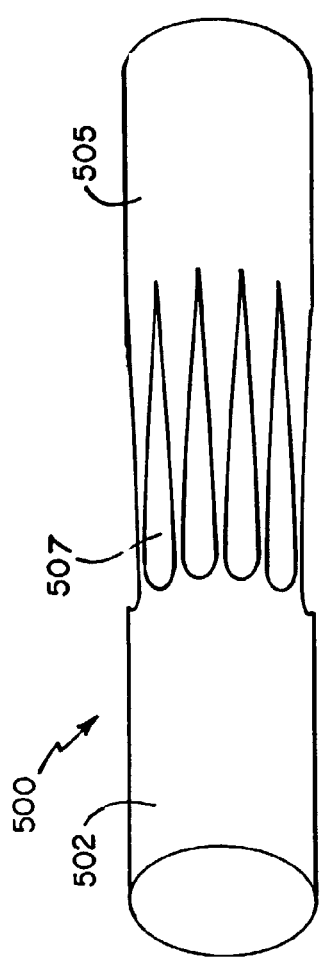
FIGS. 34A-C are sectional views of a trap formed from a tube with the struts varying in thickness.
Figure 34B:
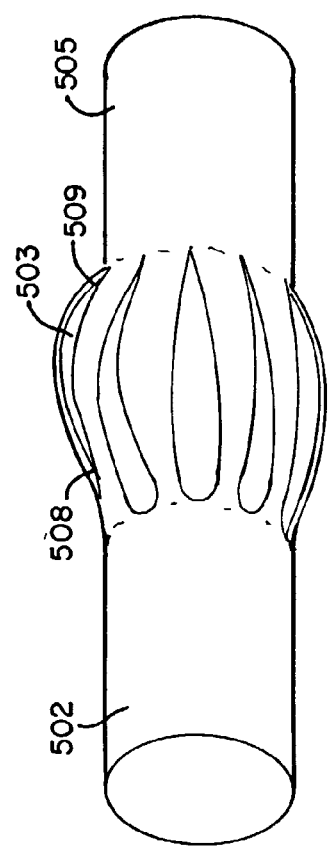
Figure 34C:
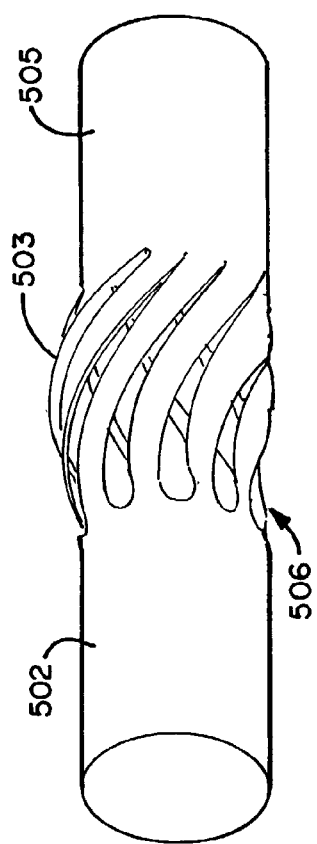

Another method for making the trap and forming the struts is to first form the struts not as individual sections of metal, but form the struts by cutting parallel sections from a tube. FIGS. 33A-33E depicts a tube 500 and the tube 500 with cut sections 501 forming struts 503. In this embodiment the midsection of the tube 500 is cut while leaving the ends 502, 505 of the tube intact. In this embodiment the material of the tube 500 can also be a shape memory alloy that may be set using heat treatment or other setting methods. In another embodiment, as shown in FIGS. 34A-34C, teardrop-shaped or wedge-shaped cut-outs 507 are formed in the tube 500, and this portion of the tube 500 is removed as shown. With these cut-outs 507 removed, the sections remaining form the struts 503 with a first end 508 thinner in width than a second end 509.

To form the profile shape, a profile device 510 is placed within the opening of the struts. This profile device 510 may have the shape of a desired profile 511, in one embodiment an egg shape. The profile device 510 has an opening 512 longitudinally through it. The profile device 510 is inserted into the cut sections 501, 507 of the tube 500. A generally rigid device is placed through the opening 512 of the profile device 510 so that a generally linear shape of the trap is formed. With the profile device 510 in position, the ends of the tube 502, 505 are clamped and then the struts 503 are set. In some embodiments one clamped end 505 is rotated relative to a stationary end 502 to form a spiral configuration 506 of the struts 503 and then the struts 503 are set. In one embodiment, the struts are set using heat treatment of 500° F. for 10 minutes or in a heated sand bath at 500° F. for 5 minutes. Other methods of setting the material, as known in the art, are within the scope of the invention.

In the embodiment depicted in FIGS. 34A-34C, the variable width of the struts 503 in the longitudinal direction helps facilitate control of closing one end of the trap before the other end of the trap. The first end 508 of the trap, having the narrower portion of the struts, requires less force to close, and therefore that end will close before the end having the wider portion of the struts.

In one embodiment, using the device shown in either FIGS. 33A-33E or FIGS. 34A-34C, a trap is formed by attaching a membrane (not shown) over a portion of the struts 503, and the trap is actuated using a guidewire or other movable member inserted through the lumen of the tube 500 and coupled to the distal end 505. To actuate the trap, the movable member is then rotated, translated longitudinally, or both, which causes the struts 503 to close beginning with the first end 508.

The guidewire 44 may be any device capable of guiding the catheter 26 into the treatment site and capable of transmitting sufficient torque from the guidewire port 34 to the struts 49. The guidewire 44 in some embodiments is made from a braided stainless steel wire. These embodiments are desirable because stainless steel has excellent strength and corrosion resistance, and is approved for use in medical devices. Stainless steel's strength and corrosion resistance may be particularly desirable for use in catheters having diameters of five French or less. Despite these advantages, non-braided guidewires 44; guidewires 44 made from other materials, such as platinum or a polymer; and embodiments having a removable guidewire 44 are within the scope of the present invention. The removable guidewire 44 in these embodiments may be operably connected to the struts 49 by any suitable means, such as mechanical or magnetic linkages.

The guidewire 44 in some embodiments may taper along its length from a larger diameter at the branching housing 28 to a smaller diameter at the trap 38. These embodiments are desirable because they help prevent the guidewire 44 and the catheter 26 from "looping" around themselves during use. Looping is commonly observed in phone cords and occurs when a wire is twisted around its longitudinal axis. Despite this advantage, non-tapered guidewires 44 are also within the scope of the present invention.

Figure 6:
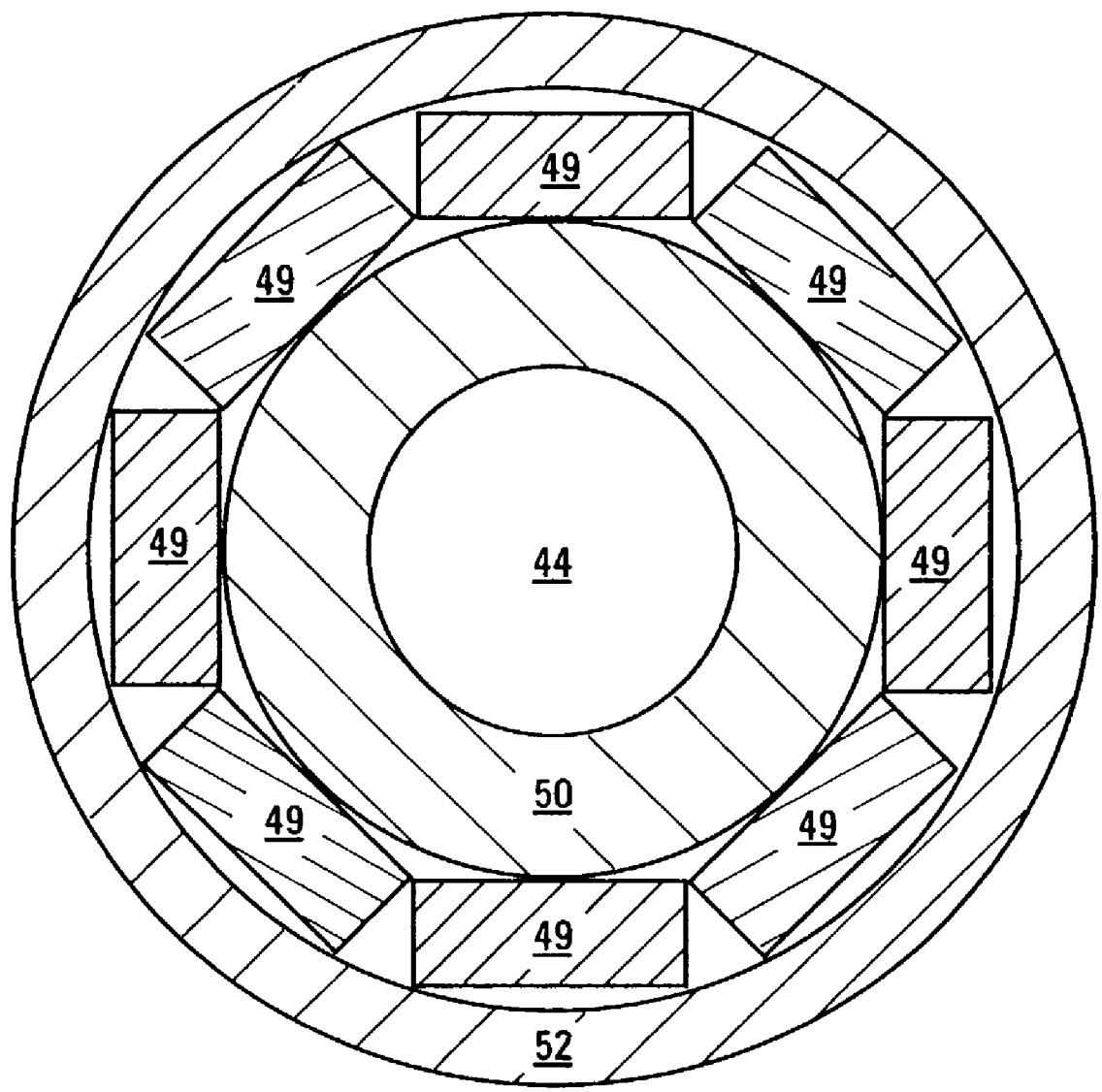
FIG. 6 is a sectional view of the embodiment depicted in FIG. 5, taken along the line CC.

In some embodiments, as best shown in FIG. 6, the struts 49 are clamped to the guidewire 44 by the rings 50 and 52. In these embodiments, the inner ring 50 is first attached to the guidewire 44 by any suitable mechanical means, such as swedging, press fitting, or brazing. The struts 49 are then aligned over the inner ring 50 and locked into place by swedging, press fitting, brazing, or other suitable means the outer ring 52 over and around the struts 49. In some embodiments, the struts 49 are coated with a material, such as textured polyurethane, that helps to prevent the struts 49 from slipping out of the rings 50 and 52 and that helps to adhesively connect the struts 49 to the membrane 56. Ring 54 similarly clamps the proximal end of the struts 49 against the inner wall 48 of the catheter 26. The single ring 54 may be attached to the struts 49 by any suitable means, such as swedging, press fitting, or through use of adhesives.

The struts 49 may also be embedded into the inner wall 48 of the catheter 26 or may be inserted into longitudinal grooves formed into the inner wall 48 in some embodiments, or alternatively, the catheter 26 may be formed or overmolded around the struts 49. These features may be desirable for small diameter angioplasty devices 20 because they may reduce the diameter of the ring 54 and because they may help to lock the struts 49 inside the ring 54. Inserting or embedding the struts 49 into the wall of the catheter can also eliminate the need for the ring 54.

Although stainless steel rings 50, 52, 54 are desirable to attach a Nitinol® strut 49 to a stainless steel guidewire 44, those skilled in the art will recognize that other means of attaching the struts 49 are within the scope of the present invention. This specifically includes, without being limited to, rings 50, 52, 54 made from other materials, such as mylar, that can be bonded to the coating on the struts 49 and the use of welding and/or adhesives to directly bond the struts 49 to the guidewire 44 and/or the inner wall 48. These alternative methods may be particularly desirable when used with struts 49 that are made from materials other than Nitinol® and when the guidewire 44 is made from materials other than stainless steel. These alternate attachment means may also be desirable for use with the embodiments shown in FIGS. 14-30.

The number of struts 49 and their dimensions are arbitrary. However, more struts 49 are generally desirable because they can more accurately bias the membrane 56 against the vessel or vessel-like structure. It is also desirable that each strut 49 have dimensions large enough that they can bias the membrane 56 against the vessel with sufficient force to prevent physiologically significant particles from escaping around the trap 38, but not so large that the struts 49 will prevent capture of the particles or so large that the struts 49 will interfere with each other when in their closed position. One suitable five French catheter 26 embodiment uses eight 0.006 inch×0.003 inch Nitinol® struts.

The membrane 56 may be any material capable of stopping physiologically significant materials from leaving the treatment site when the trap 38 is expanded. In some embodiments, the membrane 56 is made from a relatively strong, non-elastic material. Non-elastic materials are desirable because they do not counteract the radially outward biasing force developed by the struts 49. In other embodiments, the membrane 56 is made from an elastic or semielastic material, such as polyurethane, polyester, polyvinyl chloride, or polystyrene. These embodiments are desirable because the elasticity may help the struts 49 to close the trap 38. In still other embodiments, the membrane 56 is porous. These embodiments may be desirable because the pressure developed by patient's heart will help deliver particles into the trap 38.

Figure 11B:
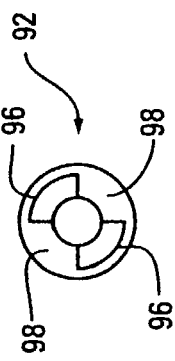
FIGS. 11B and 11C are side plan views of two disks for use with the embodiment in FIG. 11A.
Figure 11C:
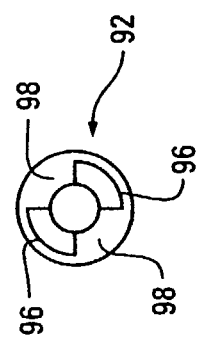
Figure 11A:
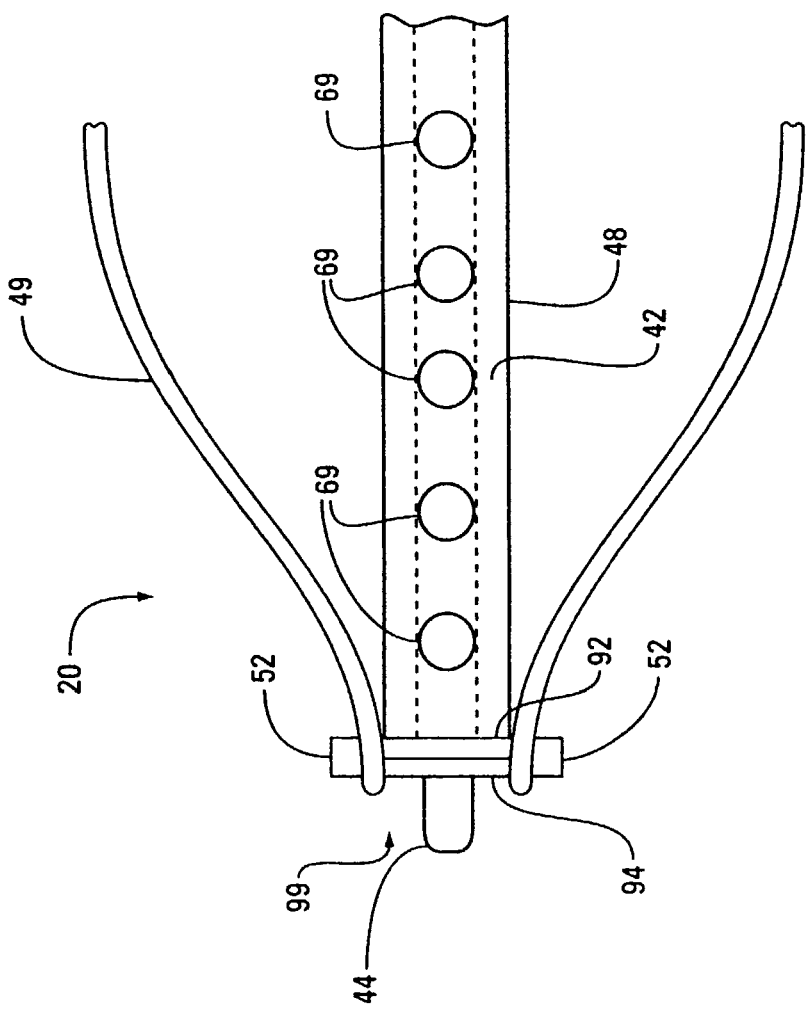
FIG. 11A is a side plan view of an embodiment capable of providing suction during insertion.

FIG. 11A shows an angioplasty device 20 capable of providing suction distal to the angioplasty device 20 while it is being inserted into the treatment site. In this embodiment, the ring 50 is replaced with a disk 92 attached to the inner wall 48 and a disk 94 attached to the guidewire 44. These two disks 92 and 94 act as a valve capable of selectively permitting suction to that portion 99 of the vessel immediately in front of the angioplasty device 20. That is, as shown in FIGS. 11B and 11C, each disk 92 and 94 has two open portions 96 and two blocking portions 98. Rotation of the guidewire 44 causes disk 94 to rotate relative to disk 92. This relative motion causes the disks 92 and 94 to alternate between an "open" orientation in which the openings 96 in disk 92 are aligned with the openings 96 in disk 94 and a "closed" orientation in which the openings 96 in disk 92 are aligned with the blocking portions 98 in disk 94. Preferably, the same rotation of the guidewire 44 used to toggle the disks 92 and 94 between their open and closed orientations also expands and contracts the trap 38.

In operation, the user would first rotate the guidewire 44 until the disks 92 and 94 are in the open orientation. In this orientation, the openings 96 cooperate to create a fluid communication channel between the suction lumen 42 and that portion 99 of the vessel immediately distal to the angioplasty device 20. This allows the user to provide suction in front of the angioplasty device 20 while the user inserts it into the vessel. Once the angioplasty device 20 is in place, the user will rotate the guidewire 44 until the disks are in the closed orientation. In this orientation, the blocking portions 98 cooperate to prevent fluid from flowing through the disks 92 and 94. This, in turn, creates suction inside the trap 38.

FIGS. 12A and 12B show an angioplasty device 20 with an alternate valve embodiment 120. This valve embodiment 120 comprises a disk shaped abutment 121 that is rigidly attached to the catheter wall 48 and a stopper 122 that is rigidly attached to the guidewire 44 at a location distal to the abutment 121. The stopper 122 has a conically shaped surface 124 on its distal end and a generally planar engagement surface 126 on its proximal end. The engagement surface 126 of the stopper 122 can selectively plug a circular flow channel 128 that is coaxially located in the abutment 121. The valve 120 allows the user to apply suction to the portion 99 of the vessel immediately in front of the angioplasty device 20 through a hole 129 in the membrane 56.

In operation, the valve embodiment 120 is actuated by longitudinally moving the guidewire 44 relative to the catheter wall 48. That is, pulling the guidewire 44 in a proximal direction relative to the catheter wall 48 causes the generally planar engagement surface 126 to sealably engage the abutment 121, which prevents fluid from flowing through the circular flow channel 128. Pushing the guidewire 44 in a distal direction relative to the catheter wall 48 causes the stopper 122 to disengage from the abutment 121, which allows fluid to flow through the circular flow channel 128.

Other valve embodiments 120 capable of being actuated by longitudinal motion are also within the scope of the present invention. For example, the stopper 122 may be rotated 180 degrees so that the conically shaped surface 124 engages the abutment 121, rather than the generally planar engagement surface 126. These embodiments may be desirable because the conically shaped surface 124 will self-center the stopper 122 in the flow channel 128. Also, the stopper 122 may be located proximal to the abutment 121. In addition, the stopper 122 may have other shapes, such as a sphere or a cylinder.

Those skilled in the art will recognize that the valve 120 and the disks 92, 94 can be eliminated in these embodiments, which allows the suction lumen 42 to simultaneously provide suction under the trap 38 and distal to the angioplasty device.

FIG. 13 shows an embodiment where the balloon 36 and the trap 38 are associated with separate catheter bundles. That is, FIG. 13 shows an embodiment of the present invention comprising a trap catheter bundle 100 for the trap 38 and a balloon catheter bundle 102 for the balloon. In operation, the trap catheter bundle 100 is inserted into vessel until the trap 38 is situated distal to the obstruction site. The balloon catheter bundle 102 is then loaded over the trap catheter bundle 100 and used to remove the obstruction. This balloon catheter bundle 102 should have a centrally located lumen 104 having an interior diameter larger than the trap catheter bundle 100. Alternatively, the balloon catheter bundle 102 or other device (such as an angioscope) may be delivered to the treatment area through a lumen 150 and an opening 152 in the trap catheter bundle 100 (see FIGS. 16-18).

Figure 14:
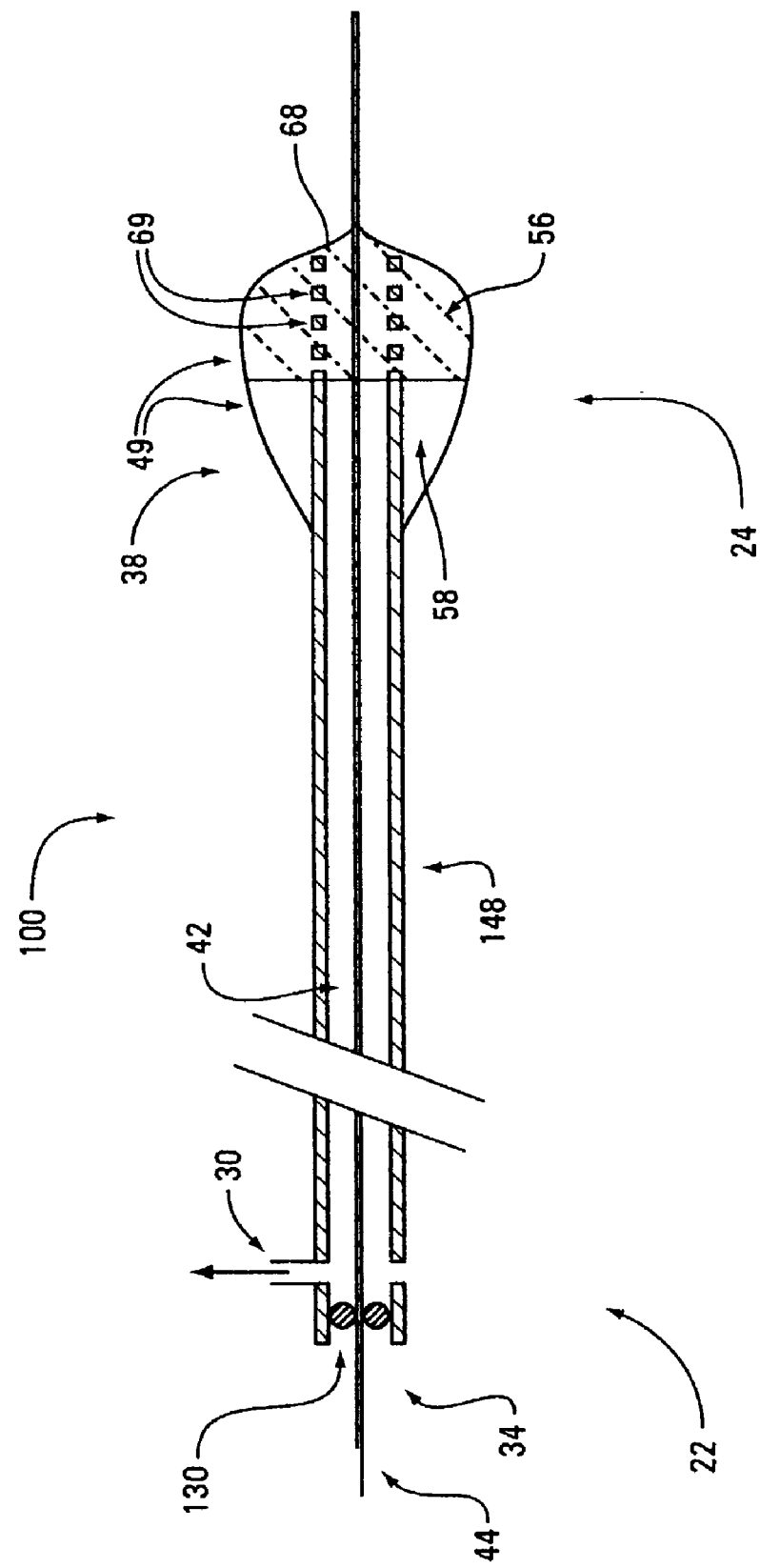
FIG. 14 is a sectional view of a trap catheter bundle embodiment configured for use in the antegrade direction.
Figure 15:
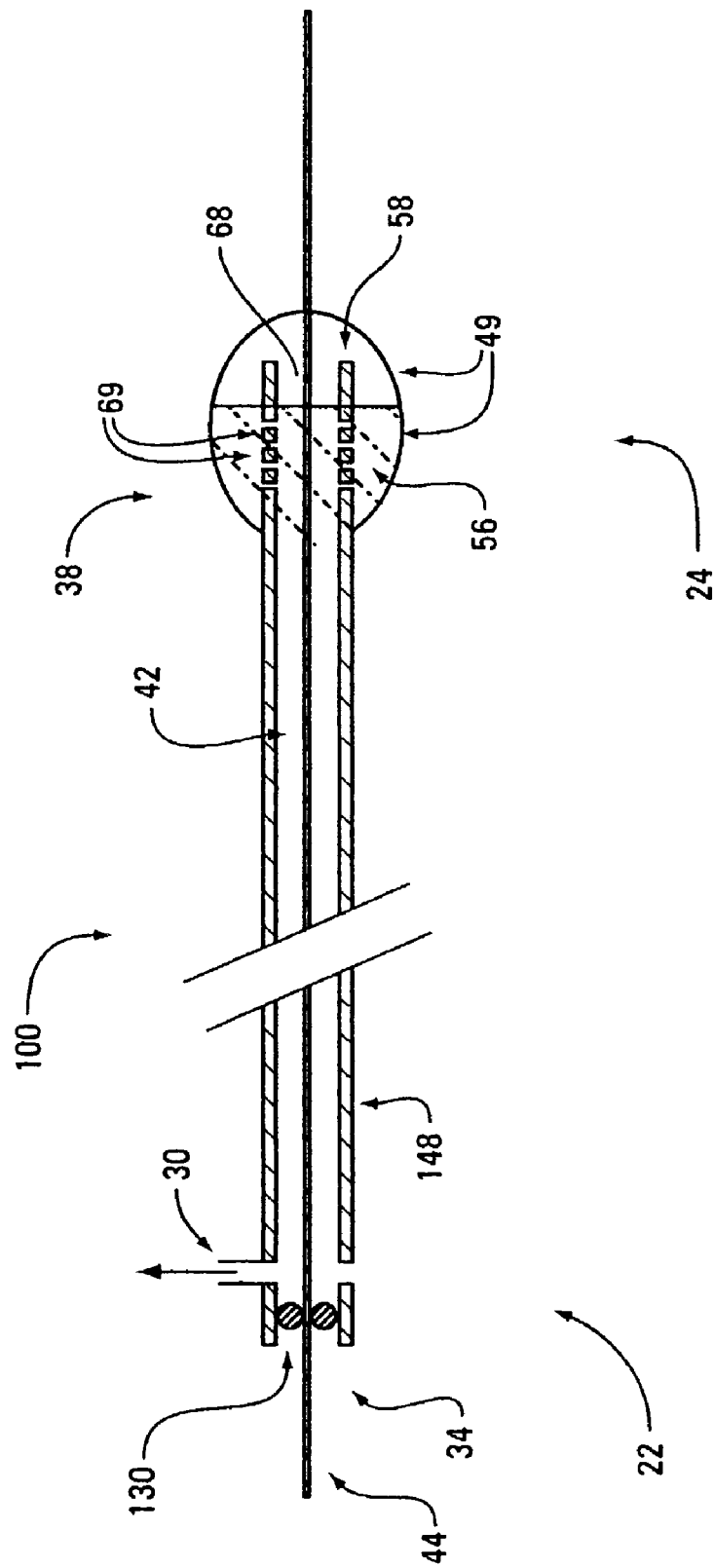
FIG. 15 is a sectional view of a trap catheter bundle embodiment configured for use in the retrograde direction.

FIGS. 14 and 15 are sectional views of two trap catheter bundle embodiments 100. Specifically, the trap catheter bundle 100 in FIG. 14 is configured to be inserted in an antegrade direction (i.e., in same the direction as the fluid flow) along a guidewire 44. Thus, the opening 58 in its membrane 38 faces towards its proximal end. The opening 58 in FIG. 15, in contrast, faces the catheter's distal end because this catheter bundle 100 is configured to be inserted in a retrograde direction (i.e., with insertion site "downstream" in relation to the direction of fluid flow) along a guidewire 44. Both trap catheter bundles 100 may be sized and shaped so that they can be inserted through the guidewire channel of a balloon catheter bundle 102. Those skilled in the art will recognize that the trap catheter bundle embodiments 100 in FIGS. 14 and 15 can also be used to capture embolic debris without a balloon catheter bundle 102 and to deliver diagnostic and therapeutic agents to a treatment area.

FIGS. 14 and 15 also show a seal 130 that may be used in place of or in addition to the flexible membrane extension system 80a depicted in FIG. 10 to prevent air or other fluid from leaking into the suction lumen 42. Accordingly, the seal 130 may be any device, such as an elastomeric O-ring or wiper, that prevents fluid from leaking through the guidewire port 34 and that allows the guidewire 44 to move relative to the catheter wall 148. Embodiments using an O-ring or a wiper style seal 130 are particularly desirable because the user can slide the guidewire 44 longitudinally relative to the catheter bundle 102 to help actuate the trap 38.

Figure 15A:
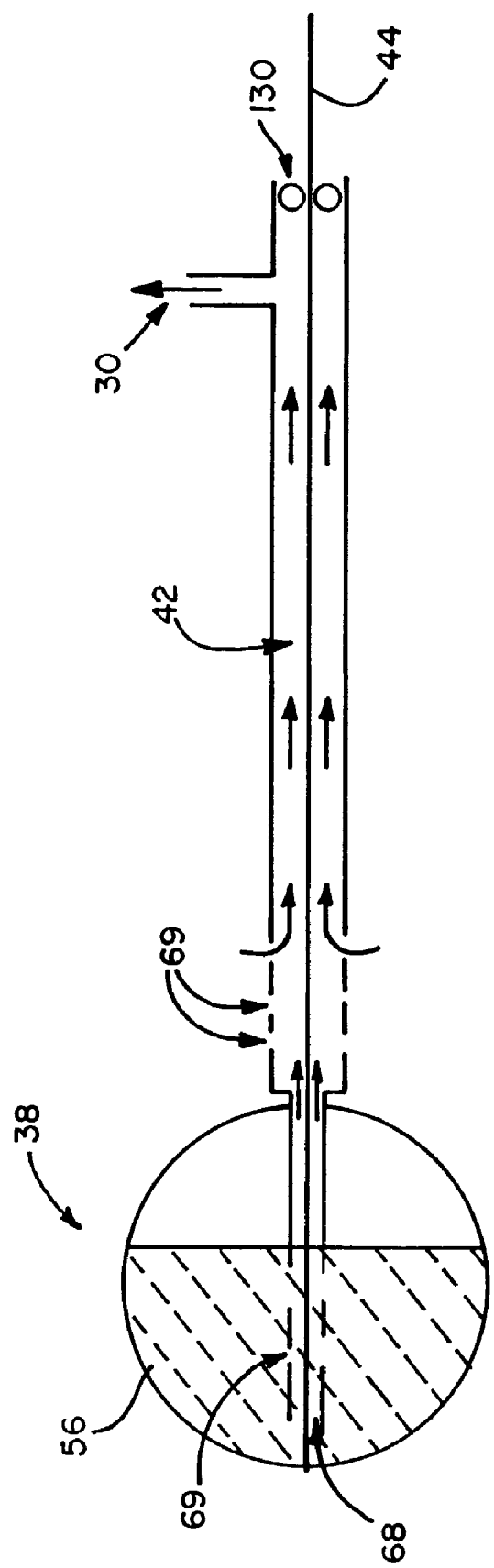
FIG. 15A is a section view of a trap catheter bundle with a stepped-up suction lumen.

FIG. 15A is a sectional view of a trap catheter bundle embodiment with a stepped-up suction lumen 42. In this embodiment there is an opening 68 in fluid communication with the suction lumen along with suction pores 69 in fluid communication with the suction lumen. The diameter of the suction lumen 42 is smaller in the portion under the membrane 56 than another portion leading to the suction port 30. The suction pores 69 are located on both portions of the suction lumen 42. It is understood that the stepped-up suction lumen may be the lumen that receives a guidewire 44 or another catheter and that an inflation lumen may also be provided.

Figure 15B:
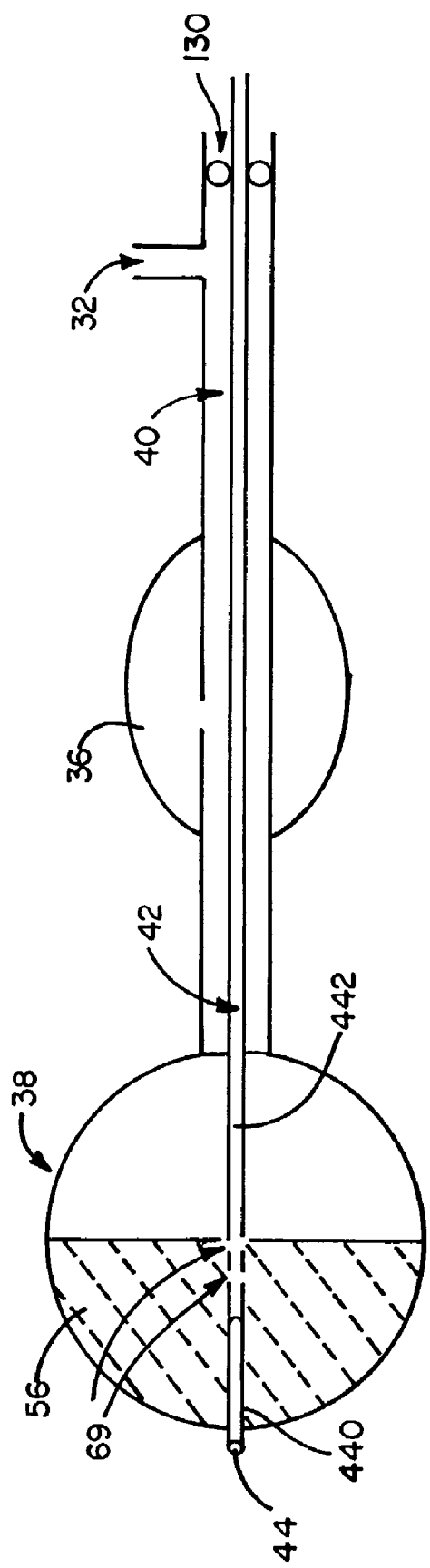
FIG. 15B is a section view of a trap catheter bundle with a guidewire having a solid portion and a suction lumen.

FIG. 15B is a sectional view of a trap catheter bundle embodiment with the guidewire 44 having a solid portion 440 and a hollow portion 442 providing the suction lumen 42 with pores 69. The guidewire 44 may be located within an inflation lumen 40.

Figure 16:
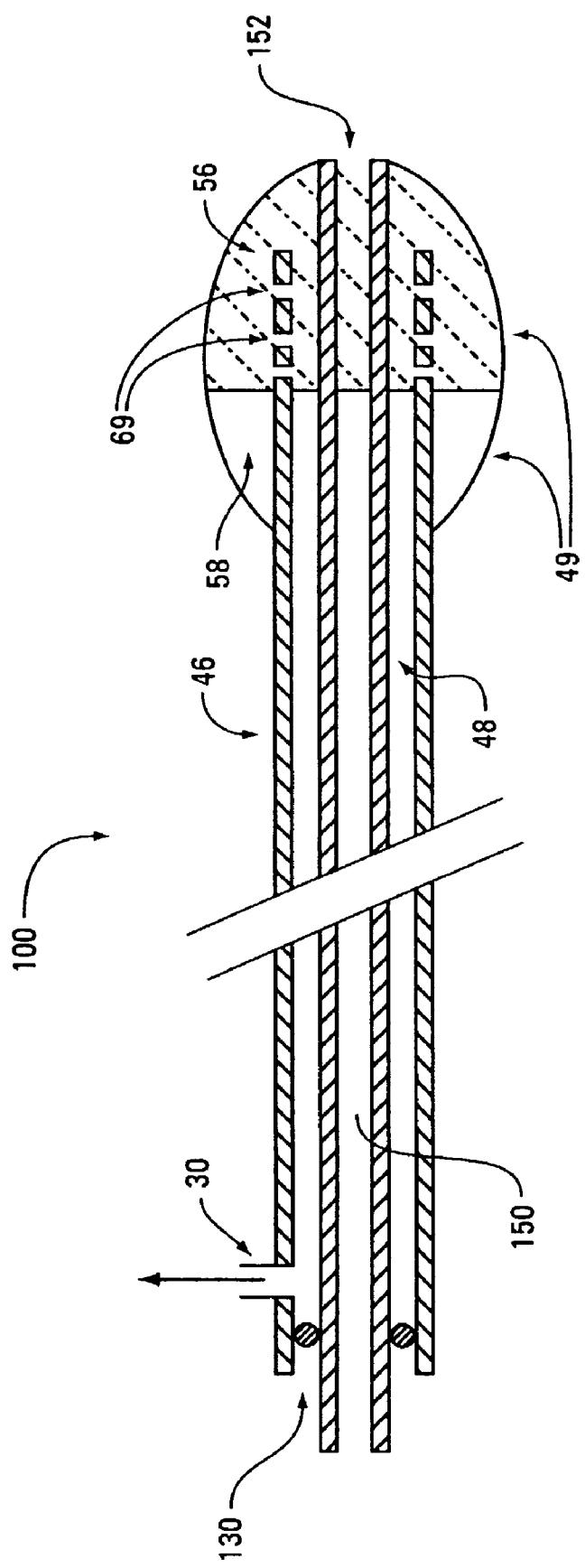
FIG. 16 is a sectional view of a trap catheter bundle embodiment configured for use in the antegrade direction, in which the trap is actuated by relative motion between an inner catheter wall and an outer catheter wall.
Figure 17:
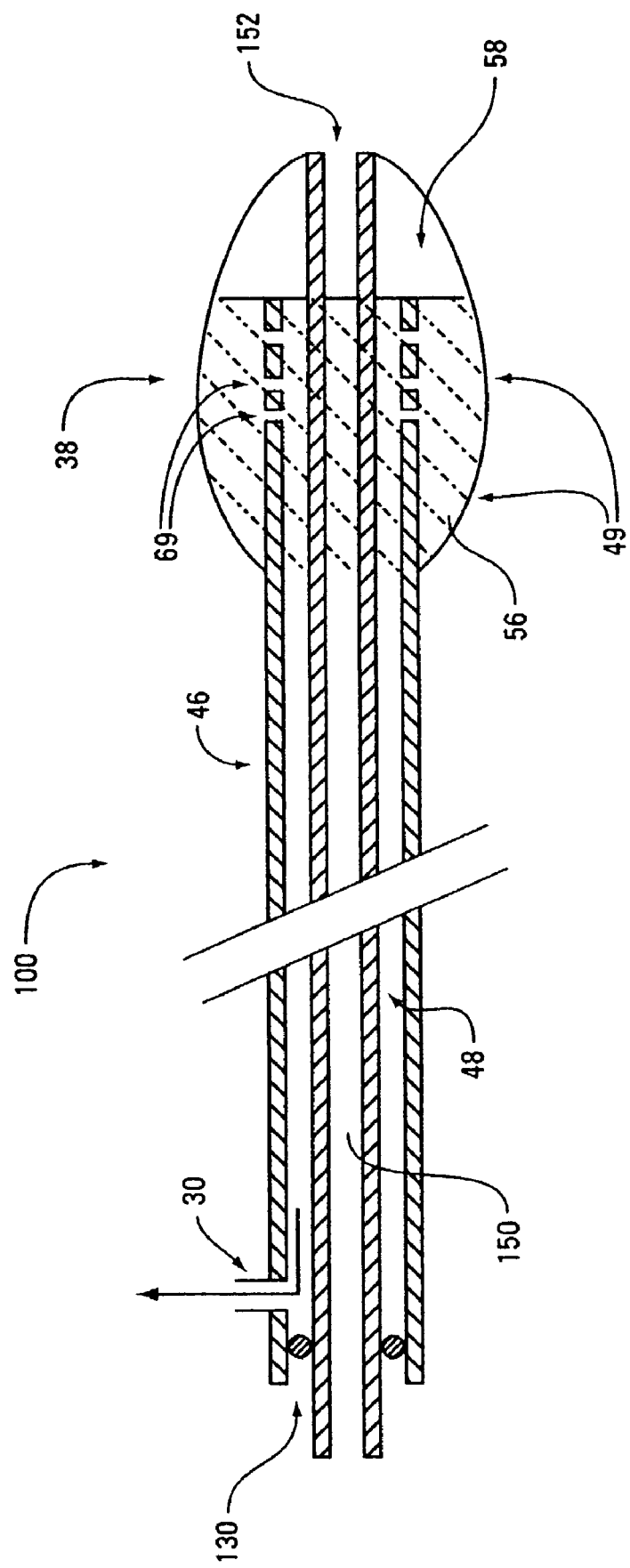
FIG. 17 is a sectional view of a trap catheter bundle embodiment configured for use in the retrograde direction, in which the trap is actuated by relative motion between an inner catheter wall and an outer catheter wall.

FIGS. 16 and 17 are sectional views of two trap catheter bundle embodiments 100 in which the trap is actuated by relative motion between the inner catheter wall 48 and the outer catheter wall 46. That is, the user actuates the trap 38 in this embodiment by rotating the inner catheter wall 48 relative to the outer catheter wall 46, rather than rotating a fixed guidewire 44 relative to the inner catheter wall 48. These embodiments are desirable because they can be loaded over a separate guidewire (not shown) or angioplasty device (not shown) that has previously been inserted into the patient using lumen 150 and opening 152. In these embodiments, various forms of arcuately expanded positions of struts may be utilized including but not limited to expanded positions where the struts are parallel to the longitudinal axis of the device or expanded positions where the struts form a spiral configuration and circle the longitudinal axis of the device. These embodiments are also desirable because inner catheter wall 48 can be slid longitudinally with respect to the outer catheter wall 46 to help open and close the trap 38. In an appropriately designed balloon catheter bundle, these trap catheter bundles could be inserted through the lumen 150 of the angioplasty balloon catheter. Like the trap catheter bundle embodiments 100 in FIGS. 14 and 15, the trap catheter embodiments 100 in FIGS. 16 and 17 can be inserted in either the antegrade or retrograde direction, and can be used with or without a separate balloon catheter bundle 102. In one embodiment, the handle 320 (shown in FIG. 32) is used to actuate movement of the inner catheter wall 48 and hold the outer catheter wall 46 stationary and similar longitudinal and/or rotational movement through the handle 320 (shown in FIG. 32) may be used to actuate the trap 38 as discussed in other embodiments.

Figure 1:
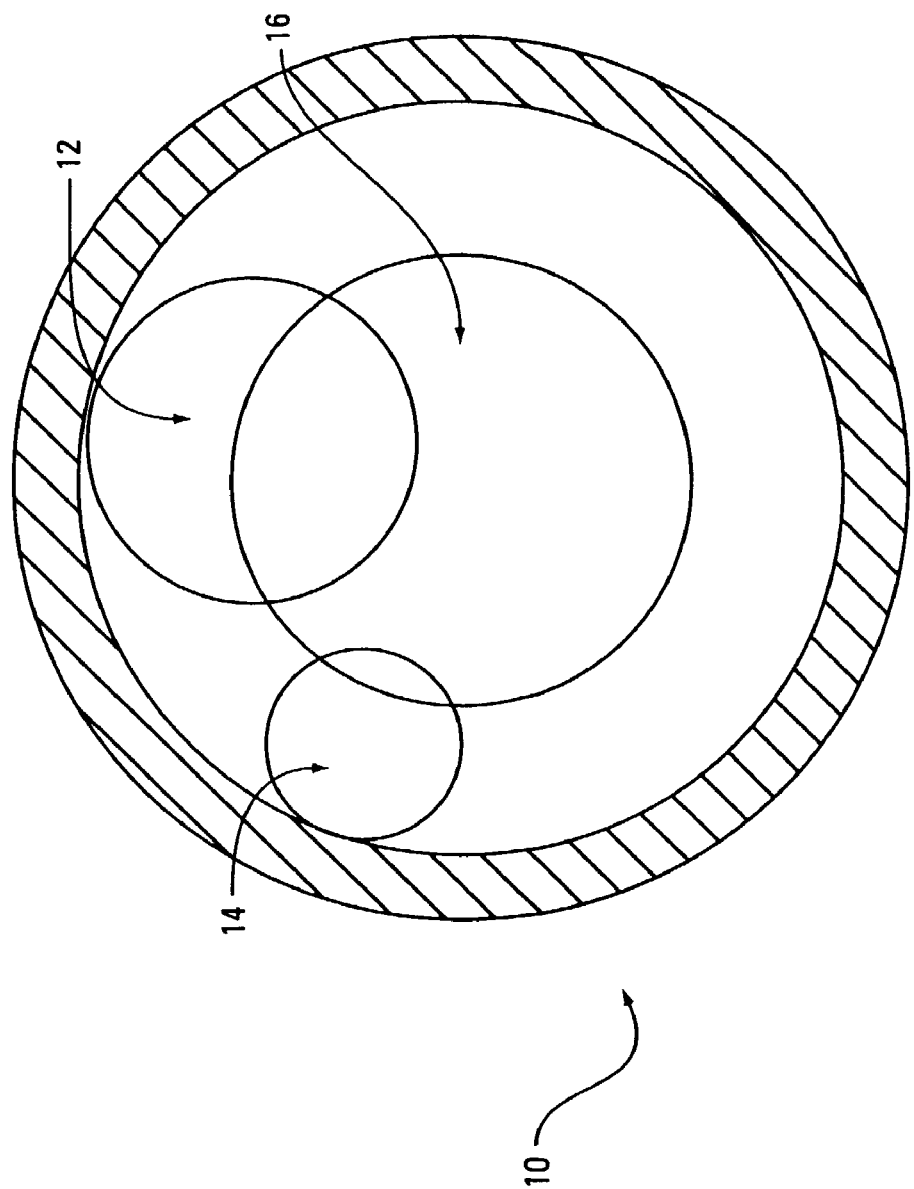
FIG. 1 (prior art) is a sectional view illustrating the size limits of a conventional five French catheter.
Figure 18A:
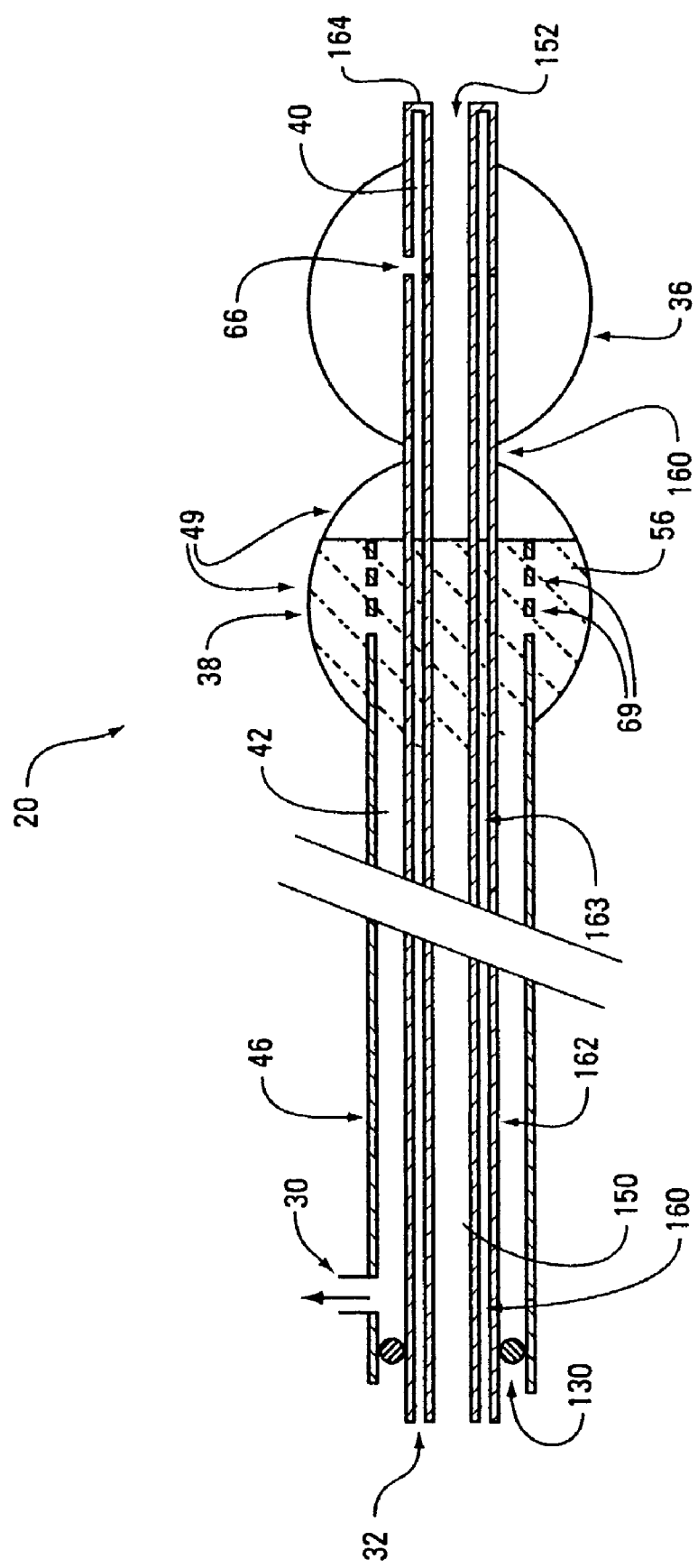
FIG. 18A is a sectional view of an angioplasty device embodiment configured for use in the retrograde direction in which the trap is actuated by relative motion between an inner catheter wall and an outer catheter wall.

FIG. 18A is a sectional view of an angioplasty device 20 embodiment for use in retrograde applications (see FIG. 1 of U.S. Pat. No. 4,794,928 for conceptional orientation, which is herein incorporated by reference). This embodiment comprises a separate catheter 160 for the balloon 36 and for the inflation/deflation lumen 40. This catheter 160 has a first wall 162, a second wall 163, and an end wall or plug 164. In operation, the trap 38 in this embodiment is actuated by relative rotational and/or longitudinal motion between the exterior wall 46 and the first wall 162 of the catheter 160. In one embodiment, the handle 320 (shown in FIG. 32) provides the movement of first wall 162 relative to exterior wall 46.

Figure 18B:
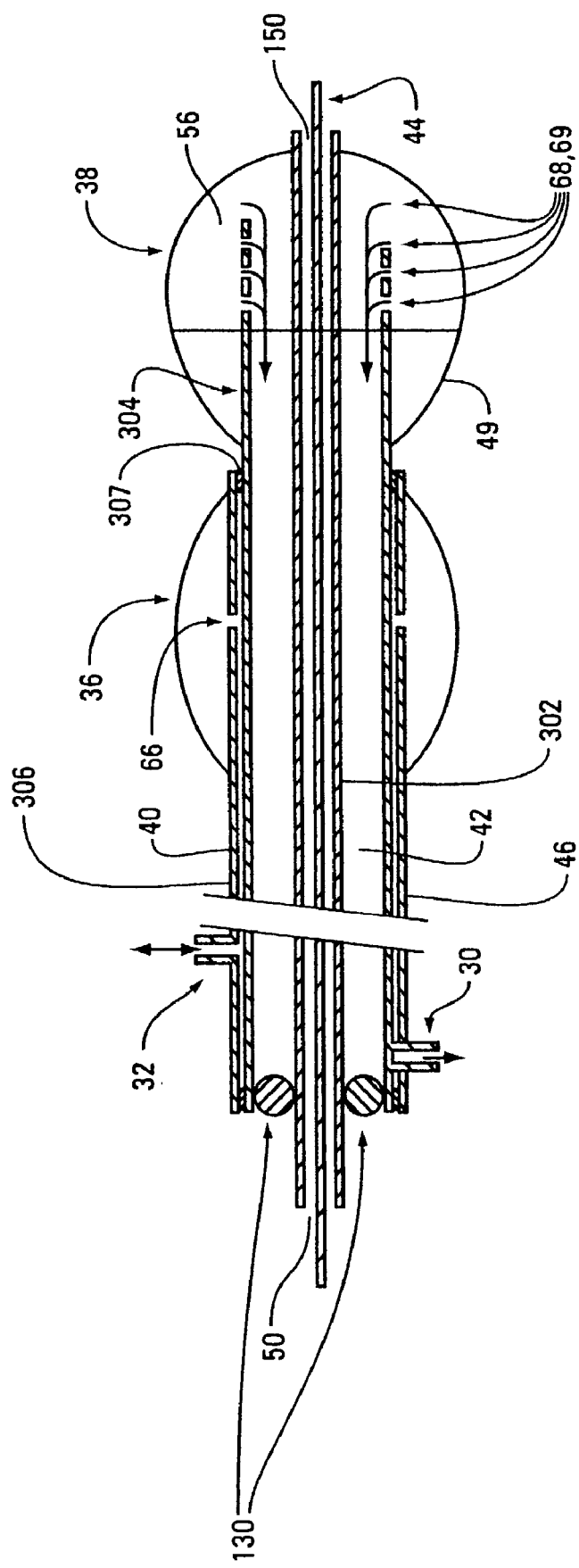
FIG. 18B is a sectional view of an angioplasty device embodiment configured for use in the antegrade direction in which the trap is actuated by relative motion between an inner catheter wall and an outer catheter wall.

FIG. 18B is sectional view of an angioplasty device 20 embodiment configured for use in the antegrade direction and for use with a pre-inserted guidewire. This angioplasty device 20 embodiment includes an inner wall 302, an intermediate wall 304, an outer wall 306, and an end seal 307. The inner wall 302 forms a guidewire receiving lumen 150 having a shape and size suitable to slideably receive a guidewire 44. The inner wall 302 and the intermediate wall 304 form a suction lumen 42, which is fluidly connected to a suction port 30 and a plurality of openings 68 and/or pores 69. The intermediate wall 304 and the outer wall 306 form an inflation/deflation lumen 40, which is fluidly connected to the balloon 36. In operation, the trap 38 is actuated using relative rotational and/or longitudinal motion between the intermediate wall 304 and the inner wall 302. In one embodiment, the handle 320 (shown in FIG. 32) provides the relative movement between the intermediate wall 304 and the inner wall 302.

Like the embodiments in FIGS. 16-17, 19 and 27, the angioplasty device embodiments 20 in FIGS. 18A and 18B are desirable because they may be loaded over a separate guidewire (not shown in FIG. 18A) or catheter (not shown) that has previously been inserted into the patient. In a typical over-the-wire surgical procedure, a surgeon may first insert a guidewire 44 into a vessel-like structure using a long hypodermic needle tube or other suitable device (not shown) until the guidewire 44 extends to a desired point past the obstruction. The surgeon then inserts the angioplasty device 20 over the guidewire 44 until the trap 38 is located downstream from the obstruction. That is, the surgeon slides the angioplasty device 20 down the guidewire 44 (with the guidewire 44 sliding through the guidewire lumen 150) to the treatment site. After the angioplasty device 20 is properly positioned, the surgeon then performs the angioplasty procedure as previously described. These over-the-wire embodiments may be desirable for use in severely occluded vessels because the separate guidewire 44 is easier to manipulate through the obstruction and because many surgeons are experienced in inserting and manipulating the separate guidewire 44 into the proper position. Over-the-wire embodiments are also desirable because the lumen 150 may be used to deliver medicine, blood, or other fluid past the obstruction during the procedure.

Figure 19:
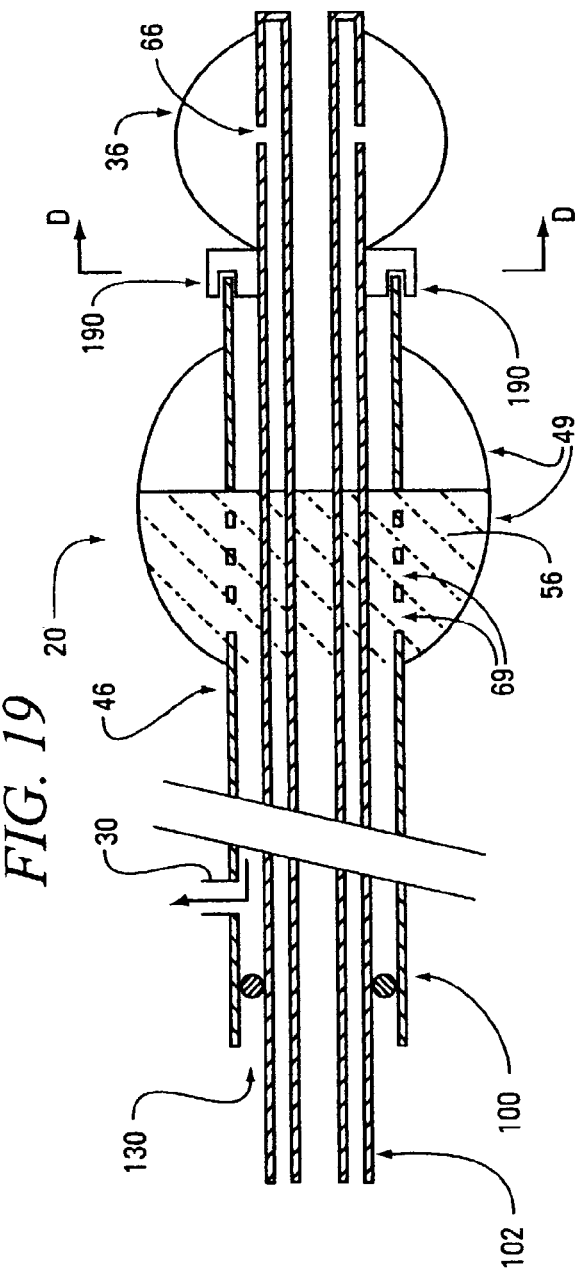
FIG. 19 is a sectional view of an angioplasty device embodiment having a coupling device.
Figure 20:
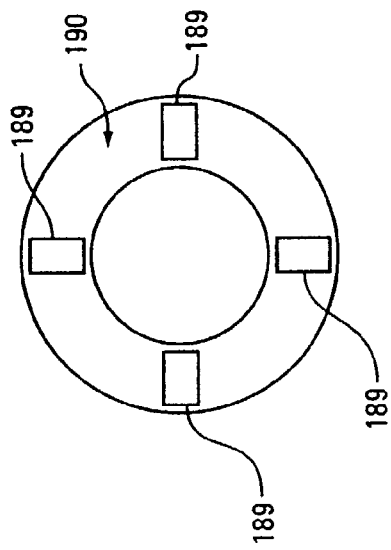
FIG. 20 is a sectional view of the coupling device in FIG. 19.
Figure 27:
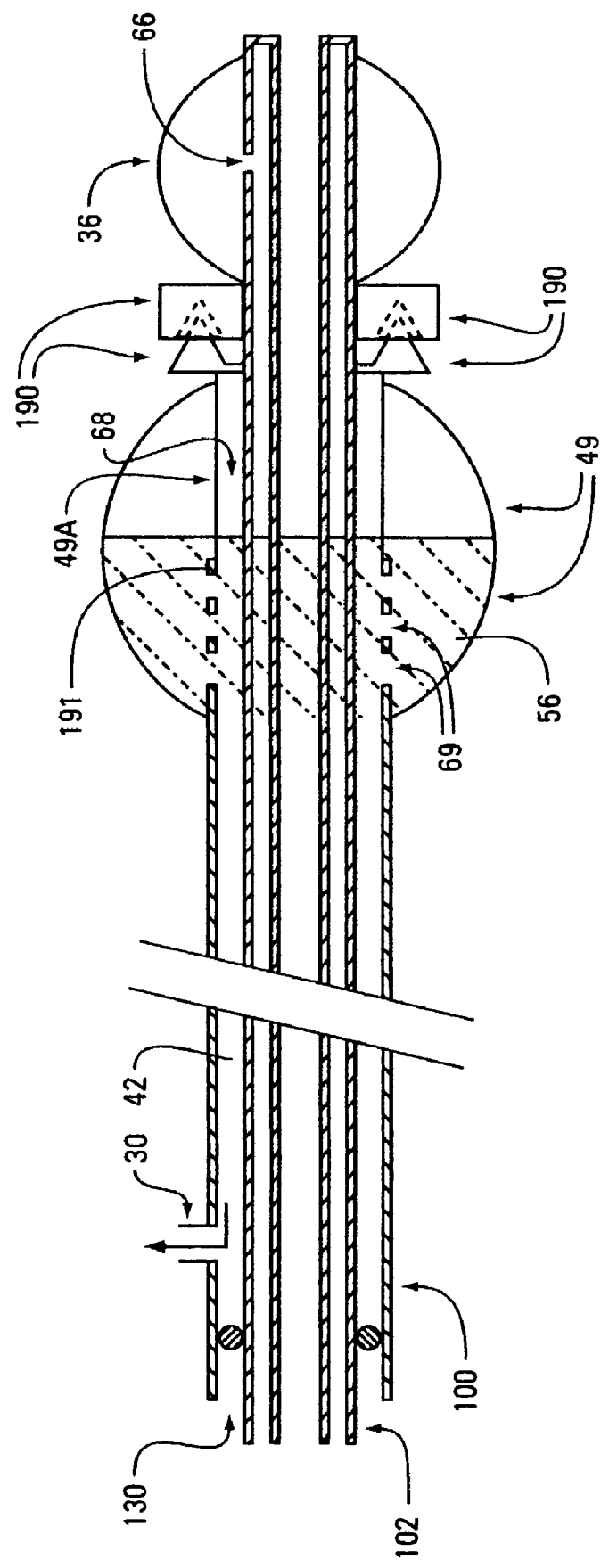
FIG. 27 is a sectional view of an embodiment in which a plurality of struts connect a coupling device to the angioplasty catheter.

FIG. 19 is a sectional view of an angioplasty device embodiment having a coupling device 190 with four radially spaced sockets 189. FIG. 20 is a sectional view of the coupling device 190. The coupling device 190 in this embodiment may be any device that prevents the balloon catheter 102 from rotating relative to the trap catheter bundle 100 (or translating, if used with the trap embodiment 38 described with reference to FIGS. 21 and 22). These embodiments are desirable because the trap catheter bundle 100 and the balloon catheter bundle 102 may be manufactured separately, then combined as needed. FIG. 27 depicts an alternate embodiment in which a second group of struts 49a connect the coupling device 190 to an end 191 of the trap catheter bundle 100. In operation, the trap catheter bundles 100 in FIGS. 19 and 27 may be inserted over an in-place balloon catheter 102 and then either removed along with the balloon catheter 102 or by itself, depending on the configuration of the coupling devices 190. The embodiments in FIGS. 19 and 27 may also be inserted over a guidewire 44 (not shown) or a may have a fixed guidewire 44 extending distally from it.

FIGS. 21 and 22 are sectional views of another trap catheter bundle embodiment 100, in which the trap 38 is actuated by a translation between the guidewire 44 and the catheter wall 148. In this embodiment, a first end 180 of the struts 49 is connected to the guidewire 44 and a second end 182 of the struts 49 is attached to the catheter wall 148. Translating the guidewire 44 (i.e., moving the guidewire in an axial direction) relative to the catheter wall 148 biases the first end 180 away from the end 182. This, in turn, actuates the struts 49 between an arcuately expanded position, such as that shown in FIG. 21, and a contracted position, such as that shown in FIG. 22. Accordingly, the struts 49 in this embodiment remain generally parallel to the guidewire 44 throughout the procedure. Those skilled in the art will recognize that this actuation mechanism also could be used with the embodiments described with reference to FIGS. 1-20.

Figure 23A:
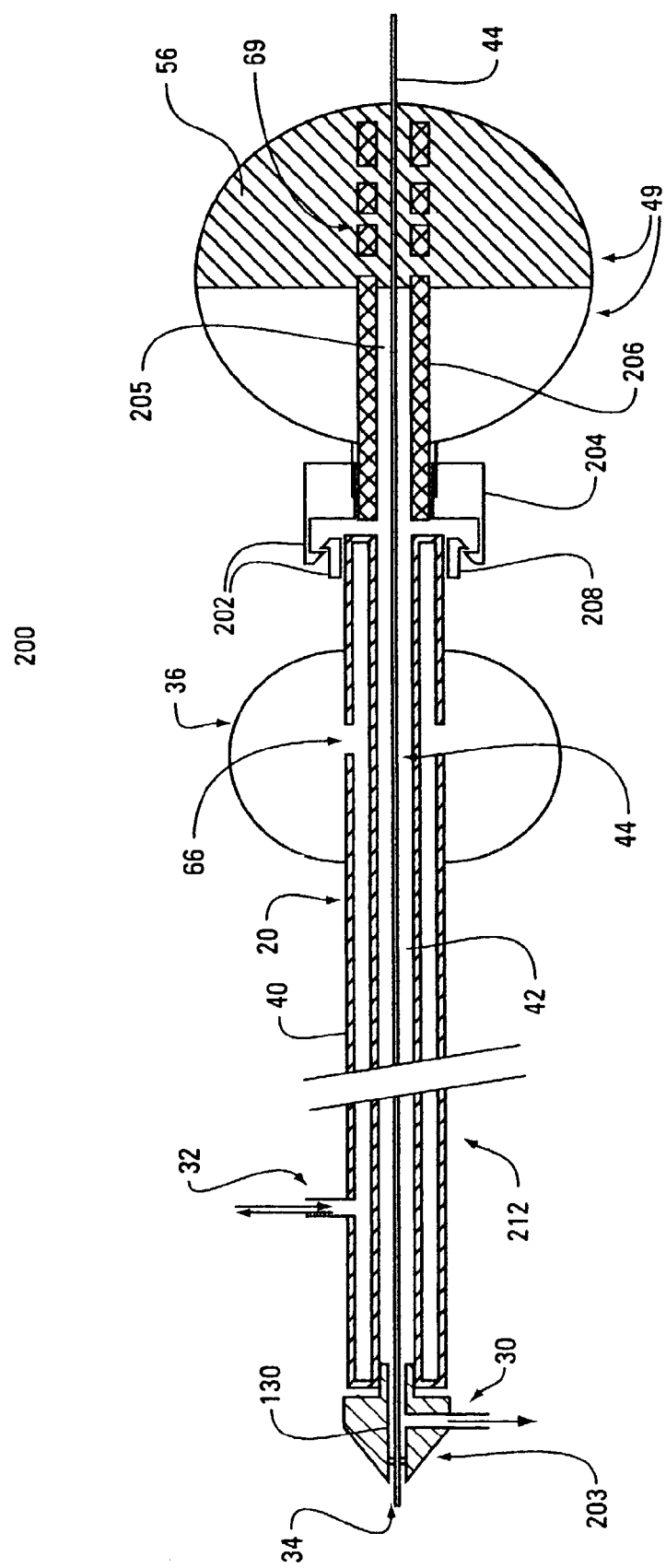
FIG. 23A is a sectional view of a modular trap embodiment.

FIGS. 23A-24B are sectional views of two modular trap embodiments 200 having an adaptive coupling device 202, and a permanent or detachable and/or insertable manifold 203. These embodiments are desirable because the user can add aspiration and blocking features to a conventional angioplasty device 212, and because the user can customize the operative device and the trap for a particular operation. In FIG. 23A, the coupling device 202 comprises a male snap ring 204 that is adhesively bonded to a modular catheter wall 206 and a female snap ring 208 that is adhesively bonded to an outer wall 210 of a conventional angioplasty device 212. The snap rings 204 and 208 sealably mate together, which fluidly connects a modular catheter lumen 205 to the suction lumen 42. In FIG. 24A, the coupling device 202 comprises a first ring 220 and a second ring 222. The first ring 220 has a circumferential slot 224 in its proximal end into which the struts 49 are fixed and a circumferential tab 226 that projects axially from its distal end. The second ring 222, which is attached to a conventional angioplasty device 212, has a circumferential slot 228 into which the tab 226 is press fit, snap fit, or otherwise locked shortly before use. Alternatively, second ring 222 could be eliminated and the tab 226 inserted directly into, and held in place by, the suction lumen 42 and/or an adhesive or tape. The embodiment in FIG. 24A may be particularly desirable because it does not require a modular catheter wall 206.

Figure 23B:
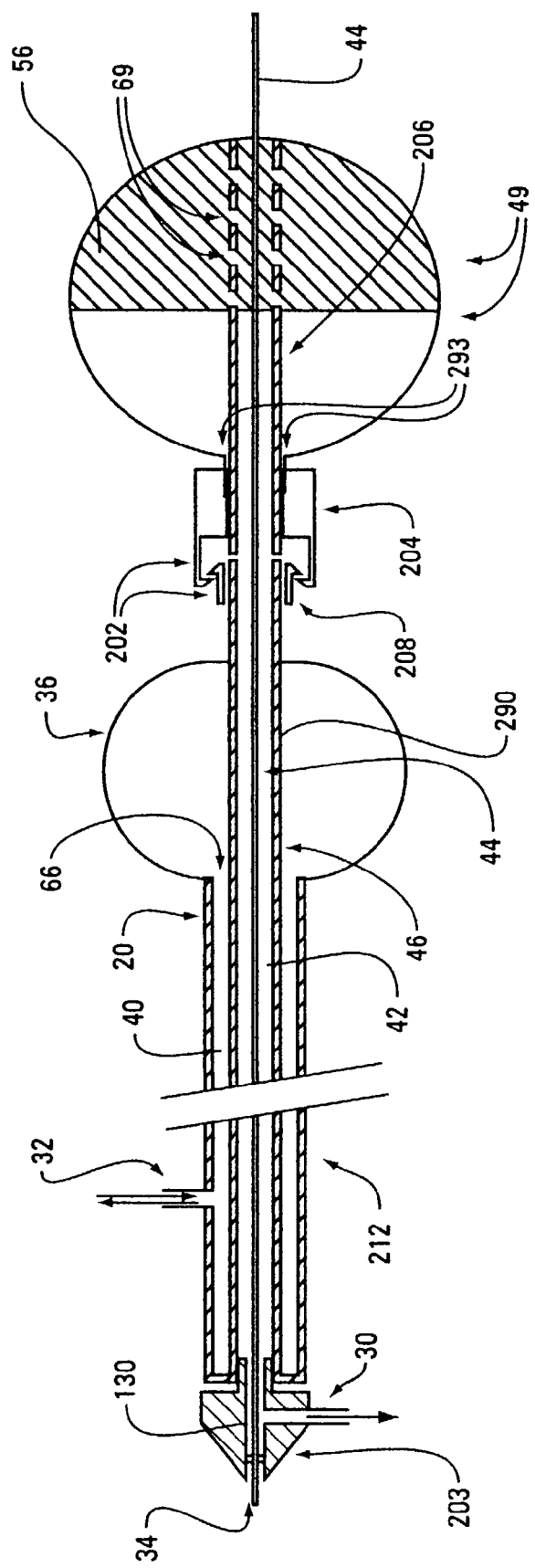
FIGS. 23B, 24A, and 24B are sectional views of alternate modular trap embodiments.
Figure 24A:
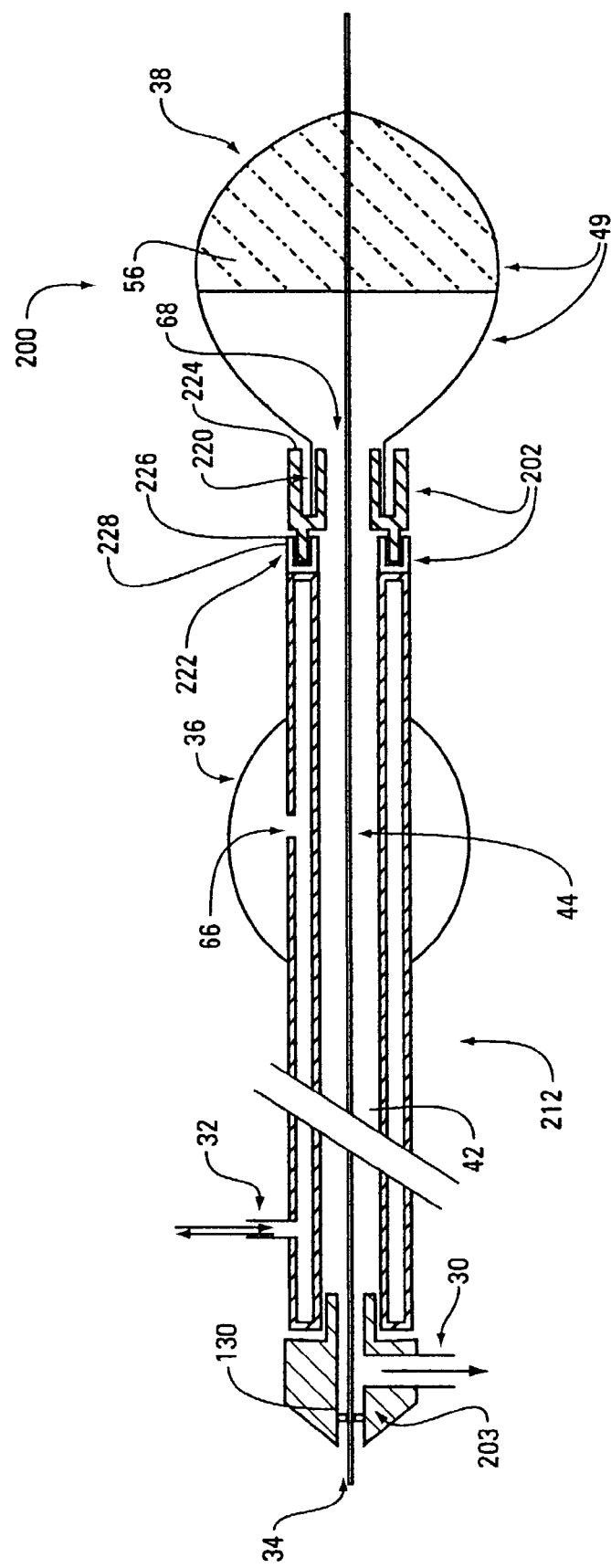
Figure 24B:
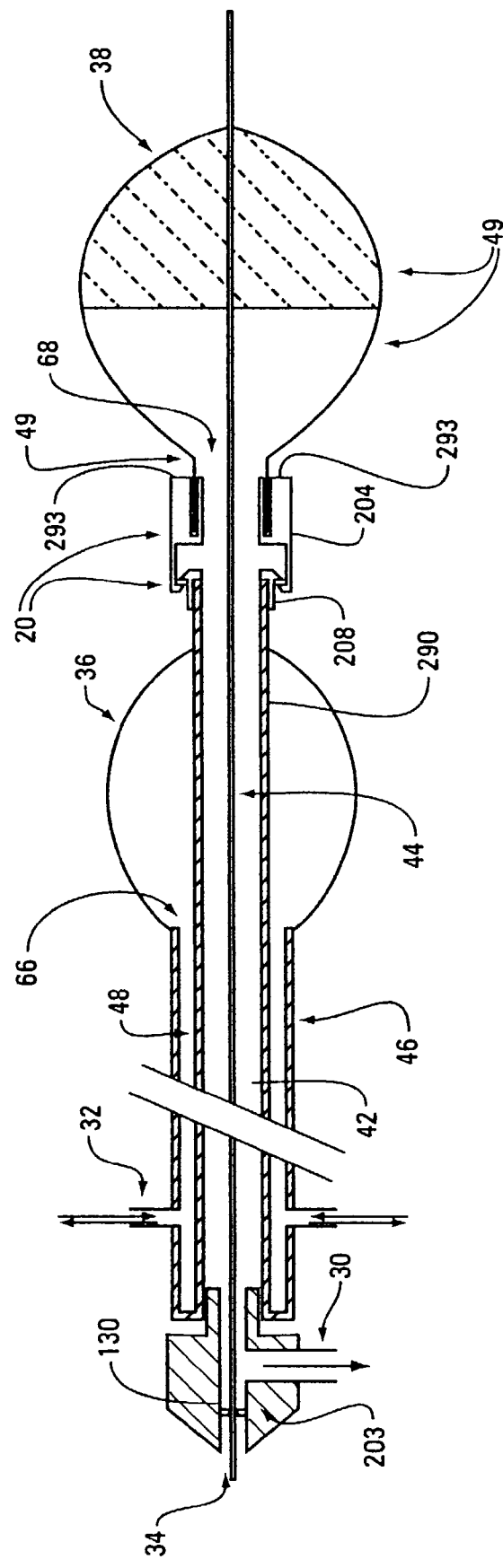

Alternately, as shown in FIGS. 23B and 24B, the snap ring 208 (or the second ring 222) could also be attached to the inner wall 48. These embodiments may be desirable because they provide a lower profile balloon catheter. FIGS. 23B and 24B also show that the snap ring 204 can have a circumferential slot 293 in its proximal end into which the struts 49 are fixed.

Figure 30:
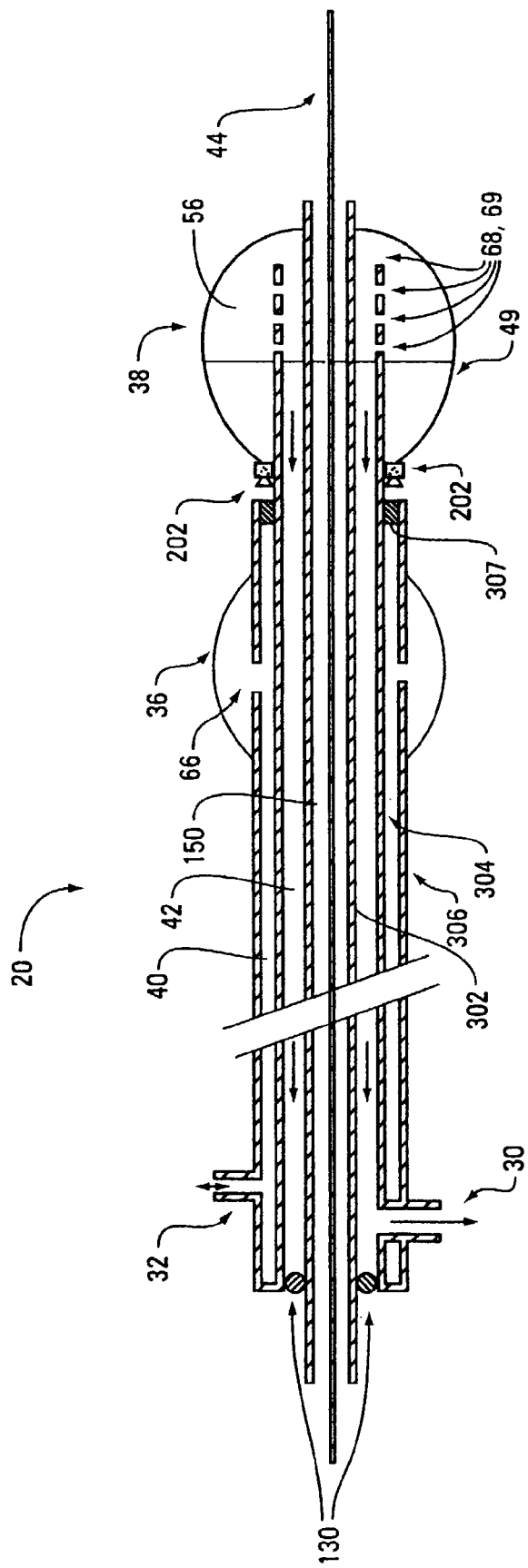
FIG. 30 is a sectional view of a modular trap embodiment having a guidewire lumen.

FIG. 30 shows a modular, antegrade angioplasty device 20 embodiment adapted for use in over-the-wire procedures. This angioplasty device 20 embodiment includes a coupling device 202, an inner wall 302, an intermediate wall 304, an outer wall 306, an end seal 307, a guidewire receiving lumen 150, a suction lumen 42, a suction port 30, a plurality of openings 68 and/or pores 69, an inflation/deflation lumen 40, and a balloon 36. In operation, the trap/barrier 38 is actuated using relative rotational and/or longitudinal motion between the intermediate wall 304 and the inner wall 302. In one embodiment, the handle 320 (shown in FIG. 32) provides the movement to actuate the trap by moving the inner wall 302 relative to intermediate wall 304. These embodiments are desirable because the trap/barrier 38 can be separately attached to the angioplasty balloon catheter component of the angioplasty device 20, which gives greater flexibility for using various sized trap/barrier components with a given angioplasty catheter, while retaining the advantages of over-the-wire operation. The trap 38 in FIG. 30 may also be adapted to incorporate part of the suction lumen, as shown in FIG. 23B.

Figure 25:
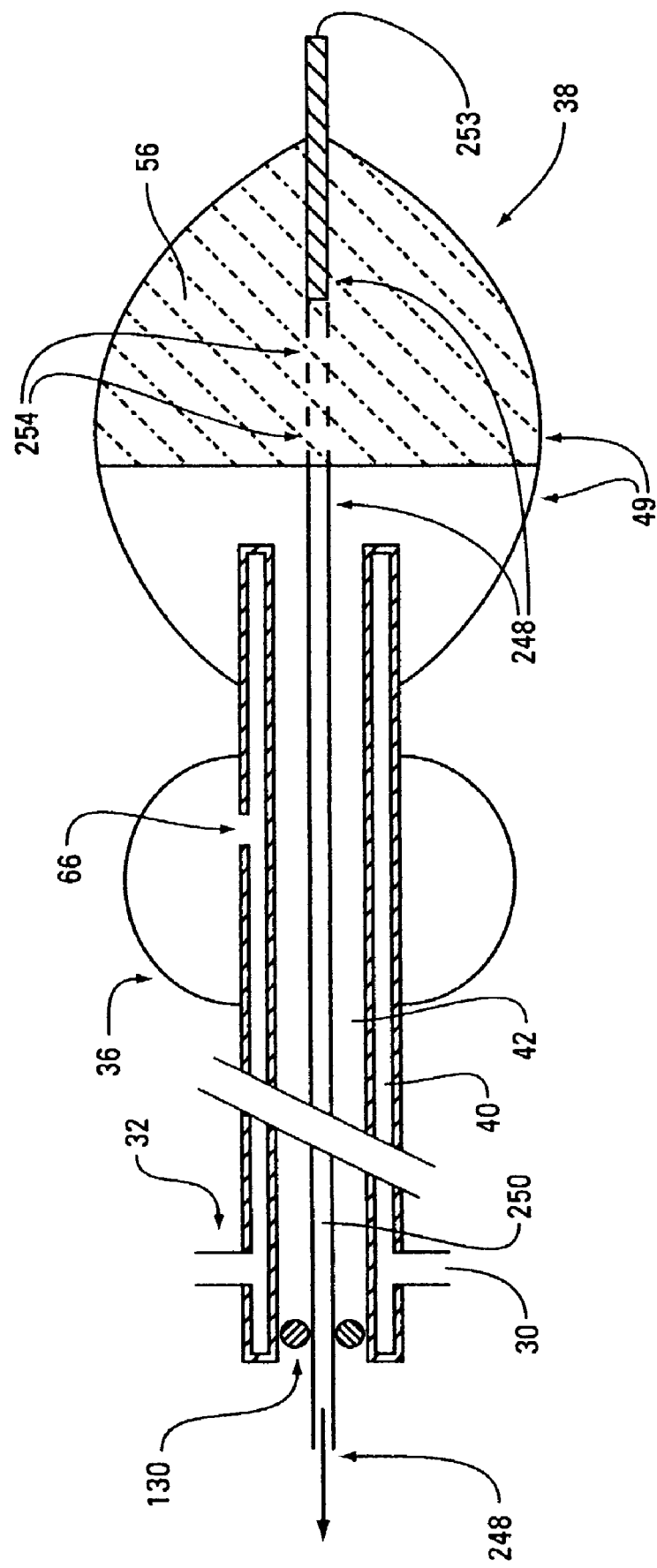
FIG. 25 is a sectional view of an embodiment having a hollow guidewire.
Figure 26:
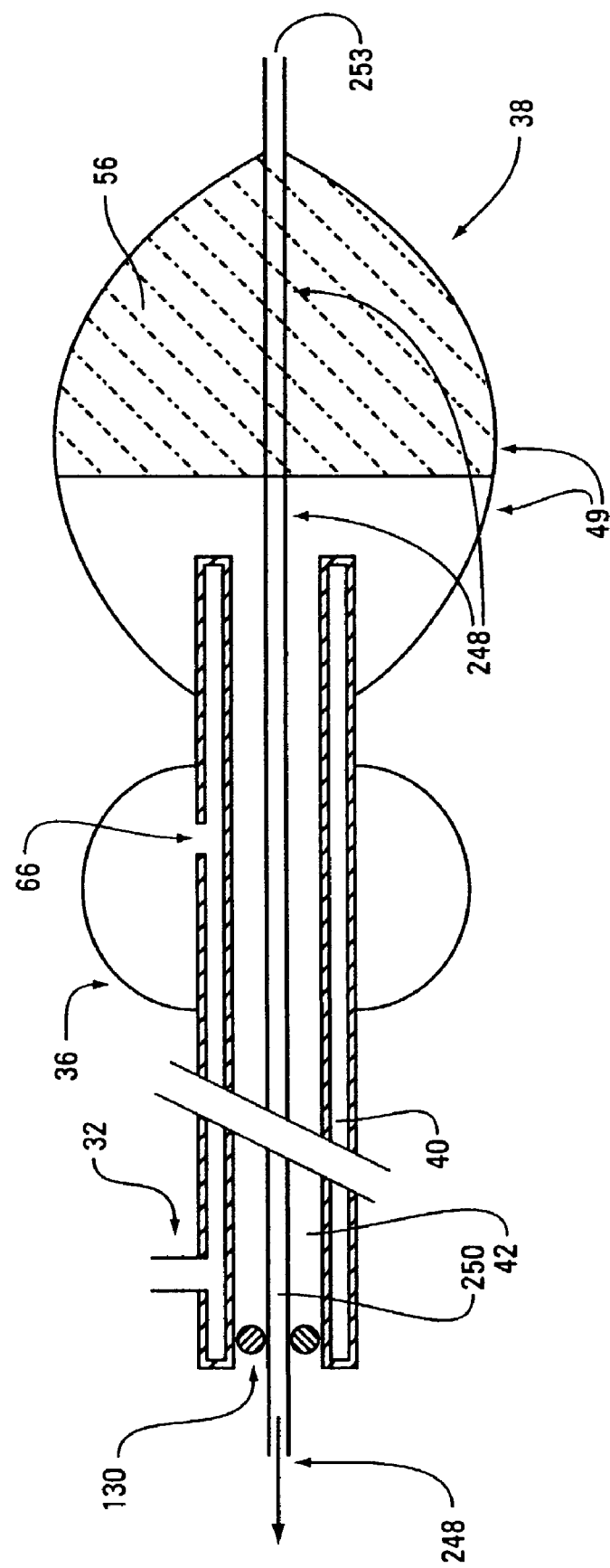
FIG. 26 is a sectional view of an alternate embodiment having a hollow guidewire.

FIGS. 25 and 26 are sectional views of two embodiments having a hollow guidewire 248. These embodiments are desirable because a lumen 250 defined by the hollow guidewire 248 can be used as an alternate suction lumen. The hollow guidewire 248 in these embodiments includes a single opening 253 and/or a plurality of pores 254 that are radially and axially spaced inside the struts 49. The pores 254 allow the alternate suction lumen 250 to help the suction lumen 42 remove smaller particles from the treatment site and suck larger particles into the trap 38. The opening 253 allows the alternate suction lumen 250 to selectively provide suction distal to the angioplasty device 20 while it is being inserted into the treatment site and allows the alternate suction lumen 250 to selectively deliver treatment and/or diagnostic agents. Those skilled in the art will recognize that the hollow guidewire 248 may also be used in the embodiments described with reference to FIGS. 2-24B and 27-30 and that the housing 28 can be modified to include two or more suction ports.

Referring again to FIG. 2, the guidewire port 34 can be any device that allows for relative rotation of the guidewire 44 with respect to the catheter 26. In some embodiments, this relative rotational and/or longitudinal movement is provided by the handle 320 (shown in FIG. 32). In some embodiments, the guidewire port 34 may include an apparatus (not shown) that will indicate the relative position and/or torque of the guidewire with respect to the catheter 26. These embodiments may be desirable because they can help ensure that the struts 49 are rotated into their fully expanded position. The guidewire port 34 may include an auxiliary apparatus (not shown) that maintains the guidewire 44 in a particular orientation corresponding to the maximum expanded position. This apparatus may reduce the number of medical personnel necessary to perform the entire procedure.

The suction port 30 and the inflation port 32 may be any devices that, respectively, allow for operable connection to a vacuum source and a pressure source. In some embodiments, the suction port 30 and the inflation port 32 comprise a polymeric tube that is adapted to receive to a syringe. One syringe may contain the fluid to be injected through the inflation/deflation lumen 40 and into the balloon 36. Another syringe may suck fluid and particles from the trap 38 through the suction lumen 42.

The present invention offers many advantages over the known angioplasty devices. For example, it provides a total capture angioplasty device that can be scaled into small diameter devices. Total capture angioplasty devices having dimensions of about five French and smaller can be easily achieved with the present invention. The present invention can also provide a fixed guidewire to aid insertion into irregular stenosis and a trap 38 that may be actively closed around particles that are too large to be sucked through the suction lumen 42. In addition, the struts 49 can act as an additional trap during actuation. That is, as the trap 38 is contracted, the struts 49 prevent smaller and smaller particles from escaping. In addition, the present invention is desirable because it maximizes the amount and rate of suction per unit size, and because it allows the user to perform multiple tasks using a single catheter device.

Although the present invention has been described in detail with reference to certain embodiments thereof, it may be embodied in other specific forms without departing from the essential spirit or attributes thereof. For example, lumens 42 and 150 could be used to introduce medicinal agents and radiopaque liquids, or to take samples of a fluid before, during, or on completion of a procedure. In these embodiments, the medicinal agent could be introduced into the catheter 26 through an appropriate port by suitable means, such as a syringe. These embodiments may be particularly desirable if combined with a porous membrane 56. In addition, the stainless steel guidewire 44 could be replaced by an optical fiber. These embodiments may be desirable because they could allow the surgeon to view the treatment site before and after the procedure. Still other embodiments of the present invention may coat the guidewire 44 and the catheter 26 with a lubricant, such as polytetrafluoroethylene ("PTFE"), to reduce friction.

Those skilled in the art will recognize that the term "angioplasty" as used throughout this specification and the claims was intended to include, without being limited to: (1) any of the medical and/or veterinary procedures and treatments described in the background section; (2) procedures and treatments similar to those described in the background section; and/or (3) any other treatment or procedure involving the removal of an obstruction from vessels or vessel-like structures, regardless of whether such structures are part of or associated with a living organism, and specifically including, without being limited to, the use of the present invention to remove obstructions from "non-living" tubes, tubules, conduits, fibers or other structures in non-medical or industrial applications. Thus, the present invention could, for example, be used to remove an obstruction from a fluid delivery tube within a machine under conditions where it would be undesirable for particles of the obstruction to break free and continue down the tube, e.g., if the machine were still running and particles would jeopardize continued operation.

Those skilled in the art will also recognize that the accompanying figures and this description depicted and described embodiments of the present invention, and features and components thereof. With regard to means for fastening, mounting, attaching or connecting the components of the present invention to form the mechanism as a whole, unless specifically described otherwise, such means were intended to encompass conventional fasteners such as machine screws, nut and bolt connectors, machine threaded connectors, snap rings, screw clamps, rivets, nuts and bolts, toggles, pins and the like. Components may also be connected by welding, brazing, friction fitting, adhesives, or deformation, if appropriate. Unless specifically otherwise disclosed or taught, materials for making components of the present invention were selected from appropriate materials, such as metal, metallic alloys, fibers, polymers and the like, and appropriate manufacturing or production methods including casting, extruding, molding and machining may be used. In addition, any references to front and back, right and left, top and bottom and upper and lower were intended for convenience of description, not to limit the present invention or its components to any one positional or spatial orientation. Therefore, it is desired that the embodiments described herein be considered in all respects as illustrative, not restrictive, and that reference be made to the appended claims for determining the scope of the invention.

Although the present invention has been described with reference to illustrative embodiments, persons skilled in the art will recognize that changes may be made in form and detail without departing from the spirit and scope of the invention.

We claim:

1. An apparatus for insertion into a vessel-like structure, the apparatus comprising:
    a catheter for insertion into the vessel-like structure, the catheter having a catheter wall and a lumen extending longitudinally theretbrough;
    a moveable member disposed within the lumen;
    at least one helically twisted flexible strut fixedly connected to the catheter wall and to the moveable member;
    a membrane operably connected to the at least one flexible strut to form a trap, wherein relative motion between the catheter wall and the moveable member actuates the trap between a helically twisted contracted position and a helically twisted expanded position, wherein the relative motion comprises relative rotational motion;
    at least one suction aperture situated within the boundary defined by the at least one helically twisted flexible strut; and
    a suction lumen extending longitudinally through the catheter, the suction lumen being in operable communication with the at least one suction aperture.

2. The apparatus of claim 1, further comprising a balloon operably connected to the catheter and adapted to compress an obstruction.

3. The angioplasty device of claim 2, wherein the catheter further defines an inflation/deflation lumen fluidly connected to the balloon.

4. The apparatus of claim 1, wherein the helically twisted contracted position forms a waist.

5. The apparatus of claim 1, wherein the trap is further actuated by relative longitudinal motion between the catheter wall and the moveable member.

6. The apparatus of claim 1, wherein the trap is actuated by relative rotational and longitudinal motion between the catheter wall and the moveable member.

7. The apparatus of claim 1, wherein the moveable member defines a guidewire lumen adapted to slidably receive a guidewire.

8. The apparatus of claim 1, wherein the guidewire is hollow.

9. The apparatus of claim 1, wherein the at least one strut forms a profile having a first portion and a second portion, wherein the first portion has a first radius of curvature and the second portion has a second radius of curvature, the first radius of curvature is larger than the second radius of curvature causing the first portion to contract first to form a cocoon.

10. The apparatus of claim 1, wherein the at least one strut includes a first portion and a second portion.

11. The apparatus of claim 10, wherein the first portion is formed to be thinner than the second portion causing the first portion to contract first to form a cocoon.

12. The apparatus of claim 10, wherein the first portion is formed of a material more resilient than the second portion causing the first portion to contract first to form a cocoon.

13. The apparatus of claim 10, wherein a cross section of the first portion has a smaller moment of inertia than a cross section of the second portion with a larger moment of inertia, causing the first portion to contract first to form a cocoon.

14. The apparatus of claim 1, further comprising a coupling device that selectively couples the trap to the catheter wall.

15. The apparatus of claim 1, comprising a plurality of helically twisted flexible struts.

16. The apparatus of claim 1, comprising a handle to provide longitudinal and rotational movement of the moveable member for actuating the trap.

17. The apparatus of claim 1, wherein the moveable member is a guidewire having a solid first portion and a second portion that includes a suction lumen.

18. The apparatus of claim 1, wherein the suction lumen has a first portion with a first diameter and a second portion with a second diameter, wherein the second diameter is larger than the first diameter.

19. An apparatus for insertion into a vessel-like structure, the apparatus comprising:
- a catheter for insertion into the vessel-like structure, the catheter having a catheter wall and a lumen extending longitudinally therethrough;
- a moveable member disposed within the lumen;
- at least one helically twisted flexible strut fixedly connected to the catheter wall and to the moveable member;
- a membrane operably connected to the at least one flexible strut to form a trap, wherein relative motion between the catheter wall and the moveable member actuates the trap between a helically twisted contracted position and a helically twisted expanded position, wherein the relative motion comprises relative rotational motion.motion;
- a balloon operably connected to the catheter and adapted to compress an obstruction;
- at least one suction aperture situated between the balloon and a distal end of the trap; and
- a suction lumen extending longitudinally through the catheter, the suction lumen in operable communication with the at least one suction aperture.

20. An apparatus for insertion into a vessel-like structure, the apparatus comprising:
- a catheter for insertion into the vessel-like structure, the catheter having a catheter wall and a lumen extending longitudinally therethrough;
- a moveable member disposed within the lumen;
- at least one helically twisted flexible strut fixedly connected to the catheter wall and to the moveable member; and
- a membrane operably connected to the at least one flexible strut to form a trap, wherein relative motion between the catheter wall and the moveable member actuates the trap between a helically twisted contracted position and a helically twisted expanded position, wherein the relative motion comprises relative rotational motion;
- a balloon operably connected to the catheter and adapted to compress an obstruction;
- an inflation/deflation lumen defined by the catheter and fluidly connected to the balloon;
- at least one suction aperture defined by the cathether, the at least one suction aperture being situated between the balloon and the distal end of the trap; and
- a suction lumen extending longitudinally through the catheter, the suction lumen in operable communication with the at least one suction aperture.

* * * * *

UNITED STATES PATENT AND TRADEMARK OFFICE
CERTIFICATE OF CORRECTION

| | |
|---|---|
| PATENT NO. | : 7,322,957 B2 |
| APPLICATION NO. | : 10/163077 |
| DATED | : January 29, 2008 |
| INVENTOR(S) | : Kletschka et al. |

It is certified that error appears in the above-identified patent and that said Letters Patent is hereby corrected as shown below:

ON THE TITLE PAGE
Item 63 should read:
Continuation-in-part of application No. 10/119,054, filed on Apr. 9, 2002, which is a continuation-in-part of application No. 09/718,732, filed on Nov. 22, 2000, now abandoned, which is a continuation-in-part of application No. 09/495,833, filed on Feb. 1, 2000, now Pat. No. 6,443,926.

Column 1, Lines 7-12 should read:
    This application is a continuation-in-part of U.S. patent application Ser. No. 10/119,054, filed Apr. 9, 2002, which is a continuation-in-part of U.S. patent application Ser. No. 09/718,732, filed Nov. 22, 2000, now abandoned, which is a continuation-in-part of U.S. patent application Ser. No. 09/495,833, filed Feb. 1, 2000, now U.S. Pat. No. 6,443,926, all of which are herein incorporated by reference.

| Column | Line | PTO | Should Read |
|---|---|---|---|
| 16 | 50 | "such that 25 the" | -- such that the -- |

| IN THE CLAIMS | | PTO | Should Read |
|---|---|---|---|
| Column | Line | | |
| 26 | 42 | "therebrough" | -- therethrough -- |
| 28 | 12 | "motion. motion;" | -- motion. -- |

Signed and Sealed this

Eighth Day of July, 2008

JON W. DUDAS
*Director of the United States Patent and Trademark Office*